United States Patent
Grunwald et al.

(10) Patent No.: US 11,072,825 B2
(45) Date of Patent: *Jul. 27, 2021

(54) METHOD FOR INDICATING THE PROGRESS OF AMPLIFICATION OF NUCLEIC ACIDS AND KIT FOR PERFORMING THE SAME

(71) Applicant: AGCT GmbH, Luebeck (DE)

(72) Inventors: Christian Grunwald, Giessen (DE); Dmitry Cherkasov, Marburg (DE); Norbert Basler, Grosshansdorf (DE); Claus Becker, Oetigheim (DE); Hans-Joerg Hess, Berlin (DE); Andreas Mueller-Hermann, Munich (DE)

(73) Assignee: AGCT GmbH

( * ) Notice: Subject to any disclaimer, the term of this patent is extended or adjusted under 35 U.S.C. 154(b) by 0 days.

This patent is subject to a terminal disclaimer.

(21) Appl. No.: 16/975,489

(22) PCT Filed: Feb. 25, 2019

(86) PCT No.: PCT/EP2019/054512
§ 371 (c)(1),
(2) Date: Aug. 25, 2020

(87) PCT Pub. No.: WO2019/162478
PCT Pub. Date: Aug. 29, 2019

(65) Prior Publication Data
US 2021/0024978 A1 Jan. 28, 2021

(30) Foreign Application Priority Data
Feb. 26, 2018 (EP) ..................................... 18158514

(51) Int. Cl.
*C12Q 1/68* (2018.01)
*C12Q 1/686* (2018.01)
*C12Q 1/6876* (2018.01)

(52) U.S. Cl.
CPC .......... *C12Q 1/686* (2013.01); *C12Q 1/6876* (2013.01); *C12Q 2527/101* (2013.01); *C12Q 2565/60* (2013.01)

(58) Field of Classification Search
CPC .................. C12Q 1/686; C12Q 1/6876; C12Q 2527/101; C12Q 2565/60; C12Q 2525/155; C12Q 2525/186; C12Q 2525/113; C12Q 2525/101; C12Q 2531/119; C12Q 2537/162; C12Q 2537/1373

See application file for complete search history.

(56) References Cited

U.S. PATENT DOCUMENTS

| | | | |
|---|---|---|---|
| 9,284,602 B2* | 3/2016 | Zhang | C12Q 1/686 |
| 10,612,082 B2* | 4/2020 | Cherkasov | C12Q 1/6853 |
| 2007/0054301 A1* | 3/2007 | Becker | C12Q 1/6853 435/6.12 |
| 2015/0203905 A1* | 7/2015 | Takahashi | C12Q 1/6834 435/6.11 |
| 2015/0344943 A1* | 12/2015 | Oberstrass | C12Q 1/6848 506/26 |

FOREIGN PATENT DOCUMENTS

| | | |
|---|---|---|
| EP | 3287528 A1 | 2/2018 |
| WO | 2004076683 A2 | 9/2004 |
| WO | 2007030505 A1 | 3/2007 |
| WO | 2009150467 A1 | 12/2009 |
| WO | 2012058488 A1 | 5/2012 |
| WO | 2014173963 A1 | 10/2014 |
| WO | 2015075198 A1 | 5/2015 |
| WO | 2015161054 A2 | 10/2015 |

OTHER PUBLICATIONS

I. V. Smolina: "End Invasion of Peptide Nucleic acids (PNAs) with mixed-base composition into linear DNA duplexes" Nucleic Acids Research, 2005, vol. 33, No. 17 e146.
International Search Report and Written Opinion for Application No. PCT/EP2019/054512, dated Jun. 12, 2019, 15 pages.

* cited by examiner

*Primary Examiner* — David C Thomas
(74) *Attorney, Agent, or Firm* — Kacvinsky Daisak Bluni, PLLC

(57) ABSTRACT

It is disclosed a method for the detection of an amplification of nucleic acids in which substantially use is made of the fact that a pre-defined nucleic acid chain (target sequence) can be multiplied/amplified in the presence of a target sequence-specific activator oligonucleotide. The target sequence-specific activator oligonucleotide causes the separation of re-synthesized complementary primer extension products by means of strand displacement, so that a new primer oligonucleotide can attach to the respective template strand. The thus formed complex of a primer oligonucleotide and a template strand can initiate a new primer extension reaction. The thus formed primer extension products in turn function as templates, so that an exponential amplification reaction results. Amplification is detected by a detection system.

14 Claims, 36 Drawing Sheets
Specification includes a Sequence Listing.

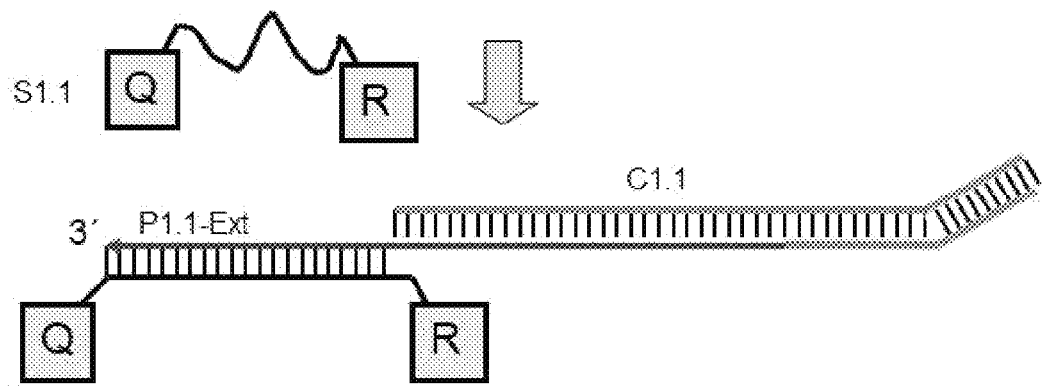
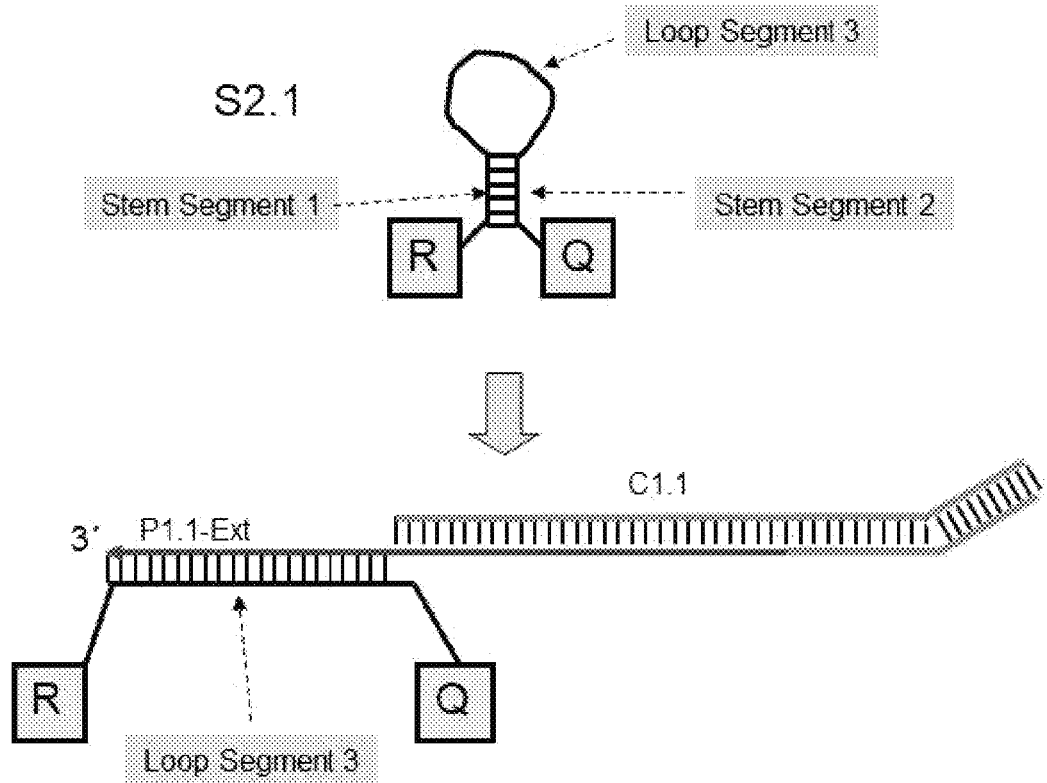
Figure 2

Amplification starting from hg DNA

First Primer Oligonucleotide

Complementary Binding of the first Primer to the nucleic acid to be amplified

First Primer Oligonucleotide and First Primer Extension Product

Complementary Binding of the first Primer to the nucleic acid to be amplified

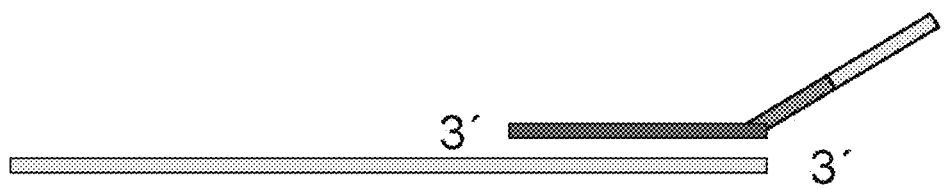

The first primer oligonucleotide specifically bound to the complementary position in the template strand

complementary extended first primer oligonucleotide bound to the complementary position in the template strand after primer extension

Figure 17

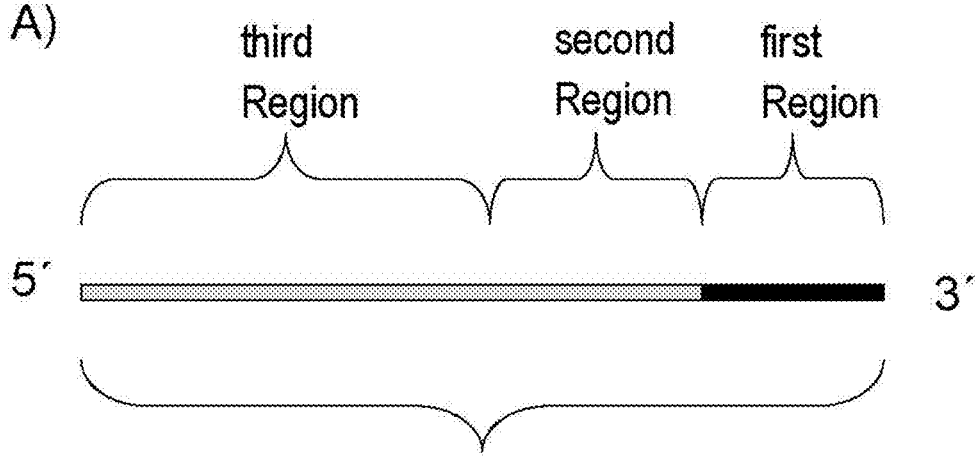
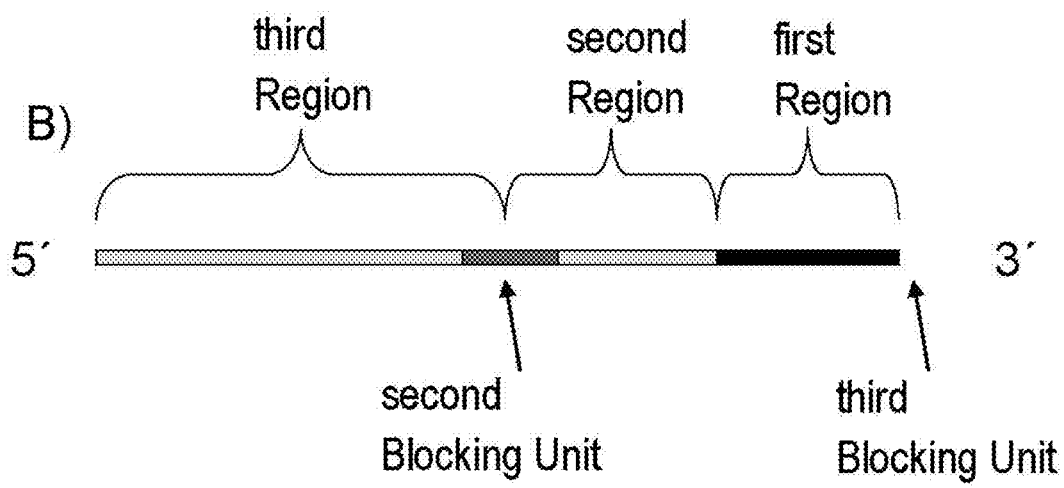
Figure 19

Interactions between Components

Interactions between complementary regions of individual components before the synthesis of the second primer extension product

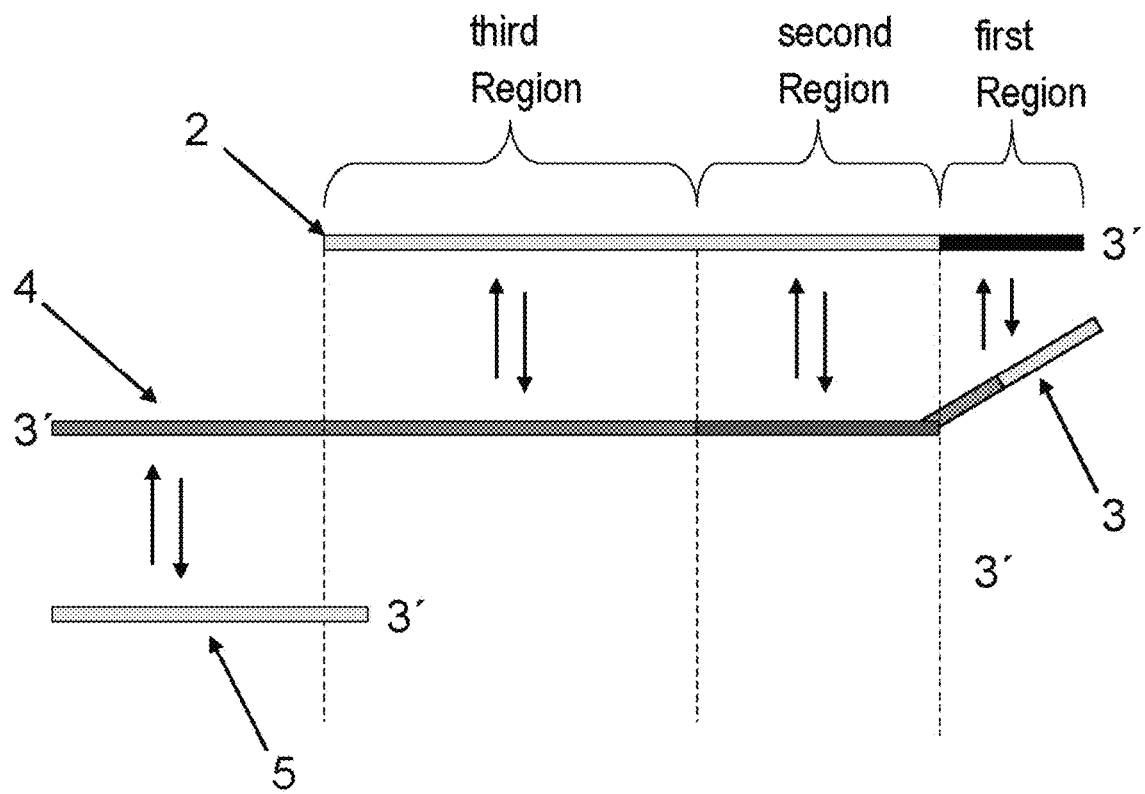

1 = nucleic acid to be amplified
2 = activator oligonucleotide
3 = the first primer oligonucleotide
4 = the extension product of the first primer oligonucleotide
5 = the second primer oligonucleotide

Figure 28

Interactions between Components

Interactions between complementary regions of individual components after the synthesis of the second primer extension product

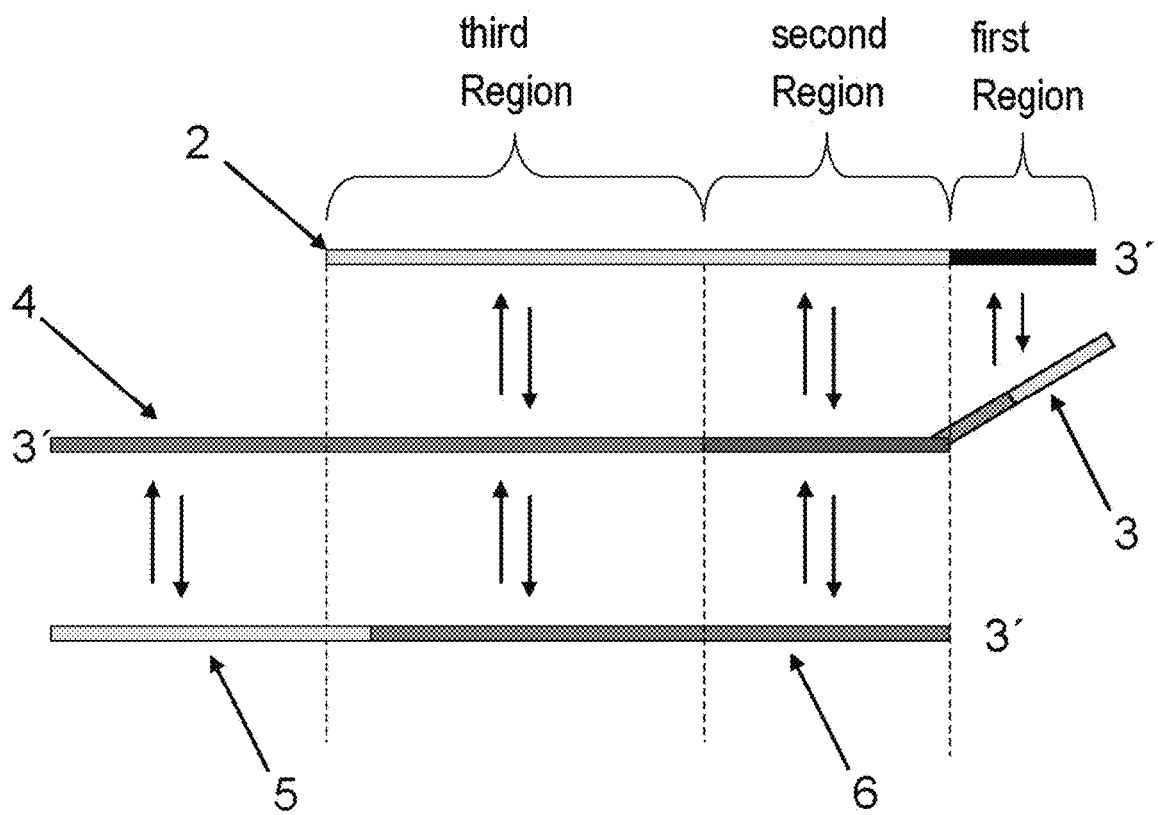

1 = nucleic acid to be amplified
2 = activator oligonucleotide
3 = the first primer oligonucleotide
4 = the extension product of the first primer oligonucleotide
5 = the second primer oligonucleotide
6 = the extension product of the second primer oligonucleotide

Figure 29

Sequence Products of the Reaction

First and Second Primer Extension Products

3 = the first primer oligonucleotide
4 = the extension product of the first primer oligonucleotide
5 = the second primer oligonucleotide
6 = the extension product of the second primer oligonucleotide

A) Primer Oligonucleotides
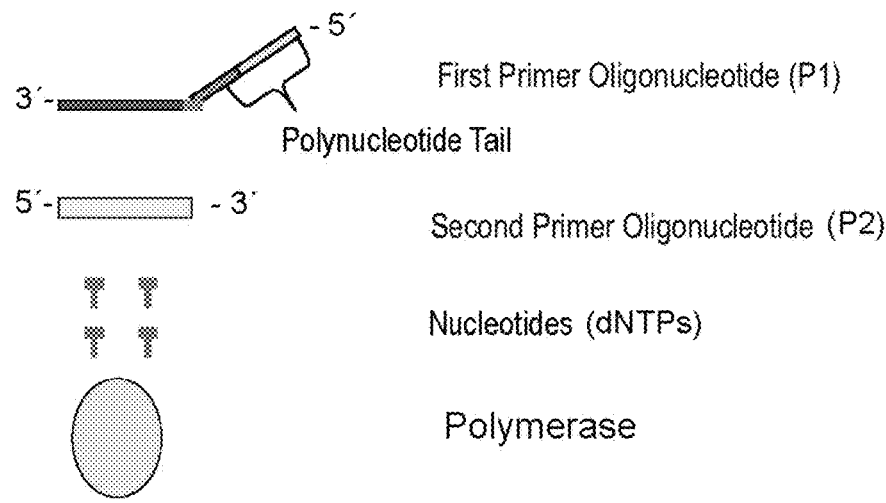
B) Nucleic acid to be amplified
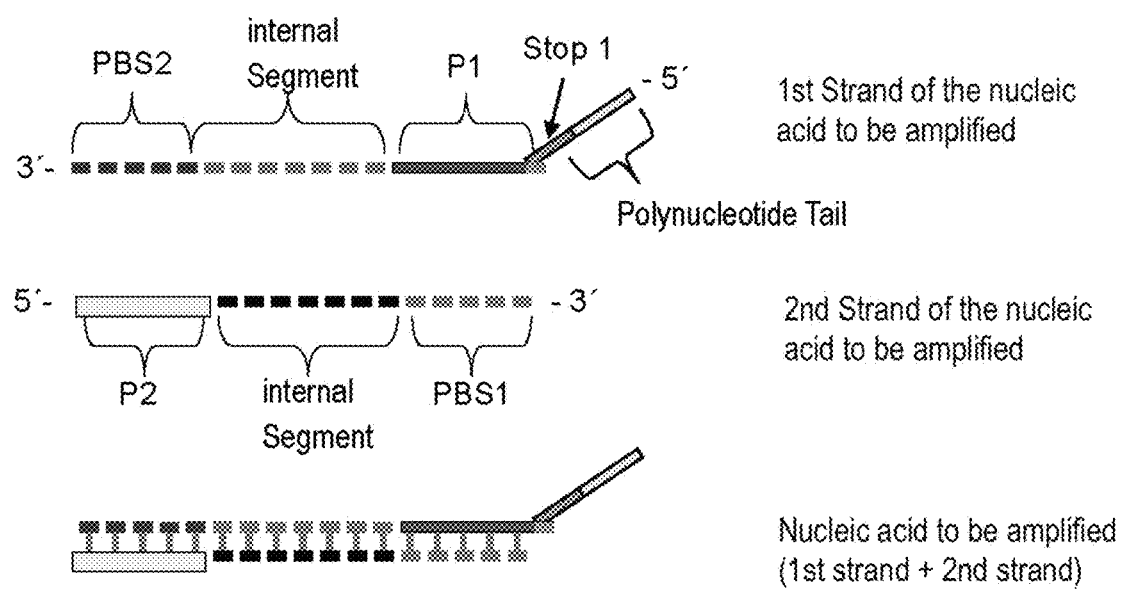
Figure 33

Strand displacement by the activator oligonucleotide

Interactions between Components in the Reaction

Change of States:
double-stranded Sections vs. single-stranded Sections

Intermediate Step:
separation of the second
primer extension product from the complex
with the double strand consisting of
the first primer extension product and the
activator oligonucleotide

METHOD FOR INDICATING THE PROGRESS OF AMPLIFICATION OF NUCLEIC ACIDS AND KIT FOR PERFORMING THE SAME

Today, synthesis of nucleic acid chains plays a central role in biotechnology. Methods like PCR have significantly developed both the research landscape and industrial fields of application such as diagnostics in medicine and food industry. The combination of PCR with other technologies such as sequencing, real-time detection, microarray technology, microfluidic management etc. has contributed to the technological development of the basic technology and was able to partly overcome some barriers of the PCR basic technology. Also, further amplification methods such as isothermal amplification techniques (LAMP, HDA, RPA, TMA, SDA etc.) have been developed. They have especially been intended for use in the field of POCT.

Despite enormous progress in this field PCR plays the central role and thus, defines the individual technological barriers of the applications.

One of the properties of common amplification methods such as PCR is that during the amplification operation of the nucleic acid the amplified sequence parts between both primers are not controlled. Substantially, primer binding is in focus of optimizations of PCR amplification reactions. At the beginning of the PCR amplification and its course continuously more or less specific primer bindings and initiation of the synthesis of main products and by-products occur. For example, the by-products may be generated as a result of a non-specific primer extension event in a synthesis cycle. In case of a backward synthesis reaction that optionally takes place the non-specifically extended primer is read as a template what generally results in the formation of a complete primer binding site. Thus, an incorrect sequence information is transferred from one synthesis cycle to the next synthesis cycle what in the sum of synthesis cycles not only results in the initial generation, but above all in the exponential increase of by-products.

Such side reactions may possibly result in the initial generation and exponential increase of fragments that interfere with the main reaction (amplification of a target sequence) and result in interferences in following steps of analysis, respectively. Such by-products typically comprise primer sequences and corresponding primer sequences so that their amplification can be in parallel to the main reaction. Instead of a target sequence, however, such by-products comprise another nucleic acid sequence.

As a matter of priority, specificity of PCR amplification is achieved by optimizing the primer binding to target sequences. Here, for example additional oligonucleotides can be used that are capable of partially binding to primers and thus, competitively take part in the primer binding to other nucleic acid chains. Such probes generally bind to a sequence part of the primer and on the primer leave a single-stranded sequence part unoccupied, so that the primer with this part can bind to the target nucleic acid and initiate a synthesis reaction. Here, specificity of a primer binding is to be improved by the fact that primer template mismatches can competitively be displaced by such oligonucleotides. As a result, it is generally possible to improve the specificity of the initiation of PCR reactions. The effect of such oligonucleotides is limited to the interaction with primer sequences. Such additional oligonucleotides do not interact with the nucleic acid chain to be amplified in sections between both primers. However, due to a molar excess of primers, non-specific interactions of primers with templates can occur during amplification. If such a non-specific event of primer extension takes place (initiation of an exponential side reaction) a fully functional primer binding site is formed as a result or as part of backward synthesis of a complementary strand of the by-product. The presence of such a complete primer binding site in the by-product results in a loss of the competitive effect of such additional oligonucleotides on primer binding. Thus, controlling the specificity of the binding of a primer to the template by such oligonucleotides makes only initiation of a side reaction less likely, but can hardly affect its exponential amplification after a by-product has been generated.

Generally, the specificity of the synthesis of an amplification method can be improved with the reduced generation and co-amplification of by-products that differ from the target sequence, for example contribute to an improvement of diagnostic methods.

It is an object of the present invention to provide a method and components that enable enzymatic synthesis and amplification of nucleic acid chains. It is intended to provide a new enzymatic method and components for the synthesis of nucleic acid chains as well as the amplification of nucleic acid chains, with which a continuous (on-line) signal detection is provided, wherein the signal detection (monitoring/detection) is mediated or supported, respectively, by sequence-specific oligonucleotide probes.

A further object of the invention is to provide a method with improved specificity of the synthesis of target nucleic acid chains in an exponential amplification.

A further object of the invention is to provide means for implementing an exponential amplification method with improved specificity of the synthesis.

With the method according to the invention nucleic acid chains of a defined sequence composition are to be synthesized and amplified, respectively, and detected.

The problem of the invention is solved by the provision of amplification methods and corresponding means for performing the same. Execution of the amplification method has already been described in PCT application (PCT/EP2017/071011) and the European application (EP-A 16185624.0). For details on the execution of the amplification the skilled person is referred to said application. Said application is herewith incorporated by reference to the whole extent.

Preferably, the amplification is an exponential amplification in which re-synthesized products of both primers (primer extension products) occur as templates for further synthesis steps. Here, primer sequences are at least partially copied, so that complementary primer binding sites are generated that are present as sequence segments of a double strand immediately after having been synthesized. In the amplification method synthesis steps of both strands and double strand opening steps of the re-synthesized sequence parts take place in mutual alternation. A sufficient double strand separation after a synthesis represents an important prerequisite for a further synthesis. Altogether, such an alternation of synthesis and double strand separation steps can result in an exponential amplification.

In the amplification method according to the invention the double strand opening of main products of the amplification (amplification of a target sequence-comprising nucleic acid chains) inter alia is by means of an oligonucleotide, referred to as activator oligonucleotide. The activator oligonucleotide preferably comprises sequence segments that correspond to the target sequence.

In detail, according to the invention strand separation is achieved by employing activator oligonucleotides having pre-defined sequences that preferably separate a re-synthesized double strand consisting of both specific primer extension products by means of a sequence-dependent nucleic acid mediated strand displacement. The resulting single-stranded segments of primer extension products comprise the target sequence as well as corresponding primer binding sites that can serve as binding sites for further primer oligonucleotides, so that an exponential amplification of nucleic acid chains to be amplified is achieved. Basically, the primer extension reactions and strand displacement reactions preferably take place at the same time. Amplification preferably takes place under reaction conditions that do not allow a spontaneous separation of both specific synthesized primer extension products.

Specific exponential amplification of a target sequence-comprising nucleic acid chain comprises a repetition of synthesis steps and double strand opening steps (activation steps for primer binding sites) as a mandatory prerequisite for the multiplication of the nucleic acid chain.

Opening of synthesized double strands is implemented as a reaction step that is to be sequence-specifically affected by the activator oligonucleotide. Said opening can be done completely, up to the dissociation of both complementary primer extension products, or may also be done partial.

According to the invention the activator oligonucleotide comprises sequence parts that can interact with the target sequence and further sequence parts that cause, permit or favor, respectively said interaction. In the course of the interaction with the activator oligonucleotide double-stranded sections of the synthesized primer extension products are converted into the single-stranded form via sequence-specific strand displacement. This process is sequence-dependent: only if the sequence of the synthesized double strand has a certain amount of complementarity with the corresponding sequence of the activator oligonucleotide a sufficient double strand opening occurs, so that the sequence parts essential for continuing the synthesis such as e.g. primer binding sites are converted into the single-stranded form, which corresponds to an "active state". Thus, the activator oligonucleotide specifically "activates" the re-synthesized primer extension products comprising the target sequence for further synthesis steps.

In contrast, sequence parts that do not comprise a target sequence are not converted into the single-stranded state and remain as double strand, which corresponds to an "inactive" state. The potential primer binding sites in such a double strand are disadvantaged or completely prevented from interaction with new primers, so that further synthesis steps on such "non-activated" strands generally do not take place. This lacking or reduced activation (i.e. conversion into a single-stranded state) of synthesized nucleic acid strands after a synthesis step results in the fact that in the subsequent synthesis step only a reduced amount of primers can successfully take part in a primer extension reaction.

Due to an exponential amplification of main products (a nucleic acid chain to be amplified that comprises target sequences) to be aimed several synthesis steps and activation steps (double strand opening steps) are combined in one amplification method and performed or repeated, respectively until the desired amount of the specific nucleic acid chain is provided.

Here, the reaction conditions (e.g., temperature) are designed such that a spontaneous separation of complementary primer extension products in the absence of an activator oligonucleotide is unlikely or significantly decelerated.

Thus, the increase in the specificity of an amplification to be aimed results from the sequence-dependency of the separation of complementary primer extension products comprising a target sequence: the activator oligonucleotide enables or favors this double strand separation as a result of the matching of its sequence parts with given sequence parts of the primer extension products. This matching is verified after each synthesis cycle by the activator oligonucleotide. The exponential amplification results as a consequence from successful repetitions from synthesis processes and sequence-specific strand displacements by the activator oligonucleotide, i.e. "activations" (double strand openings/double strand separations/strand displacement processes resulting in a single-stranded form of corresponding primer binding sites) of re-synthesized primer extension products.

The problems of the invention are solved in that there is provided a combination of an amplification method with a detection system, wherein the detection system comprises at least one oligonucleotide probe and at least one fluorescence reporter. Moreover, the detection system comprises a fluorescence quencher (also referred to as quencher) that matches with the fluorescence reporter, wherein said quencher under certain circumstances is able to reduce the fluorescence signals of the fluorescence reporter or the signal intensity, respectively. In a further embodiment, a detection system can comprise a donor fluorophore matching with the fluorescence reporter, so that said donor fluorophore under certain circumstances is able to permit the fluorescence signals of the fluorescence reporter by energy transfer. In a further embodiment, the detection system can comprise the activator oligonucleotide, wherein the activator oligonucleotide comprises either a fluorescence reporter or a donor fluorophore or a fluorescence quencher.

Arrangement of individual elements (fluorescence reporter, fluorescence quencher, donor fluorophore) on the oligonucleotide probe and/or on the activator oligonucleotide in the presence of a first primer extension product is to result in a change of the fluorescence signal of the fluorescence reporter to form complementary complexes, each. Said change, depending on the chosen constellation between a fluorescence reporter and/or a donor fluorophore and/or a fluorescence quencher can result in an increase or decrease of the signal intensity of the fluorescence reporter. Said change can be detected with known suitable means during or after reaction proceeded. Here, the detection of changes of the signal can enable conclusions about the course of the reaction: e.g. amplitude of the signal, kinetics, time or concentration dependency of the signal occurrence, respectively. When using several target sequences, multiplex analyses can be coded correspondingly by different spectral properties, so that also several reactions can be observed in parallel to each other.

The present invention describes some embodiments of oligonucleotide probes that are particularly advantageous to detect the progress of the reaction. By suitable positioning of single elements of the detection system on an oligonucleotide probe and/or activator oligonucleotide, it is possible to detect binding events of said components to the first primer extension product by signal increase or signal decrease. Such a detection may take place either during the amplification (e.g. as online detection) or in suitable time intervals or even only at the end of the reaction.

Thus, using a pre-defined activator oligonucleotide enables a sequence-dependent verification of the contents of primer extension products between individual synthesis steps during the exponential amplification and obtaining a selection or choice of sequences for subsequent synthesis steps. Here, distinction can be made between "active", single-stranded states of re-synthesized specific primer extension products as a result of a successful interaction with an activator oligonucleotide, and "inactive", double-stranded states of re-synthesized non-specific primer extension products as a result of a deficient and/or insufficient and/or reduced and/or decelerated interaction with an activator oligonucleotide.

The following effects result for an exponential amplification:

Under non-denaturant conditions separation of specifically synthesized strands takes place with cooperation of an activator oligonucleotide.

Exponential amplification of target sequence-comprising nucleic acid chains is sequence-controlled (main reaction). Said sequence control takes place after each synthesis step and includes sequence segments lying between primers and comprising a target sequence. The successful verification of the results of the synthesis after each synthesis step results in the separation of both specific primer extension products, which is the prerequisite for further specific synthesis steps.

During the amplification an initial generation of non-specific primer extension products basically cannot be excluded (by-products). Due to a template dependency such non-specific primer extension products immediately after their synthesis are generally present in the double-stranded form. However, the interaction with the activator oligonucleotide either completely fails to come or is limited, so that there is no strand separation or the strand separation is decelerated over the main reaction. Thus, there is no transfer of incorrect sequence information from one synthesis cycle to the next.

By the choice of the reaction conditions and the design of an activator oligonucleotide it is thus possible to specifically affect the efficacy of the regeneration of correct nucleic acid chain templates between single synthesis steps during an amplification method. Generally, the higher the degree of matching of the synthesized sequence with the given sequence of the activator oligonucleotide, the more successful the separation of the synthesized products and in turn the more successful the regeneration of correct templates from one synthesis step to the next. On the other hand, a sequence divergence in by-products results in an insufficient regeneration of template strands and thus, in a deceleration of the synthesis initiation and a reduction of the yield in each subsequent cycle. The whole exponential amplification of by-products either proceeds more slowly or does not take place at all and/or remains at an undetectable level.

Thus, the method enables a verification of the synthesized sequences in real-time, i.e. without stopping the reactions and thus, represents potential for the development of homogeneous assays in which all components of the assay are already present in the reaction mixture at the beginning of a reaction.

Terms and Definitions

In the context of the present invention the terms used have the following meaning: The term "oligonucleotide", as used here with respect to primers, activator oligonucleotide, probes, nucleic acid chain to be amplified, is defined as a molecule comprising two or more, preferably more than three deoxyribonucleotides and/or ribonucleotides and/or nucleotide modifications and/or non-nucleotide modifications. Its length comprises for example regions between 3 to 300 nucleotide units or analogues thereof, preferably between 5 to 200 nucleotide units or analogues thereof. Its exact size depends on a number of factors that in turn depend on the final function or use of the oligonucleotides.

The term "primer", as used herein, relates to an oligonucleotide, regardless of whether it is naturally occurring, e.g. in a purified restriction cleavage, or was synthetically produced. A primer is capable of acting as an initiation point of the synthesis if it is used under conditions in which the synthesis of a primer extension product that is complementary to a nucleic acid strand is induced, i.e. in the presence of nucleotides and an inducing agent such as e.g., DNA polymerase at a suitable temperature and a suitable pH value. Preferably, the primer for a maximum efficacy in the amplification is single-stranded. The primer has to be sufficiently long in order to initiate synthesis of the extension product in the presence of the inducing agent. The exact length of the primer depends on a number of factors, including the reaction temperature and the primer source and the application of the method. For example, the length of the oligonucleotide primer in diagnostic applications, according to the complexity of the target sequence, is between 5 to 100 nucleotides, preferably 6 to 40, and especially preferred 7 to 30 nucleotides. Short primer molecules generally require lower reaction temperatures to carry out their primer function in order to form sufficiently stable complexes with the template, or higher concentrations of other reaction components, for example DNA polymerases, so that primer template complexes formed can sufficiently be lengthened.

The primers used here are selected such that they are "substantially" complementary to the various strands of each specific sequence to be amplified. This means, that the primers have to be sufficiently complementary to hybridize with their respective strands and to initiate a primer extension reaction. Thus, for example the primer sequence does not have to reflect the exact sequence of the target sequence. For example, a non-complementary nucleotide fragment can be attached to the 5' end of the primer, wherein the remaining primer sequence is complementary to the strand. In another embodiment single non-complementary bases or longer non-complementary sequences can be inserted into a primer, provided that the primer sequence has a sufficiently large complementarity with the sequence of the strand to be amplified, in order to hybridize therewith and thus, generate a primer template complex capable for the synthesis of the extension product.

In the course of the enzymatic synthesis of a strand complementary to the template a primer extension product is generated that is completely complementary to the template strand.

Tm—Melting Temperature

The melting temperature of a complementary or partially complementary double strand is generally understood to be a measured value of a reaction temperature at which ca. half of the strands is present as a double strand and the other half is present as a single strand. The system (association and dissociation of strands) is in equilibrium.

Due to a number of factors that can affect the Tm of a double strand (e.g., sequence length, CG content of the sequence, buffer conditions, concentration of divalent metal cations, etc.) the Tm of a nucleic acid to be amplified is to be determined under the same conditions as the intended amplification reaction.

Because the measurable melting temperature depends on multiple reaction parameters, e.g., the respective buffer conditions and respective concentrations of the reaction partners, the melting temperature is meant to be a value that was measured in the same reaction buffer as the exponential amplification, at concentrations of both complementary components of a double strand of about 0.1 µmol/l to about 10 µmol/l, preferably in a concentration of about 0.3 µmol/l to ca. 3 µmol/l, preferably at ca. 1 µmol/l. The respective value of the melting temperature is a guide value that correlates with the stability of a corresponding double strand.

The deoxyribonucleoside triphosphates (dNTPs) dATP, dCTP, dGTP, and TTP (or dUTP, or dUTP/TTP mixture) are added to the synthesis mixture in adequate amounts. In one embodiment at least one further type of dNTP analogues can be added to the synthesis mixture in addition to the dNTPs. In one embodiment, these dNTP analogues comprise for example a characteristic mark (e.g., biotin or fluorescent dye), so that when built into a nucleic acid strand also this mark is integrated in the nucleic acid strand. In another embodiment, these dNTP analogues comprise at least one modification of the sugar phosphate proportion of the nucleotide, e.g., alpha-phosphorothioate-2'-deoxyribonucleoside triphosphates (or other modifications imparting a nuclease resistance to a nucleic acid strand), 2',3'-dideoxyribonucleoside triphosphates, acyclo-nucleoside triphosphates (or other modifications resulting in the termination of a synthesis). In a further embodiment, these dNTP analogues comprise at least one modification of a nucleobase, e.g., iso-cytosines, iso-guanosines (or also other modifications of the nucleobases of the extended genetic alphabet), 2-aminoadenosines, 2-thiouridines, inosines, 7-deaza-adenosines, 7-deaza-guanosines, 5-me-cytosines, 5-propyl-uridines, 5-propyl-cytosines (or also other modifications of nucleobases that can be built in by a polymerase compared to natural nucleobases and result in the change of the strand stability). In a further embodiment, a dNTP analogue comprises both a modification of the nucleobase and a modification of the sugar phosphate proportion. In a further embodiment, at least one further type of dNTP analogues is added to the synthesis mixture instead of the at least one natural dNTP substrate.

The agent inducing the nucleic acid synthesis can be an enzyme-entrapping compound or a system that acts such that as a result the synthesis of the primer extension product is caused. Suitable enzymes for this purpose comprise e.g., DNA polymerases such as Bst polymerase and its modifications, Vent polymerase and other—preferably thermostable DNA polymerases that enable the incorporation of the nucleotides in the correct manner, whereby the primer extension products are formed that are complementary to each synthesized nucleic acid strand. Generally, the synthesis is initiated on the 3' end of each primer and then progresses toward the 5' direction along the template strand until the synthesis is completed or interrupted.

Preferably, there are used polymerases that are capable of strand displacement. These include for example the large fragment of the Bst polymerase or its modifications (e.g., Bst 2.0 DNA polymerase), the Klenow fragment, Vent exo minus polymerase, Deepvent exo minus DNA polymerase, a large fragment of the Bsu DNA polymerase, a large fragment of the Bsm DNA polymerase.

In one embodiment, there are preferably employed polymerases that have no 5'-3'-exo-nuclease activity or no 5'-3'-FEN activity, respectively.

In one embodiment, at least two different polymerases are employed, for example polymerases capable of strand displacement and such that have a 3'-5'-proof reading activity.

In preferred embodiments, there are employed polymerases with a hot start function that only exert their function after having reached a certain temperature.

First Primer Oligonucleotide:

The first primer oligonucleotide (FIGS. 14 to 18) comprises a first primer region and a second region. The first primer region is able to bind to a substantially complementary sequence within the nucleic acid to be amplified or equivalents thereof and to initiate a primer extension reaction. The second region comprises a polynucleotide tail that is able to bind to an activator oligonucleotide and thus, to cause a spatial proximity between the activator oligonucleotide and other parts of the first primer extension product that is sufficient to initiate a strand displacement by the activator oligonucleotide. The second region of the first primer oligonucleotide further comprises at least one modification (a nucleotide modification or non-nucleotide modification) that prevents the polymerase from copying the polynucleotide tail by inhibiting the continuation of the polymerase-dependent synthesis. Said modification is located for example at the transition between the first and the second regions of the first primer oligonucleotide. Accordingly, the first primer region of the first primer oligonucleotide can be copied by a polymerase, so that a sequence complementary to this region can be generated by the polymerase during the synthesis of the second primer extension product. The polynucleotide tail of the second region of the first primer oligonucleotide is preferably not copied by the polymerase. In one embodiment, this is achieved by the modification in the second region that stops the polymerase before the polynucleotide tail. In a further embodiment, this is achieved by nucleotide modifications in the second region, wherein the entire polynucleotide tail substantially consists of such nucleotide modifications and thus, cannot be copied by polymerase.

In one embodiment, each first primer oligonucleotide is specific for one nucleic acid to be amplified each.

In one embodiment, each first primer oligonucleotide is specific for at least two of the nucleic acids to be amplified that each comprise substantially different sequences.

In one embodiment, the first primer oligonucleotide is labeled with a characteristic marker, e.g., a fluorescent dye (e.g., TAMRA, fluorescein, Cy3, Cy5) or an affinity marker (e.g., biotin, digoxigenin) or an additional sequence fragment, e.g., for binding a specific oligonucleotide probe for detection or immobilization or barcode labeling.

Second Primer Oligonucleotide:

Oligonucleotide that with its 3' segment is able to bind to a substantially complementary sequence within the nucleic acid to be amplified or equivalents thereof and to initiate a specific second primer extension reaction. Thus, this second primer oligonucleotide is able to bind to the 3' segment of a first specific primer extension product of the first primer oligonucleotide and to initiate a polymerase-dependent synthesis of a second primer extension product.

The length of the second primer oligonucleotide can be between 15 and 100 nucleotides, preferably between 20 and 60 nucleotides, particularly preferred between 30 and 50 nucleotides.

In one embodiment, each of the second primer oligonucleotides is specific for one nucleic acid to be amplified each.

In one embodiment, each of the second primer oligonucleotides is specific for at least two of the nucleic acids to be amplified that each comprise substantially different sequences.

In one embodiment, the second primer oligonucleotide is labeled with a characteristic marker, e.g., a fluorescent dye (e.g., TAMRA, fluorescein, Cy3, Cy5) or an affinity marker (e.g., biotin, digoxigenin) or an additional sequence fragment, e.g., for binding a specific oligonucleotide probe for detection or immobilization or barcode labeling.

Primer Extension Product:

A primer extension product (also referred to as primer elongation product) is generated by enzymatic (polymerase-dependent) extension of a primer oligonucleotide as a result of a template-dependent synthesis that is catalyzed by a polymerase.

A primer extension product comprises the sequence of the primer oligonucleotide in its 5' segment and the sequence of the extension product (also referred to as elongation product) that was synthesized by a polymerase in a template-dependent manner. The extension product synthesized by the polymerase is complementary to the template strand to which it was synthesized.

A specific primer extension product (FIGS. 21 to 24) (main product) comprises sequences of the nucleic acid chain to be amplified. It is the result of a specific synthesis or a proper performance of an intended primer extension reaction in which the nucleic acid chain specifically to be amplified serves as a template. In a preferred embodiment, the sequence of the synthesized primer extension products completely corresponds to the expected sequence of a nucleic acid to be amplified. In another embodiment, divergences in the obtained sequence from the theoretically expected sequence can be tolerated. In one embodiment, the degree of matching of the sequence obtained as a result of an amplification with the sequence of the theoretically expected nucleic acid to be amplified is for example between 90% and 100%, preferably the matching is above 95%, ideally the matching is above 98% (based on the proportion of the synthesized bases).

The length of the extension product of a specific primer extension product can be between 10 and 300 nucleotides, better between 10 and 180 nucleotides, preferably between 20 and 120 nucleotides, particularly preferably between 30 and 80 nucleotides.

A non-specific primer extension product (by-product) comprises for example sequences that have been generated as a result of a non-specific or incorrect or unintended primer extension reaction. These include for example primer extension products that have been generated as a result of a false initiation result (false priming) or as a result of other side reactions, including polymerase-dependent sequence changes such as base substitution, deletion etc. The degree of sequence divergences of non-specific primer extension products generally exceeds the ability of activator oligonucleotides to successfully displace such double-stranded by-products from their templates, so that amplification of such by-products proceeds slower or is completely absent. The degree of acceptance or the limit of tolerance for divergences for example depends on reaction temperatures and the type of sequence divergence. Examples of non-specific primer extension products are primer dimers or sequence variants that do not correspond to the nucleic acid to be amplified, e.g., sequences that do not comprise a target sequence.

Assessment as to a sufficient specificity of the amplification is often linked to the problem formulation. In many amplification methods a certain degree of non-specificity of the amplification reaction can be tolerated as long as the desired result can be obtained. In a preferred embodiment, the proportion of nucleic acid chains to be amplified in the total result of the reaction is more than 1%, better more than 10%, more preferably more than 30%, based on the total amount of re-synthesized strands.

Nucleic Acid to be Amplified

The nucleic acid to be amplified is a nucleic acid chain that is to be sequence-specifically or at least mainly sequence-specifically amplified by the polymerase by means of the exponential amplification by employing primers and activator oligonucleotides.

The length of the nucleic acid to be amplified can be between 20 and 300 nucleotides, better between 30 and 200 nucleotides, preferably between 40 and 150 nucleotides, particularly preferred between 50 and 100 nucleotides.

The nucleic acid chain to be amplified can comprise one or more target sequences or equivalents thereof. Furthermore, a nucleic acid to be amplified can comprise the sequences that are substantially complementary to a target sequence and that are multiplied with a similar efficacy such as a target sequence in an amplification reaction and comprises a target sequence or sections thereof. In addition to a target sequence the nucleic acid to be amplified can further include sequence segments, for example primer sequences, sequences with primer binding sites and/or sequence segments for binding detection probes, and/or sequence segments for sequence coding of strands by barcode sequences and/or sequence segments for binding to a solid phase. The primer sequences or sequence portions thereof as well as primer binding sites or sequence portions thereof may for example belong to sequence parts of a target sequence.

In one embodiment, the nucleic acid to be amplified corresponds to a target sequence.

In another embodiment, the target sequence forms a part of the sequence of the nucleic acid chain to be amplified. Such a target sequence can be flanked by the 3' side and/or 5' side of further sequences. These further sequences can for example comprise binding sites for primers or portions thereof, and/or primer sequences or portions thereof, and/or binding sites for detection probes, and/or adaptor sequences for complementary binding to a solid phase (e.g., in the context of microarrays, or bead-based analyses) and/or barcoding sequences for a digital signature of sequences.

To start the amplification a nucleic acid chain has to be added to the reaction mixture at the beginning of the reaction that acts as the initial template for the synthesis of the nucleic acid chain to be amplified. Said nucleic acid chain is referred to as the start nucleic acid chain.

Said start nucleic acid chain prescribes the arrangement of individual sequence elements that are relevant for the formation/synthesis/exponential amplification of a nucleic acid chain to be amplified.

In a preferred embodiment, the initial template (start nucleic acid chain), that is added to an amplification reaction at the beginning or is added to the reaction mixture, corresponds to the sequence composition of the nucleic acid chain to be amplified.

In initial stages of the amplification reaction and in its further course the respective primers bind to the corresponding binding sites in the start nucleic acid chain and initiate the synthesis of specific primer extension products. Such specific primer extension products during the amplification exponentially accumulate and increasingly take the role of templates for the synthesis of complementary primer extension products in an exponential amplification.

By the repeated template-dependent synthesis processes during an exponential amplification there is formed thus the nucleic acid chain to be amplified.

Toward the end of an amplification reaction the main product of the reaction (the nucleic acid to be amplified) can mainly be single-stranded or mainly form a complementary double strand. This can for example be determined by the relative concentrations of both primers and the appropriate reaction conditions.

Equivalents of the nucleic acid to be amplified comprise nucleic acids of substantially identical information content. For example, complementary strands of a nucleic acid to be amplified have an identical information content and may be referred to as being equivalent.

Target Sequence

In one embodiment, a target sequence is a segment of a nucleic acid chain to be amplified that can serve as the characteristic sequence of the nucleic acid to be amplified. Said target sequence can serve as a marker for the presence or absence of another nucleic acid. Thus, said other nucleic acid serves as a source of the target sequence and for example can comprise a genomic DNA or RNA or parts of the genomic DNA or RNA (e.g., mRNA), or equivalents of the genomic DNA or RNA of an organism (e.g., cDNA, modified RNA such as rRNA, tRNA, microRNA etc.), or defined changes of the genomic DNA or RNA of an organism, for example mutations (e.g., deletions, insertions, substitutions, additions, sequence multiplication, e.g., repeat multiplication in context of microsatellite instability), splice variants, rearrangement variants (e.g., T cell receptor variants) etc. The individual target sequences may stand for a phenotypic feature, for example for antibiotic resistance or have prognostic information and thus, be of interest for diagnostic assays/tests. As the source/origin for a target sequence such a nucleic acid can for example comprise the target sequence as a sequence element of its strand. Thus, a target sequence can serve as a characteristic marker for a certain sequence content of another nucleic acid.

The target sequence can be single-stranded or double-stranded. It can be substantially identical to the nucleic acid to be amplified or only represent a part of the nucleic acid to be amplified.

Equivalents of the target sequence comprise nucleic acids of substantially identical information content. For example, complementary strands of a target sequence have an identical information content and can be referred to as being equivalent. Also, RNA and DNA variants of a sequence are examples of an equivalent information content.

In context of the material preparation for an amplification reaction such a target sequence can be isolated from its original sequence environment and prepared for the amplification reaction.

In a preferred embodiment, a nucleic acid to be amplified comprises a target sequence. In one embodiment, the target sequence corresponds to the nucleic acid to be amplified. In a further preferred embodiment, a start nucleic acid chain comprises a target sequence. In one embodiment, the target sequence corresponds to a start nucleic acid chain.

Start Nucleic Acid Chain

To start the amplification a nucleic acid chain has to be added to the reaction mixture at the beginning of the reaction that acts as the initial template for the synthesis of the nucleic acid chain to be amplified (FIGS. 1 and 7). Said nucleic acid chain is referred to as the start nucleic acid chain. Said start nucleic acid chain prescribes the arrangement of individual sequence elements that are relevant for the formation/synthesis/exponential amplification of a nucleic acid chain to be amplified.

Such a start nucleic acid chain can be single-stranded or double-stranded at the beginning of the reaction. If the complementary strands of the start nucleic acid chain are separated from each other at the beginning, regardless of whether the nucleic acid originally was double- or single-stranded, can serve as a template for the synthesis of specific complementary primer extension products.

Activator Oligonucleotide:

The activator oligonucleotide (FIG. 19) is a preferably single-stranded nucleic acid chain that includes a pre-defined substantially complementary sequence in a part of the first primer extension product that is specifically generated during the amplification of the nucleic acid to be amplified. In this way, the activator oligonucleotide can substantially complementary bind to the first primer oligonucleotide and at least to the 5' segment of the specific extension product of the first primer oligonucleotide. In one embodiment, the activator oligonucleotide in its inner sequence segment comprises nucleotide modifications that prevent polymerase from synthesizing a complementary strand using the activator oligonucleotide as a template if the first primer oligonucleotide is complementary bound to the activator oligonucleotide. The activator oligonucleotide under the chosen reaction conditions is further able to completely or partially displace the second specific primer extension product from the binding with the first specific primer extension product via strand displacement. Here, the activator oligonucleotide with its complementary regions is attached to the first specific primer extension product. In case of a successful binding between the activator oligonucleotide and the first specific primer extension product this results in a restoration of a single-stranded stage of the 3'-standing segment of the second specific primer extension product that is suitable for the binding of the first primer oligonucleotide, so that a new primer extension reaction can take place. During the synthesis of the second primer extension product the activator oligonucleotide can be separated from the binding with the first primer extension product by means of strand displacement, for example by polymerase and/or by the second primer oligonucleotide.

Detection System

A detection system comprises at least one oligonucleotide probe and at least one fluorescence reporter (a fluorophore). The detection system shall be able to detect the synthesis of the first primer extension product. This takes place by using oligonucleotides that are able to bind to the primer extension product and thereby generate a specific signal and cause a change in the signal, respectively. Here, said change may be an increase or decrease of the fluorescence intensity. Further, a detection system can comprise additional components. Such components preferably are fluorescence quenchers and/or donor fluorophores. Moreover, the detection system can also comprise the activator oligonucleotide. The arrangement of fluorescence reporter, fluorescence quencher, donor fluorophore on the oligonucleotide probe or on the pair comprising oligonucleotide probe and activator oligonucleotide makes it possible to detect the binding events to the first primer extension product.

Fluorescence Reporter—a fluorophore is a chemical compound or a molecule, respectively, which, when excited with electromagnetic radiation, is able to emit an electromagnetic radiation (light) (emission). Said radiation emitted by the fluorophore (emission) can be detected as a fluorescence signal with suitable technical means. Such a reporter can be covalently bound to an oligonucleotide. There are known many fluorophores that can be coupled to oligonucleotides (e.g. FAM, TAMRA, HEX, ROX, Cy dyes, Alexa dyes)

Fluorescence Quencher—a quencher is a chemical compound/a molecule that by direct contact (contact quenching) or by energy transfer (e.g. as FRET) is able to reduce the emission of a fluorophore. Generally, a quencher has to be brought into close proximity to the fluorophore in order that said signal reduction can take place to the significant extent.

Of advantage for a significant signal reduction of a fluorescence reporter by a quencher are distances between the reporter and quencher of less than 25 nucleotides, better less than 15 nucleotides, particularly advantageous less than 5 nucleotides.

To overcome a signal reduction of a fluorescence reporter by a quencher, the distance between these components has correspondingly to be increased, here it is of advantage if the distance between the reporter and quencher is increased to more than 15 nucleotides, better to more than 20 nucleotides, particularly advantageous to more than 40 nucleotides.

In this case, the distance effected by the nucleotide sequence has to be attributed to an extended nucleotide sequence. For example, when hairpin structures are formed, the spatial distance is possibly no longer given.

Especially, with FRET-based quenchers a sufficient spectral overlapping between the emission spectrum of a fluorophore and the absorption spectrum of a quencher is of advantage. Hence, fluorophore-quencher pairs preferably will have more than 25% spectral overlappings (e.g. FAM/TAMRA).

Donor Fluorophores—are chemical compounds/molecules that are able to absorb electromagnetic radiation and transfer it to another fluorophore (acceptor) by energy transfer (e.g. as FRET) such that said fluorophore is excited and as a result generates light emission by itself. Upon emission a fluorescence signal is generated. Generally, donor and acceptor form a fluorescence resonance energy transfer pair (a FRET pair). Generally, a donor has to be brought into close proximity to the acceptor (fluorophore) in order that this signal generation can take place to the significant extent.

Of advantage for signal generation of a fluorescence reporter as a result of a FRET of a donor fluorophore are distances between the reporter and donor of less than 25 nucleotides, better less than 15 nucleotides, particularly advantageous less than 5 nucleotides.

Cancellation of the FRET effect from the donor to the acceptor is generally achieved by an increase in the distance between both members of a FRET pair. Here, it is of advantage if the distance between the reporter and donor is increased to more than 15 nucleotides, better to more than 20 nucleotides, particularly advantageous to more than 40 nucleotides.

In addition, generally a sufficient spectral overlapping between the emission spectrum of a donor and the absorption spectrum of an acceptor is of advantage. Hence, there are preferred FRET pairs that have more than 25% spectral overlapping (e.g. FAM/Cy3).

According to the invention, spatial distance between the individual components is preferably effected in that two components are connected via one nucleotide sequence that can hybridize with a certain part of the target sequence.

Strand Displacement:

This refers to a process that by action of a suitable means results in a complete or partial separation of a first double strand (for example consisting of A1 and B1 strands) and in simultaneous/parallel formation of a new second double strand, wherein at least one of the strands (A1 or B1) takes part in the formation of said new second strand. Here, distinctions can be made between two types of strand displacement.

In a first type of the strand displacement formation of a new second double strand can be by using an already existing complementary strand that at the beginning of the reaction is generally present as a single-stranded form. Here, the means of the strand displacement (for example, a pre-formed single-stranded strand C1 that has a complementary sequence to strand A1, acts on the first already formed double strand (A1 and B1) and complementary binds to strand A1, whereby strand B1 is displaced from the binding with strand A1. If the displacement of B1 proceeds completely, so the result of the C1 action is a new double strand (A1:C1) and a single-stranded strand B1. If the displacement of B1 proceeds incomplete, so the result depends on several factors. For example, a complex of partially double-stranded A1:B1 and A1:C1 can be present as an intermediate product.

In a second type of the strand displacement the formation of a new second double strand can be with a simultaneously proceeding enzymatic synthesis of the complementary strand, wherein a strand of the first pre-formed double strand is present as a template for the synthesis by the polymerase. Here, the means of the strand displacement (for example, polymerase having a strand displacement ability) acts on the already pre-formed double strand (A1 and B1) and synthesizes a new strand D1 complementary to strand A1, wherein at the same time strand B1 is displaced from the binding with strand A1.

Under the term "nucleic acid-mediated strand displacement" a sum/series of intermediate steps is brought together that can be in equilibrium with each other and as a result lead to the transient or permanent opening of a first pre-formed duplex (consisting of complementary strands A1 and B1) and formation of a new second duplex (consisting of complementary strands A1 and C1), wherein A1 and C1 are complementary.

It is known that an essential structural requirement for the initiation of a strand displacement is to cause a spatial proximity between a duplex end (pre-formed first duplex of A1 and B1) and a single-stranded strand (C1) that initiates the strand displacement (wherein A1 and C1 can form a complementary strand). Such a spatial proximity can preferably be caused by means of a single-stranded overhang (in the literature examples with short overhangs are known, in English referred to as "toehold", see literature above) that complementary binds the single-stranded strand (C1) transiently or permanently, and thus brings complementary segments of strands C1 and A1 sufficiently close, so that a successful strand displacement of strand B1 can be initiated. Efficacy of the initiation of the nucleic acid-mediated strand displacement generally is the higher the closer the complementary segments of strands A1 and C1 are positioned to each other.

A further essential structural requirement of the efficient continuation of a nucleic acid-mediated strand displacement in inner segments is a high complementarity between strands (e.g., between A1 and C1) that have to form a new double strand. So, for example individual nucleotide mutations (in C) can result in the disruption of a strand displacement (e.g., described for branch migration).

The present invention uses the ability of complementary nucleic acids for sequence-dependent nucleic acid-mediated strand displacement.

Preferred embodiments of the invention are explained in detail in the figures and examples.

FIG. 1A schematically shows components of the amplification system in the batch before the start of the amplification:

Start nucleic acid (start na) comprising a target sequence.

Primer 1 (P1.1), primer 2 (P2.1), an activator oligonucleotide (C1.1).

Components for primer extension products: polymerase (Pol) and dNTPs

FIG. 1B schematically shows the result of the amplification:

Primer extension product P1.1-Ext starting from P1.1, primer extension product 2.1-Ext. These products (P1.1-Ext, P2.1-Ext) among themselves and with the activator oligonucleotide can form different complex forms (depending on the concentration ratio and reaction conditions). In detail, these forms can comprise complexes from P1.1-Ext/C1.1 and/or P1.1-Ext and/or P1.1-Ext/C1.1/P2.1-Ext.

P1-Ext comprises a 3' segment that is not complementary bound by the activator oligonucleotide. Said segment acts as a binding partner for the oligonucleotide probe.

FIG. 2A schematically shows components of a detection system:

An oligonucleotide probe (S1.1) is an oligonucleotide which comprises a fluorescence reporter (R) and a quencher (Q). In the primarily single-stranded state where the probe is not bound to the complementary sequence the reporter and the quencher are spatially not sufficiently separated so that the fluorescence signal is reduced by the reporter by the quencher. In case of a primarily complementary binding to the 3' segment of a P1-Ext, quencher and reporter are spatially separated so that the fluorescence signal is increased.

FIG. 2B schematically shows components of a detection system:

An oligonucleotide probe (S2.1) is an oligonucleotide which comprises a fluorescence reporter (R) and a quencher (Q). The probe comprises self-complementary sequence elements (stem segment 1 and stem segment 2) which are separated from one another by a loop segment 3. In case of a complementary binding of the "loop segment" 3 to a sequence portion of the 3' segment of a P1-Ext, quencher and reporter are spatially separated under the used reaction conditions of the detection step which results in an increase of the fluorescence signal.

FIG. 3A schematically shows components of a detection system:

An oligonucleotide probe (S3.1) is an oligonucleotide which comprises a reporter and a quencher. The probe comprises self-complementary sequence elements (stem segment 1 and stem segment 2) which are separated from one another by a loop segment 3. In case of a simultaneous primarily complementary binding of the stem segment 1 and the sequence segment 4 to the 3' segment of a P1-Ext, quencher and reporter are spatially separated under the reaction conditions of the detection step which results in an increase of the fluorescence signal.

FIG. 3B schematically shows components of a detection system:

An oligonucleotide probe (S4.1) is an oligonucleotide which comprises a reporter and a quencher. The probe comprises self-complementary sequence elements (stem segment 1 and stem segment 2) which are separated from one another by a loop segment 3. The probe comprises a further sequence segment 4 that can form a complementary strand with the 3' segment of the P1-Ext and can be extended as a primer of polymerase. Upon extension by the polymerase a primer extension product S4.1-Ext is formed.

FIGS. 4A and 4B schematically show components of a further detection system:

An oligonucleotide probe (S5.1) and at least one activator oligonucleotide (A5.1), a FRET pair, donor and reporter each are separately coupled on one of the two oligonucleotides and arranged such that in case of a complementary binding of both oligonucleotides to the same P1-Ext the donor and the reporter are in a spatial proximity so that the reporter can be excited by the donor.

FIGS. 5A and 5B schematically show components of a further detection system:

An oligonucleotide probe (S7.1 and S8.1, respectively) and at least one activator oligonucleotide (A7.1 and A8.1, respectively), and a FRET pair. The oligonucleotide S7.1 or S8.1 in case of a complementary binding to the P1-Ext can be extended by a polymerase by displacing the activator oligonucleotide, so that in this way an S7.1 extension product (S7.1-Ext) or S8.1 extension product (S8.1-Ext) are generated.

FIG. 6 schematically shows binding positions of the oligonucleotide probe at the first primer extension product.

FIGS. 7 to 10 schematically show the interaction of components in an exponential amplification of a nucleic acid chain to be amplified.

FIGS. 14-18 schematically show the structure of the first primer oligonucleotide.

Figure 16:
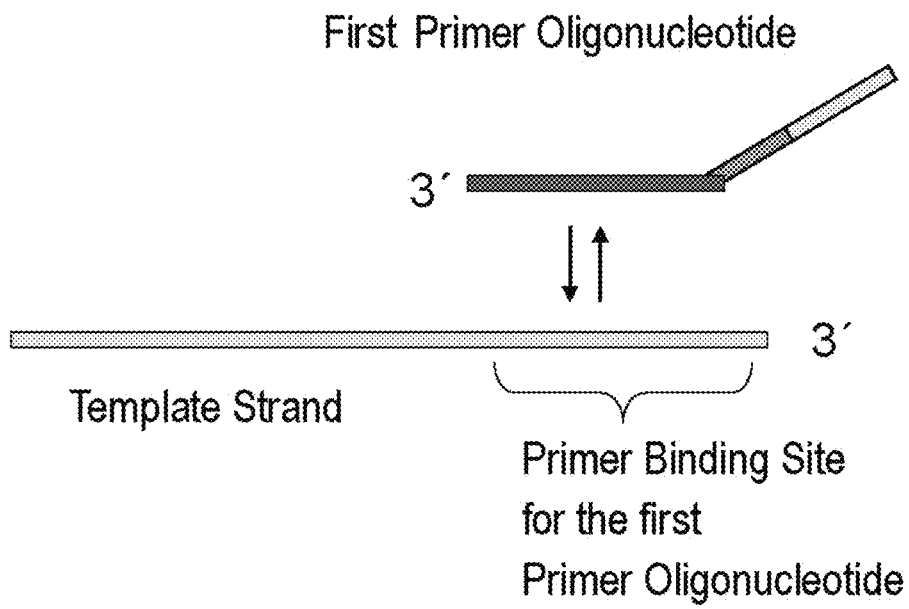

FIGS. 16-17 schematically show the interaction between the first primer oligonucleotide and the template as well as the synthesis of the first primer extension product.

Figure 18:
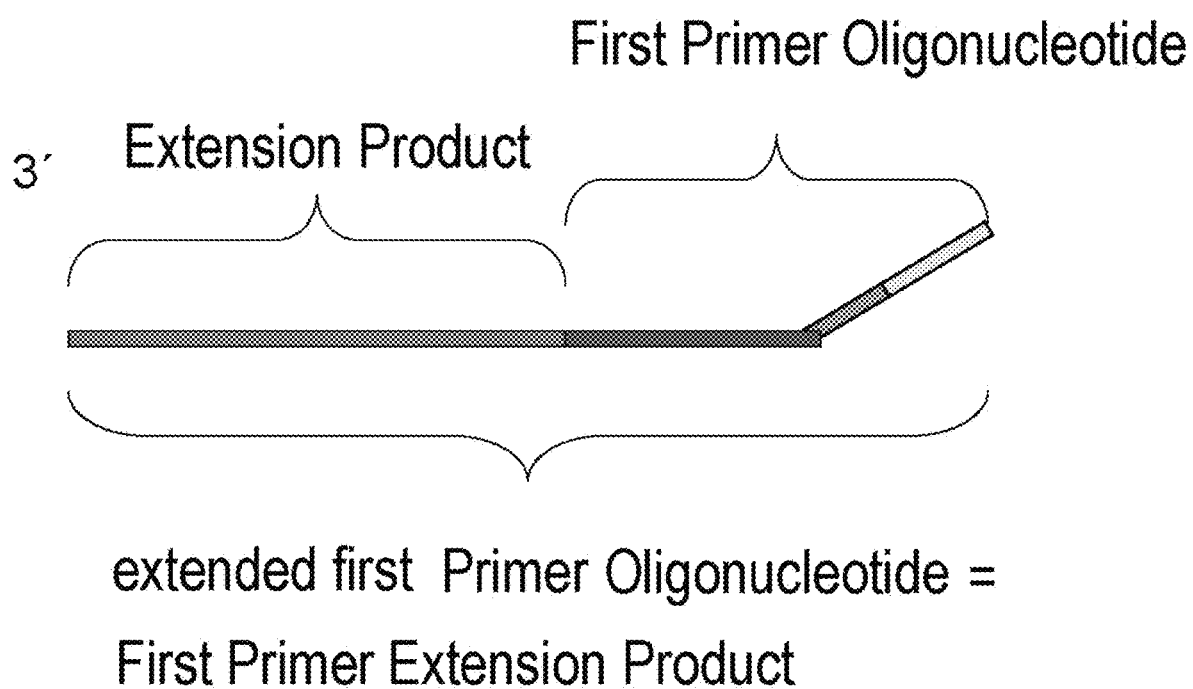

FIG. 18 schematically shows the structure of the primer extension product of the first primer oligonucleotide.

FIG. 19 schematically shows the structure of the activator oligonucleotide.

Figure 20:
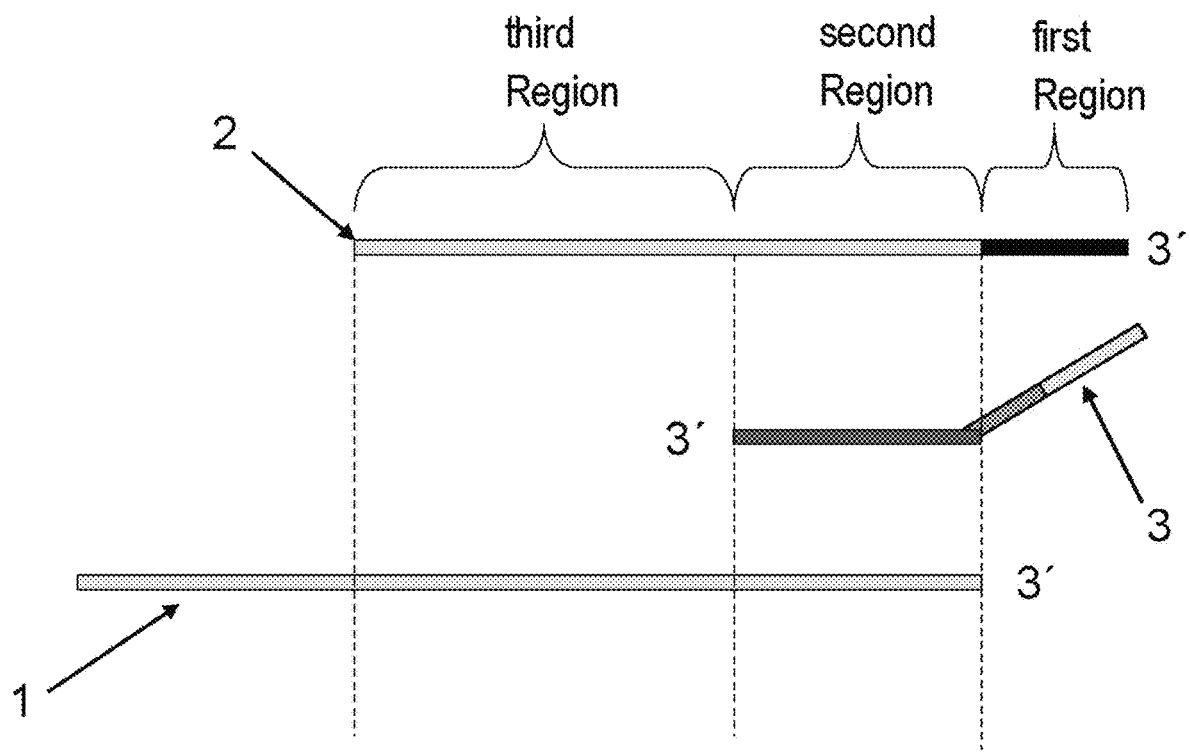
Figure 21:
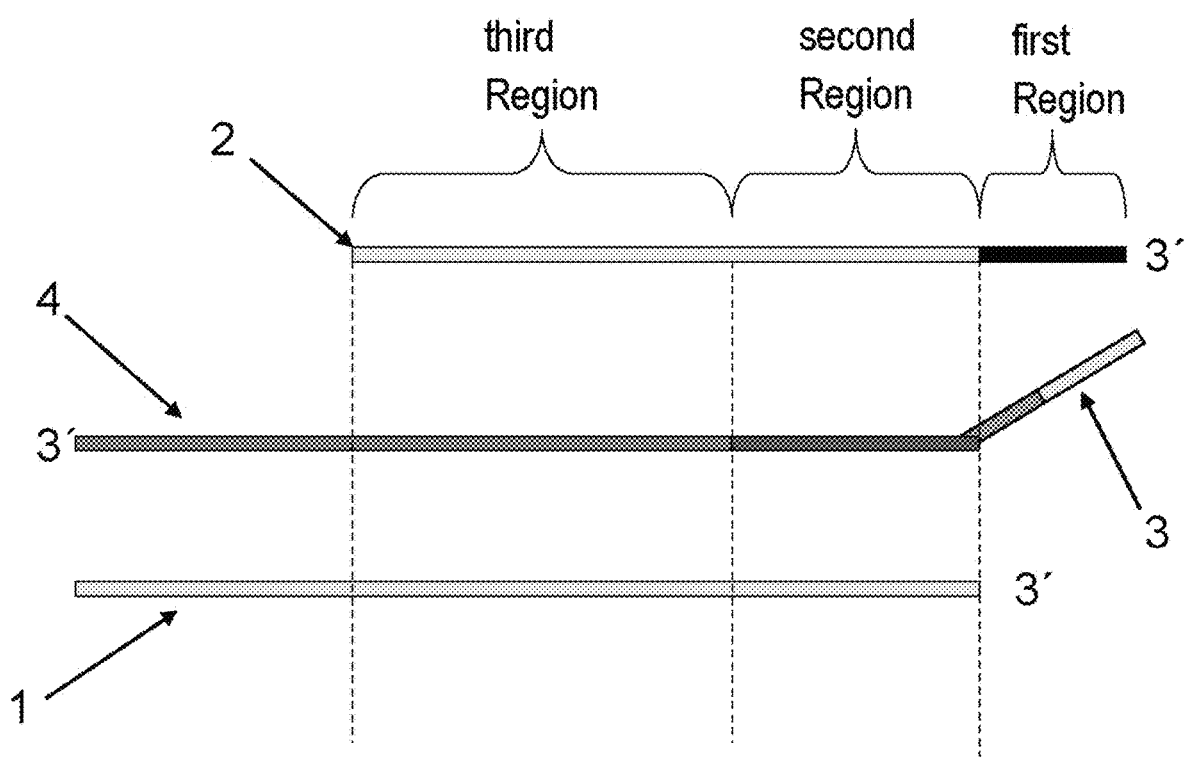
Figure 22:
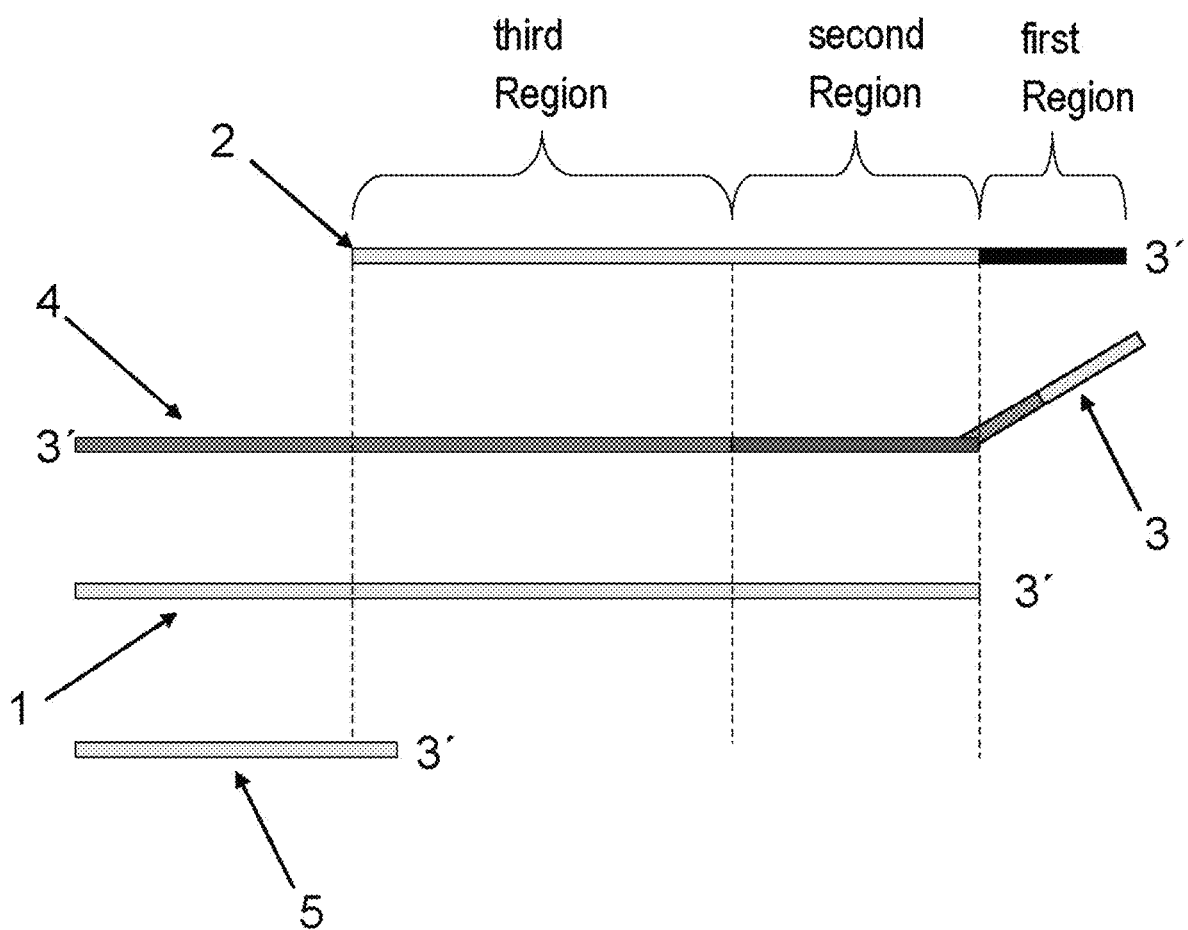
Figure 23:
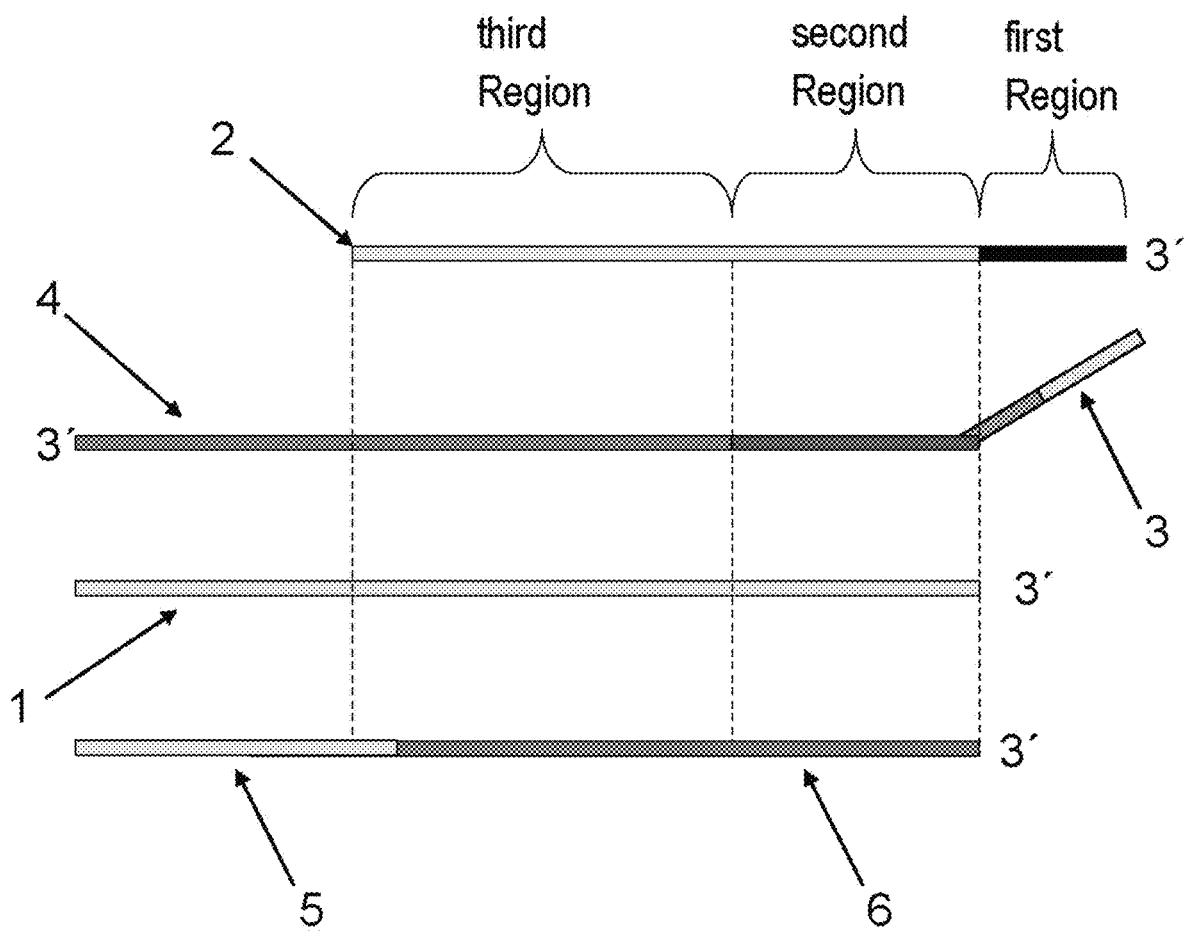

FIGS. 20-21 schematically show the interaction between structures during the primer extension of the first primer oligonucleotide.

FIGS. 22-25 schematically show the interaction between structures during the primer extension of the second primer oligonucleotide.

FIGS. 26-32 schematically show the interaction between individual regions of components during the amplification.

Figure 34:
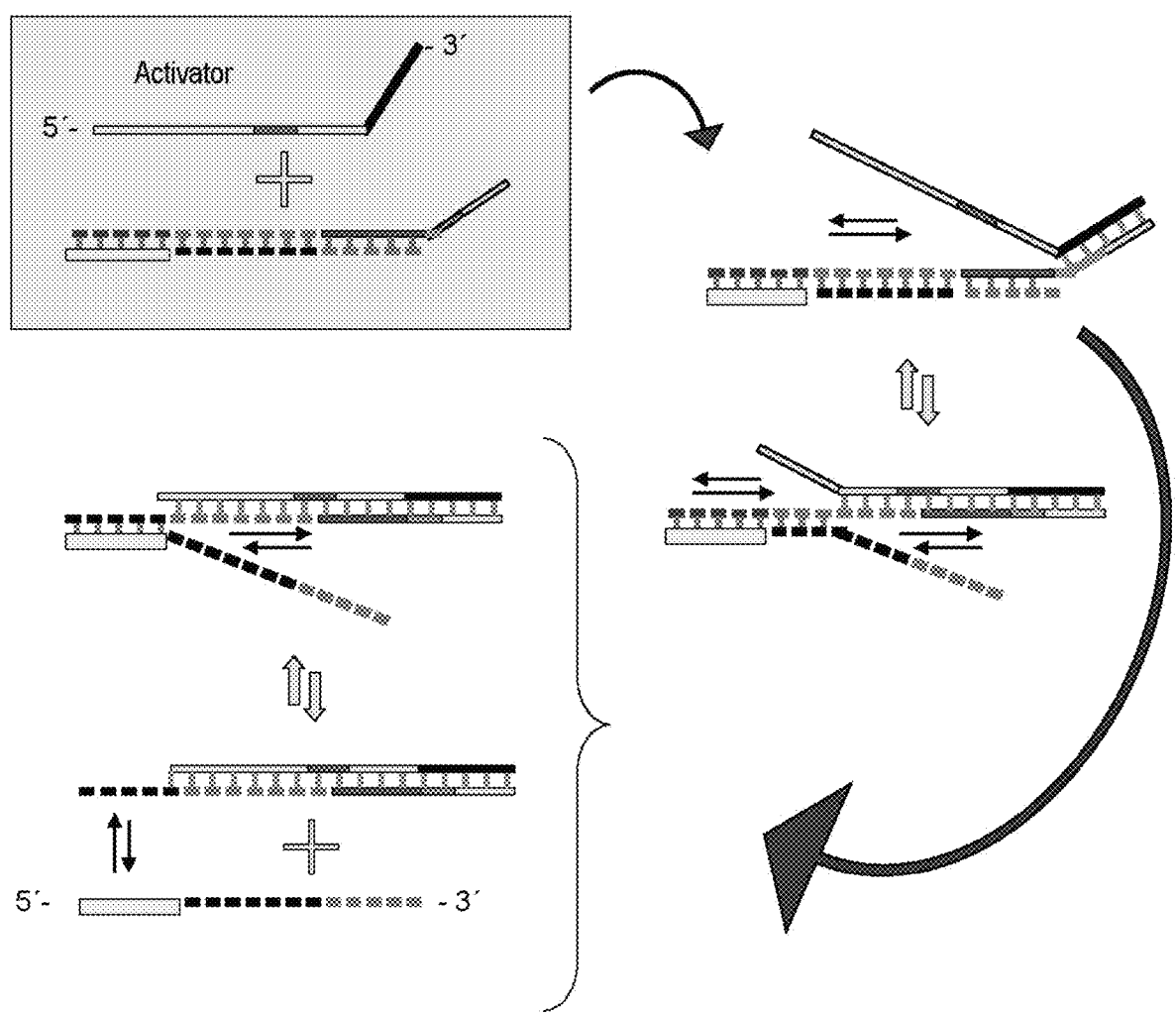
Figure 35:
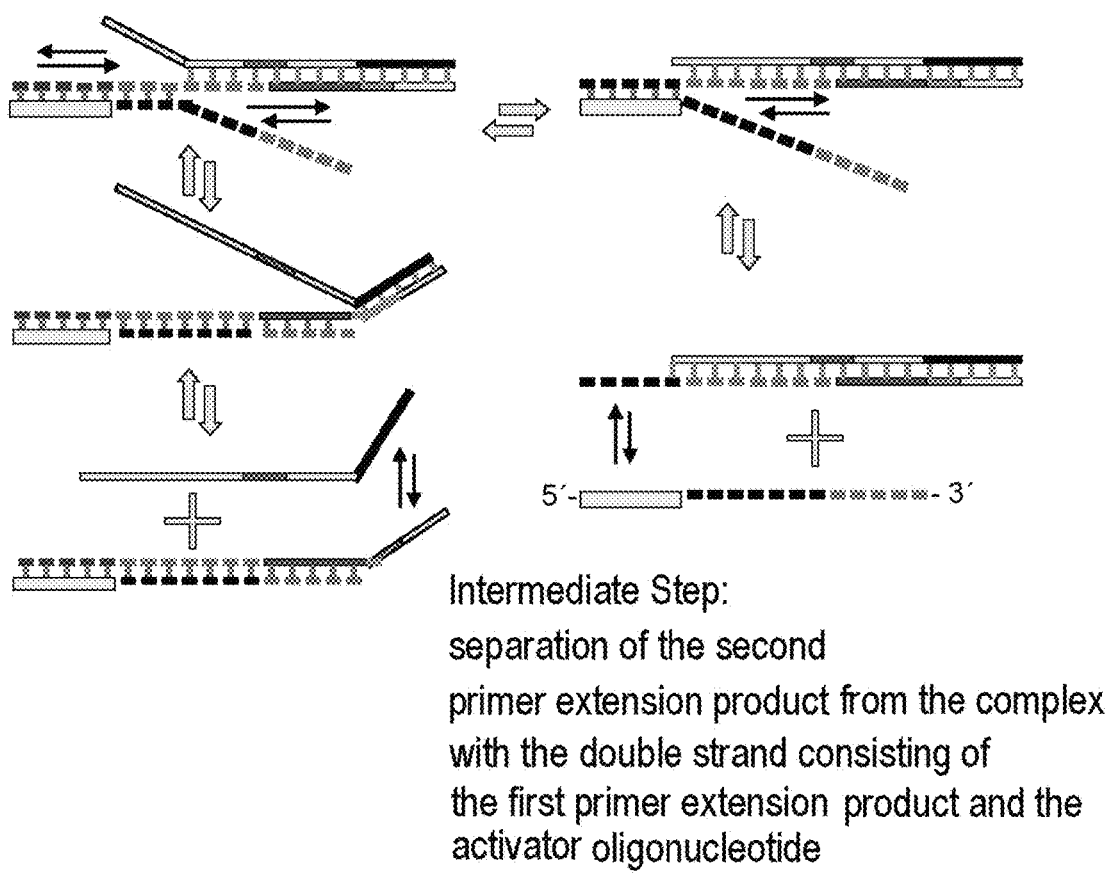
Figure 36:
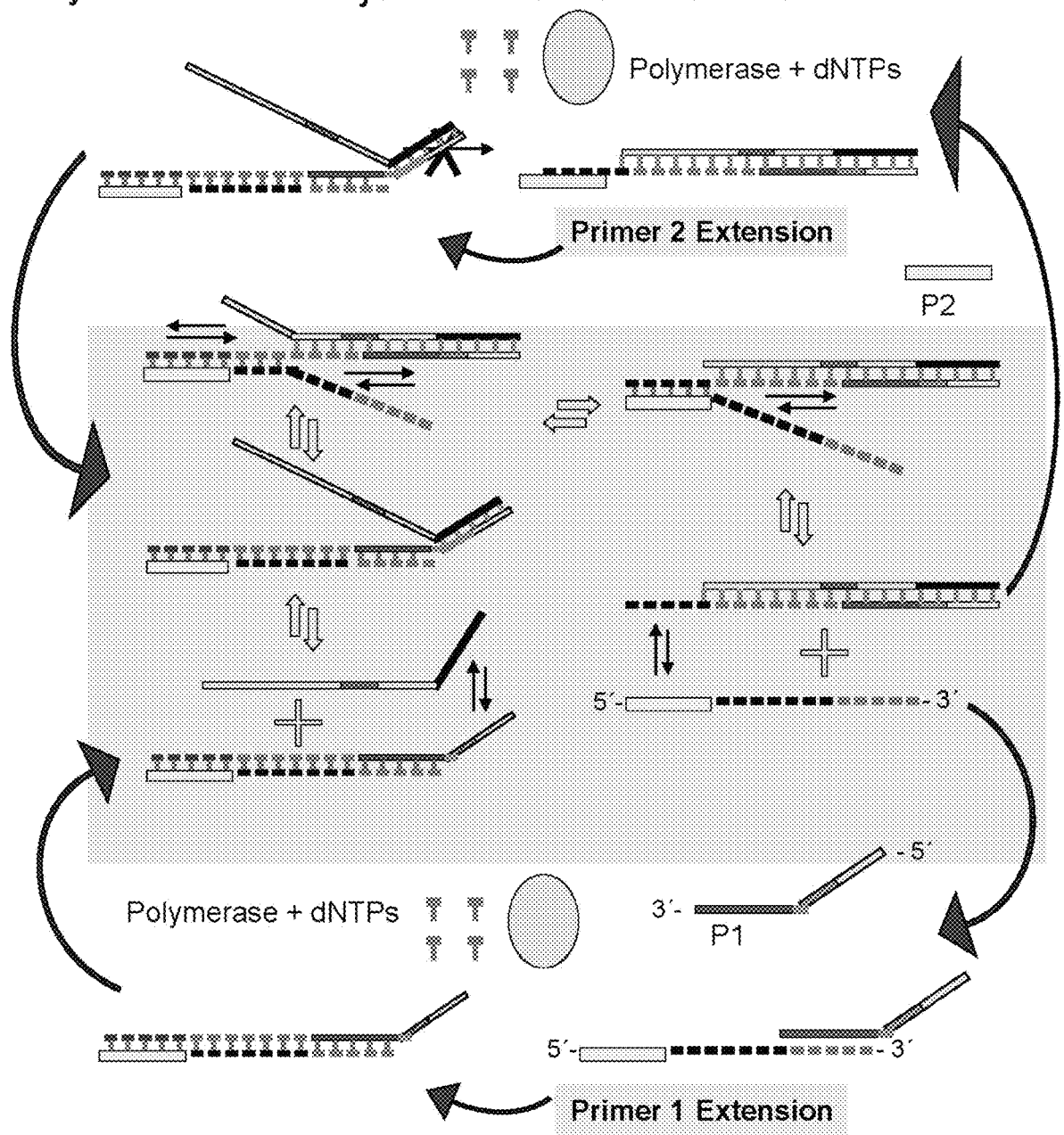

FIG. 33 describes the components of the structures illustrated in FIGS. 34-36 in more detail.

FIG. 34 schematically shows the strand displacement mechanism.

FIG. 35 schematically shows the interaction of the structures in strand displacement.

FIG. 36 schematically shows the interaction of the structures during nucleic acid amplification by amplification of the first primer oligonucleotide and the second primer oligonucleotide and further the effect of the activator oligonucleotide and the resulting strand displacement.

In the method (FIGS. 7 to 10) according to the invention a single-stranded nucleic acid chain or a double-stranded nucleic acid that was converted into the single-stranded form can serve as a starting material. The amplification preferably is sequence-specific, i.e. preferably the nucleic acid to be amplified is multiplied.

A nucleic acid chain to be amplified, a first specific primer oligonucleotide, a second primer, and an activator oligonucleotide that takes part in the separation of the re-synthesized strands as well as a suitable polymerase and substrates such as dNTPs serve as components of the amplification system. The amplification takes place in a buffer solution under conditions that allow a primer extension reaction of both primers as well as support a strand displacement by the activator oligonucleotide for the separation of both primer extension products.

In one embodiment, all the method steps are performed under conditions that do not allow a separation of synthesized primer extension products in the absence of a suitable activator oligonucleotide. For example, the temperature of the reaction solution is selected such that the Tm of a double strand of both primer extension products is significantly above the reaction temperature.

Under these conditions a separation of both primer extension products takes places depending on the effect of the activator oligonucleotide. Said activator oligonucleotide is able to complementary bind to the first primer extension product and thereby displace the second primer extension product from its binding with the first primer extension product. In order to initiate said strand displacement reaction the first primer oligonucleotide is provided with a polynucleotide tail in its second region that can transiently bind to the activator oligonucleotide under reaction conditions and thus, causes a spatial proximity to other regions of the first primer extension nucleotide. After the initiation of the strand displacement by the activator oligonucleotide the second primer extension product is displaced from its binding with the first primer extension product. So, its 3'-standing segment becomes free and is available for further binding of a first primer oligonucleotide.

The polynucleotide tail of the first primer oligonucleotide preferably cannot be copied by a polymerase. This can be achieved either by using appropriate modifications in this region or by inserting a first blocking unit between the first primer region and the second primer region of the first primer oligonucleotide.

The synthesis of the second primer extension product takes place after the second primer oligonucleotide has been bound to the first primer extension product in its 3'-standing segment. Said segment preferably does not bind to the activator oligonucleotide and is sufficiently long to bind the second primer oligonucleotide and support a successful primer extension reaction. The synthesis of the second primer extension product takes place by displacing the activator oligonucleotide from the binding with the first primer extension product. For example, this can be done by polymerase-dependent strand displacement or also by strand displacement by means of the second primer.

Both primer extension products include copyable regions and mutually serve as a template. The activator oligonucleotide does not serve as a template. This can preferably be achieved by the use of nucleotide modifications that certainly can complementary bind to the first primer extension product, but are not accepted as a template by the polymerase. Examples of such nucleotide modifications are nucleotide compounds having modified phosphate sugar backbone portions, e.g., 2'-O-Alkyl-RNA modifications (e.g., 2'-OMe), LNA modifications, or morpholino modifications. In general, the presence of such modifications in a strand prevents a DNA-dependent polymerase from reading such a strand. The number of such modifications can be different, generally a few modifications (between 1 and 20) may be sufficient in order to prevent a polymerase from reading such a strand. Such nucleotide modifications can for example be used at or around the site of binding of the first primer oligonucleotide to the activator oligonucleotide and/ or as constituents of the second region of the first primer oligonucleotide.

Owing to the use of such modifications the polymerase function is locally hindered, so that certain segments of the structures used cannot be copied by the polymerase and mainly remain single-stranded. In this single-stranded form they can further bind reaction components and thus, exercise their function.

Under reaction conditions that do not denature a double strand the use of the sequence-dependent nucleic acid-mediated strand displacement results in the sequence-specific separation of both primer extension products during the amplification reaction in the described method: a sufficient complementarity between re-synthesized extension fragments of the primer oligonucleotides with the sequence of an activator oligonucleotide given at the beginning of an amplification is a prerequisite for a successful strand displacement and thus, can have influence on the efficacy of the strand separation of a double strand (consisting of the first and second primer extension products). In case of minor divergences strand displacement and thus, also strand separation are decelerated. This can cause a deceleration of the entire reaction. With an increase in the difference in the sequence of the re-synthesized extension products and the sequence of the activator oligonucleotide given at the beginning of the reaction there is an increasing disability of the strand displacement that ultimately is no longer able to bring about a sufficient separation of both primer extension products. Both re-synthesized strands can no longer sufficiently be separated from each other, so that their binding sites are no longer accessible for primer oligonucleotides. In general, this leads to the termination of an amplification of sequences having sequence divergences.

In summary, not only the specificities of the binding of both primers with their templates, but also the nature of the sequence segments between the primers can have influence on the amplification, namely in that these sections allow a sufficient strand displacement or not, in accordance with their matching in the sequence of the activator oligonucleotide given at the beginning of the reaction. Thereby, the described method possibly overall can have a higher specificity than the conventional amplification methods.

The specific amplification further results by using the components at reaction conditions that preferably do not allow a spontaneous separation of re-synthesized primer extension products.

The method comprises several processes that are described below. These processes can be performed in one batch or in separate batches. If the processes are to be performed in one batch, so they can be performed under the same conditions, e.g., isothermal, or under different conditions, e.g., in thermocycling. Preferably, primer oligonucleotides and the activator oligonucleotide are present at the beginning of the reaction. However, a sequential addition of individual reagents is also possible.

Also, combinations with other amplification methods are possible, e.g., with PCR, wherein the PCR for example first is performed over 1 to 10 cycles and subsequently, it is for example went on working under isothermal conditions.

In an advantageous embodiment, the method for monitoring/detection of a specific amplification of nucleic acid chains comprises the following steps (aspect 1): Realization of an amplification of a nucleic acid chain to be amplified, which comprises the following steps:

a) hybridizing a first primer oligonucleotide to the 3' segment of a strand of a nucleic acid chain to be amplified, wherein the nucleic acid chain to be amplified comprises a target sequence, wherein the first primer oligonucleotide comprises:
- a first primer region in the 3' segment of the first primer oligonucleotide that can sequence-specifically bind to a strand of a nucleic acid chain to be amplified,
- a second region that is directly or via a linker linked to the 5' end of the first primer region of the first primer oligonucleotide and that comprises a polynucleotide tail which is suitable for binding an activator oligonucleotide and supporting strand displacement (step c) by the activator oligonucleotide, wherein the polynucleotide tail remains substantially uncopied by polymerase under the selected reaction conditions, b) extending the first primer oligonucleotide by means of a polymerase to form a first primer extension product comprising sequence parts that are complementary to the target sequence and/or to the nucleic acid chain (a) to be amplified, c) binding the activator oligonucleotide to the polynucleotide tail of the second region of the first extended primer oligonucleotide, wherein the activator oligonucleotide comprises:
- a first single-stranded region that can bind to the polynucleotide tail of the second region of the first primer oligonucleotide,
- a second single-stranded region that is substantially complementary and can bind to the first region of the first primer oligonucleotide,
- a third single-stranded region that is substantially complementary to at least a segment of the extension product, which has been synthesized by polymerase, of the first primer extension product, wherein the activator oligonucleotide does not serve as template for a primer extension of the first primer oligonucleotide, d) binding the activator oligonucleotide to the first primer region of the first extended primer oligonucleotide by displacing the strand of the nucleic acid chain to be amplified that is complementary to said first primer region, e) binding the activator oligonucleotide to the complementary segment of the extension product of the first extended primer oligonucleotide by displacing the strand of the nucleic acid chain to be amplified that is complementary to said extension product, wherein the 3' segment of the first primer extension product becomes single-stranded, f) hybridizing a second oligonucleotide primer to the first primer extension product, wherein the 3' segment of the second oligonucleotide primer comprises a sequence that can hybridize to the first primer extension product; and g) extending the second oligonucleotide primer with polymerase to form a second primer extension product, wherein the extension takes place up to and including the first primer region of the first primer oligonucleotide and said first primer region is copied by the polymerase, wherein the polynucleotide tail of the second region remains uncopied, h) repeating steps a)-g) until the desired degree of amplification has been achieved, wherein a detection system is added to the reaction mixture, wherein the detection system includes at least two components from the group (fluorescence reporter, donor fluorophore, fluorescence quencher) and allows detection of primer extension products synthesized by polymerase in steps a) to h).

Method according to aspect 1, characterized in that the detection system has a fluorescence reporter and a fluorescence quencher, connected thereto via a nucleotide sequence, or a donor fluorophore, wherein the nucleotide sequence comprises a part of the target sequence or is complementary to a part of the target sequence. One of the components used (first primer, second primer, activator oligonucleotide, oligonucleotide probe) can comprise such a nucleotide sequence.

Method according to aspect 1, characterized in that the detection system has a fluorescence reporter and a fluorescence quencher, connected thereto via a nucleotide sequence, or a donor fluorophore, wherein the nucleotide sequence is complementary to a part of one of the two primer extension products which are synthesized in steps a) to h). One of the components used (first primer, second primer, activator oligonucleotide, oligonucleotide probe) can comprise such a nucleotide sequence.

Method according to aspect 1, characterized in that the detection system has a fluorescence reporter bound to a component that is employed in the method (these components may optionally be: first primer, second primer, activator oligonucleotide, oligonucleotide probe) and that a donor fluorophore or a fluorescence quencher are employed, connected to another component used in the method (such components may optionally be: first primer, second primer, activator oligonucleotide, oligonucleotide probe), wherein a spatial proximity of respective components is effected in the presence of the target sequence to be detected.

Method according to aspect 1, characterized in that the detection system has a fluorescence reporter bound to a component that is employed in the method (these components may optionally be: first primer, second primer, activator oligonucleotide, oligonucleotide probe), and that a donor fluorophore or a fluorescence quencher are used connected to another component used in the method (such components may optionally be: first primer, second primer, activator oligonucleotide, oligonucleotide probe), wherein the absence of a spatial proximity of respective components is effected in the absence of the target sequence to be detected.

Method according to aspect 1, characterized in that a fluorescence resonance energy transfer (FRET) is present in the detection system.

Method according to aspect 1, characterized in that in the detection system the detectable signal of fluorescence reporter is different depending on the presence or absence of the target sequence to be detected and amplified in steps a) to h).

Method according to aspect 1, characterized in that in the detection system the signal of fluorescence reporter is different depending on the presence or absence of the specific primer extension products amplified in steps a) to h).

The oligonucleotide probe comprises a sequence segment that is substantially complementary to the 3' segment of the first primer extension product that can hybridize to the 3' segment of the first primer extension product under suitable conditions (hybridization conditions), wherein at least part of said complementary segment is not identical to the third region of the activator oligonucleotide in the sequence composition and binding of said complementary segment of the oligonucleotide probe is at the 3' segment of the first primer extension product in 3' direction relative to the bound activator oligonucleotide. In this embodiment the oligonucleotide probe comprises at least one fluorescence reporter and/or one fluorescence donor and/or one fluorescence quencher.

Binding of the oligonucleotide probe to the 3' segment of the synthesized first primer extension product under suitable hybridization conditions results in the formation of a double strand. Hybridization conditions are present during the method.

At suitable times during the method the reaction is illuminated with light of a suitable wave length to generate a fluorescence signal and the fluorescence signal from the fluorescence reporter is detected, wherein the intensity of the fluorescence signal is measured.

Detection of the fluorescence signal takes place with suitable optical/physical means with which either the increase of the fluorescence signal or the decrease of the fluorescence signal is measured. With suitable sensors the intensity of the fluorescence signal can be converted to measured values with which after appropriate calibration it is possible to determine whether or not a desired target sequence is present in the reaction mixture.

Figure 3:
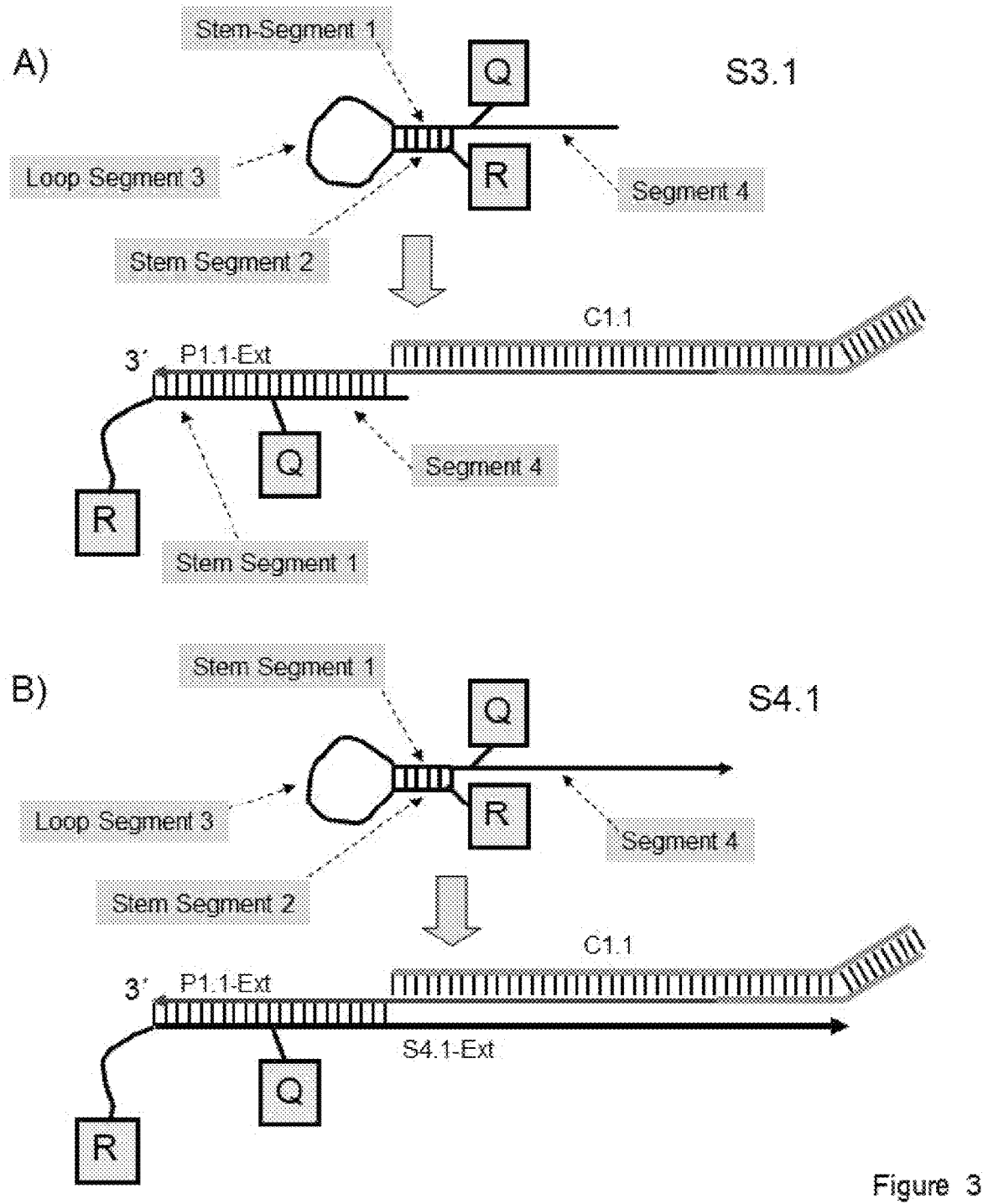

A substantial aspect of the fluorescence detection system is the reporter quencher pair. If the quencher is in spatial proximity to the reporter, no signal is emitted upon illumination with the excitation light. When, as for example illustrated in FIG. 3A, reporter and quencher molecules due to a complementary stem sequence are held in spatial proximity also with illumination no fluorescence signal occurs. However, if the fluorescence system is changed in that the nucleotide sequence between reporter and quencher can hybridize with a target sequence, reporter and quencher are brought to a spatial distance that effects that the quencher is spaced as far from the reporter molecule that the reporter molecule emits a fluorescence radiation when the reaction mixture is radiated with an excitation light source. The distance between reporter and quencher depends on the molecules used each. Typically, then emission of light after radiation of the fluorescence reporter is reduced or almost completely reduced when quencher and reporter are spaced from each other in a distance of less than 25 nucleotides. Said distance may be effected either by the nucleotide sequence or by special molecules effecting the distance such as linkers or spacers.

In a further embodiment the fluorescence reporter may form a specific reporter donor pair (FRET pair) with a donor fluorophore that is able to transfer the absorbed energy to the fluorescence reporter by fluorescence resonance energy transfer (FRET).

A reporter donor pair comprising a fluorescence reporter and a matching donor fluorophore and forming a fluorescence resonance energy transfer pair may be configured such that only one of the partners of such a FRET pair is coupled to the oligonucleotide probe and the other partner is coupled to the activator oligonucleotide. Both fluorescence reporter and donor fluorophore are coupled to the respective oligonucleotide such that in the non-hybridized state of the oligonucleotide probe the donor fluorophore is not able to transfer the absorbed energy to the fluorescence reporter. By a simultaneous hybridization of the activator oligonucleotide to the synthesized first primer extension product and the oligonucleotide probe to the 3' end of the same first primer extension product binding to adjacent sequence positions of the first primer extension product takes place, what results in a spatial narrowing of the donor fluorophore and the fluorescence reporter, and the distance between the fluorescence reporter and donor fluorophore is reduced such that FRET of donor fluorophore to fluorescence reporter can take place. This results in a generation of a fluorescence signal of the fluorescence reporter and in a detectable increase of the fluorescence signal of the fluorescence reporter.

The distance between the donor fluorophore and the fluorescence reporter after hybridization shall represent less than 25, preferably less than 15, and particularly preferred less than 5 nucleotides. The wavelength of the light upon excitation is absorbed by the donor fluorophore and transferred to the reporter, whereby light is emitted which can be detected.

As to the arrangement of the detection system in the amplification product the following embodiments are preferred, wherein either the fluorescence reporter or the fluorescence quencher or the donor fluorophore are coupled either to the activator oligonucleotide, especially in the third region of the activator oligonucleotide:

Coupling to the activator oligonucleotide preferably is in the third region of the activator oligonucleotide, Coupling to the activator oligonucleotide preferably is at the 5' end or to the third region or close to it, e.g. 2 to about 10 nucleotides from the 5' end of the third region, Coupling to the oligonucleotide probe preferably is in the middle region of the oligonucleotide probe, Coupling to the oligonucleotide probe preferably is in the 3' segment of the oligonucleotide probe.

In the context of the present invention additionally particularly preferred are the following aspects:

The distance between both elements of a FRET pair in the hybridized state of oligonucleotides that are hybridized to the first primer extension product is less than about 30 nucleotides.

The oligonucleotide probe that comprises a complementary 3' end to the first primer extension product is modified such that the polymerase is not able to extend said 3' end.

The oligonucleotide probe comprises a complementary 3' end to the first primer extension product, wherein the polymerase is able to extend said 3' end using the first primer extension product as a template to form a complementary strand.

The oligonucleotide probe comprises a complementary 3' end to the first primer extension product, wherein the polymerase is able to extend said 3' end using the first primer extension product as a template to form a complementary strand, wherein the oligonucleotide probe and the second amplification primer are different.

Method for detecting amplification, wherein two or more nucleic acid chains are amplified, in which for each nucleic acid chain to be amplified a specific detection system is used.

Method for detecting amplification, wherein two or more nucleic acid chains are amplified, in which the detection of the amplification of at least two nucleic acid chains to be amplified is by a consistent detection system.

The amplification comprises an asymmetric multiplication of the first and the second primer extension products.

The asymmetric amplification results in a relative excess of the first primer extension products, so that more first primer extension products are formed than second primer extension products.

The excitation of the fluorescence reporter and the measurement of the fluorescence signal of the fluorescence reporter take place during the amplification.

The excitation of the donor fluorophore and the measurement of the fluorescence signal of the fluorescence reporter take place during the amplification.

The excitation of the fluorescence reporter and the measurement of the fluorescence signal of the fluorescence reporter take place after the amplification.

The excitation of the donor fluorophore and the measurement of the fluorescence signal of the fluorescence reporter take place after the amplification.

The oligonucleotide probe is a DNA oligonucleotide.

The oligonucleotide probe comprises a complementary sequence segment of the first primer extension product, wherein said sequence segment has a length of 8 to about 60 nucleotides.

An oligonucleotide probe comprises a complementary sequence segment to the 3' segment of the first primer extension product which is not bound by the activator oligonucleotide, wherein said segment has a length of 8 to about 40 nucleotides.

An oligonucleotide probe comprises self-complementary sequence segments (stem segment 1 and 2), wherein said self-complementary sequence segments are separated from each other by a non-self-complementary sequence segment (loop segment).

An oligonucleotide probe comprises self-complementary sequence segments (stem segment 1 and 2), wherein said self-complementary sequence segments have a length of 3 to about 20 nucleotides.

An oligonucleotide probe can comprise a loop segment between both self-complementary sequence segments in a length of about 2 to about 40 nucleotides.

An oligonucleotide probe comprises self-complementary sequence segments (stem segment 1 and 2), wherein said self-complementary sequence segments are separated from each other by a non-self-complementary sequence segment (loop segment), wherein one of the two self-complementary sequence segments can complementary bind to the 3' segment of the first primer extension product.

An oligonucleotide probe comprises self-complementary sequence segments (stem segment 1 and 2), wherein said self-complementary sequence segments are separated from each other by a non-self-complementary sequence segment (loop segment), wherein the loop segment can complementary bind to the 3' segment of the first primer extension product.

An oligonucleotide probe comprises self-complementary sequence segments (stem segments 1 and 2), wherein said self-complementary sequence segments are separated from each other by a non-self-complementary sequence segment (loop segment) and fluorescence reporter and fluorescence quencher are bound to respectively different self-complementary sequence segments.

An oligonucleotide probe comprises self-complementary sequence segments (stem segment 1 and 2), wherein said self-complementary sequence segments are separated from each other by a non-self-complementary sequence segment (loop segment) and further comprises a fourth sequence segment which can complementary bind to the first primer extension product and is not stem segment 1, 2 or loop segment.

An oligonucleotide probe comprises at least one further modification selected from the following group: linker (e.g. HEG, C3, C6), phosphate sugar backbone modifications (e.g. PTO, 2'-O-Me, RNA, PNA, LNA modifications).

In one embodiment, the method is performed under conditions that do not allow a separation of complementary strands of the nucleic acid to be amplified in the absence of activator oligonucleotide.

In one embodiment, copying the polynucleotide tail is caused in the second primer region by a stopping region for the polymerase that is arranged between the first and the second regions.

In one embodiment, the third single-stranded region of the activator oligonucleotide is substantially complementary to the segment of the extension product, which has been synthesized by the polymerase, of the first primer extension product, which immediately follows the first primer region, wherein:

In one embodiment, the third single-stranded region of the activator oligonucleotide is completely complementary to the mentioned 5' segment of the extension product of the first primer extension product, wherein the length of said complementary sequence part comprises the following ranges: of at least 3 to 70 nucleotides, better of at least 5 to 50 nucleotides, preferably of 5 to 40 nucleotides, further preferably of 5 to 30 nucleotides, particularly preferred of 5 to 20 nucleotides.

In a further embodiment, the sequences of the third single-stranded region of the activator oligonucleotide and the corresponding sequence of the mentioned 5' segment of the extension product of the first primer extension product comprise complementary sequences except for one sequence position (a pair of nucleotides/bases) having a non-complementary base pairing (in the meaning of Watson-Crick base pairing) over a length of at least 3 to 70 nucleotides, better of at least 5 to 60 nucleotides, preferably of 10 to 40 nucleotides, particularly preferred of 10 to 20 nucleotides. Thus, the binding of the activator oligonucleotide is essentially complementary.

In a further embodiment, the sequences of the third single-stranded region of the activator oligonucleotide and the corresponding sequence of the mentioned 5' segment of the extension product of the first primer extension product comprise complementary sequences except for two sequence positions (a pair of nucleotides/bases) having a non-complementary base pairing (in the meaning of Watson-Crick base pairing) over a length of at least 3 to 70 nucleotides, better of at least 5 to 60 nucleotides, preferably of 10 to 40 nucleotides, particularly preferred of 10 to 20 nucleotides. Thus, the binding of the activator oligonucleotide is essentially complementary.

In a further embodiment, the sequences of the third single-stranded region of the activator oligonucleotide and the corresponding sequence of the mentioned 5' segment of the extension product of the first primer extension product comprise complementary sequences (in the meaning of Watson-Crick base pairing) over a length of at least 3 to 70 nucleotides, better of at least 5 to 60 nucleotides, preferably of 10 to 40 nucleotides, particularly preferred of 10 to 20 nucleotides, further said segments comprise non-complementary regions in at least three sequence positions, wherein said positions are within the 5' segment of the third section of the activator oligonucleotide. Thus, the binding of the activator oligonucleotide is essentially complementary.

In a further embodiment, the sequences of the third single-stranded region of the activator oligonucleotide and the sequence of the mentioned 5' segment of the extension product of the first primer extension product comprise complementary sequences except for at least one and at most ten sequence positions having a non-complementary base pairing (in the meaning of Watson-Crick base pairing) over a length of at least 3 to 70 nucleotides, better of at least 5 to 60 nucleotides, preferably of 10 to 40 nucleotides, particularly preferred of 10 to 20 nucleotides, wherein in sequence positions having non-complementary base pairing (in the meaning of Watson-Crick base pairing) at least one modified nucleotide having modified nucleobases is involved. Such modified nucleobases comprise for example nucleobases with enhanced binding of natural nucleobases (e.g., 2-amino adenines), or with attenuated binding such as for example so-called universal bases such as inosines or 5-nitroindole. The modified nucleobases are preferably located in the third sequence region of the activator oligonucleotide. Thus, the binding of the activator oligonucleotide is essentially complementary.

In a further embodiment of the method step (e) of the method is further modified and comprises:

the binding of the activator oligonucleotide to the complementary segment of the extension product of the first extended primer oligonucleotide by displacing the strand of the nucleic acid chain to be amplified that is complementary to said extension product until said complementary strand of the nucleic acid to be amplified is detached from the first primer extension product, wherein the 3' segment of the first primer extension product becomes single-stranded.

In a further embodiment of the method step (f) of the method is further modified and comprises:

the hybridization of a second oligonucleotide primer to the first primer extension product, wherein at the same time there is at least a partial displacement of the activator oligonucleotide from the binding with the first extension product by strand displacement.

In a further embodiment of the method step (g) of the method is further modified and comprises a displacement of the activator oligonucleotide from the binding with the first primer extension product with the participation of the polymerase.

In a further embodiment of the method step (h) of the method is further modified and comprises: optionally the binding of the activator oligonucleotide to the uncopied polynucleotide tail of the first extended primer oligonucleotide and a displacement of the second primer extension product from the binding to the first primer extension product with the simultaneous formation of a complementary double strand with a segment of the first specific extension product of the first primer oligonucleotide.

In a further embodiment of the method the method is further modified and comprises: h) continuation of the reaction under conditions that allow a repletion of steps (a) to (g).

In a further embodiment of the method the method is further modified and comprises: the simultaneous amplification of the first and second primer extension products in an exponential reaction by using the first and second primer oligonucleotides and the activator oligonucleotide, wherein the formed primer extension products function as a template for the mutual synthesis.

Reaction Conditions

The reaction conditions comprise among others buffer conditions, temperature conditions, duration of the reaction, and concentrations of respective reaction components.

During the reaction the amount of the specifically produced nucleic acid to be amplified accumulates in an exponential manner. The reaction comprising the synthesis of the extension products can be carried out for the production of the desired amount of the specific nucleic acid sequence as long as needed. The method according to the invention is preferably carried out continuously. In a preferable embodiment, the amplification reaction proceeds at the same reaction temperature, wherein the temperature is preferably between 50° C. and 70° C. In another embodiment, the reaction temperature can also be controlled variably, so that single steps of the amplification each proceed at different temperatures.

The reagents needed for the exponential amplification are preferably present already at the beginning of a reaction in the same batch. In another embodiment, reagents can also be added in later stages of the method.

Preferably, no helicases or recombinases are used in the reaction mixture for the separation of the newly synthesized double strands of the nucleic acid to be amplified.

In a preferred embodiment, the reaction mixture does not contain biochemical energizing compounds such as ATP.

The amount of the nucleic acid to be amplified that is present at the beginning of the reaction can be present in one batch between a few copies and several billions of copies. In case of diagnostic use the amount of the nucleic acid chain to be amplified can be unknown.

In the reaction also further nucleic acids not to be amplified can be present. These nucleic acids can be derived from natural DNA or RNA or their equivalents. In one embodiment, control sequences are present in the same batch that have to be amplified in parallel to the nucleic acid to be amplified.

Preferably, a molar excess of approximately $10^3$:1 to approximately $10^{15}$:1 (ratio of primer:template) of the primers used and of the activator oligonucleotide is added to the reaction mixture that comprises template strands for the synthesis of the nucleic acid chain to be amplified.

The amount of the target nucleic acids may not be known if the method according to the invention is used in diagnostic applications, so that the relative amount of the primer and of the activator oligonucleotide with respect to the complementary strand cannot certainly be determined. The amount of the primer added will generally be present in the molar excess with respect to the amount of the complementary strand (template) if the sequence to be amplified is contained in a mixture of complex long-chain nucleic acid strands. A large molar excess is preferred in order to improve efficacy of the method.

The concentrations of primer 1, primer 2 and activator oligonucleotide used are for example in ranges between 0.01 µmol/l and 100 µmol/l, preferably between 0.1 µmol/l and 100 µmol/l, preferably between 0.1 µmol/l and 50 µmol/l, better between 0.1 µmol/l and 20 µmol/l. The high concentration of components can increase the rate of the amplification. The respective concentrations of individual components can independently be varied in order to achieve the desired reaction result.

The concentration of polymerase is in the range between 0.001 µmol/l and 50 mol/l, preferably between 0.01 µmol/l and 20 µmol/l, better between 0.1 µmol/l and 10 µmol/l.

The concentration of individual dNTP substrates is in ranges between 10 mol/l and 10 mmol/l, preferably between 50 µmol/l and 2 mmol/l, better between 100 µmol/l and 1 mmol/l. The concentration of dNTP can affect the concentration of divalent metal cations. Optionally, this is correspondingly adjusted.

As divalent metal cations there are for example used Mg2+. As the corresponding anion Cl, acetate, sulphate, glutamate, etc. can be used, for example.

The concentration of divalent metal cations is adapted for example to the region that is optimal for the corresponding polymerase and comprises regions between 0.1 mmol/l and 50 mmol/l, better between 0.5 mmol/l and 20 mmol/l, preferably between 1 mmol/l and 15 mmol/l.

In general, enzymatic synthesis takes place in a buffered aqueous solution. As buffer solutions dissolved conventional buffer substances such as Tris HCl, Tris acetate, potassium glutamate, HEPES buffer, sodium glutamate in common concentrations can be used. The pH value of said solutions is usually between 7 and 9.5, preferably about 8 to 8.5. The buffer conditions may be adapted for example in accordance with the recommendations of the manufacturer of the polymerase used.

Further substances such as so-called Tm depressors (e.g., DMSO, betaines, TPAC), etc. can be added to the buffer. Such substances decrease the melting temperature ("Tm depressors") of double strands and thus, can have a positive influence on the opening of double strands.

Also, polymerase-stabilizing components such as Tween 20 or Triton 100 can be added to the buffer in the usual amounts. EDTA or EGTA can be added in conventional amounts for complexation of heavy metals. Also, polymerase-stabilizing substances such as trehalose or PEG 6000 can be added to the reaction mixture.

Preferably, the reaction mixture does not contain any inhibitors of the strand displacement reaction and no inhibitors of a polymerase-depending primer extension.

In one embodiment, the reaction mixture contains DNA-binding dyes, preferably intercalating dyes such as e.g., EvaGreen or SybrGreen. Such dyes can optionally enable the detection of the reproduction of nucleic acid chains.

The reaction mixture can further contain proteins or other substances that for example originate from an original material and that preferably do not affect the amplification.

Preferred Embodiments of Reaction Conditions

The temperature has a substantial influence on the stability of the double strands.

In a preferred embodiment, during the amplification reaction no temperature conditions are used that substantially result in a separation of double strands of the nucleic acid to be amplified in the absence of an activator oligonucleotide. In this way, it is to be ensured that the double strand separation of nucleic acid chains to be amplified depends on the presence of the activator oligonucleotide throughout the amplification.

At a temperature approximately equal to the measured melting temperature (Tm) of the nucleic acid to be amplified a spontaneous separation of both strands of the nucleic acid to be amplified occurs, so that the influence of the activator oligonucleotide on the separation of synthesized strands and thus, on the sequence specificity of the amplification is minimally limited.

In an exponential amplification that has to proceed less sequence-specifically (i.e. little activator oligonucleotide-dependent) the reaction temperature can be for example around the melting temperature (i.e. Tm plus/minus 3° C. to 5° C.) of the nucleic acid to be amplified. At such a temperature sequence differences between activator oligonucleotide and the synthesized primer extension product generally can be well tolerated during a strand displacement reaction.

Also, in the temperature range of ca. (Tm minus 3° C.) to ca. (Tm minus 10° C.) there can still be a spontaneous strand separation of synthesized primer extension products, although with less efficacy. The influence of the activator oligonucleotide on the sequence specificity of the nucleic acid to be amplified is higher than at temperature conditions around the melting temperature (Tm) of the nucleic acid chain to be amplified.

Certainly, with a decreasing reaction temperature strand separation substantially takes place owing to the interaction of the re-synthesized double strand with the activator oligonucleotide, but duplexes of primers can spontaneously decompose at an extension temperature under the mentioned conditions, i.e. without sequence-dependent strand displacement by the activator oligonucleotide. For example, the reaction temperature in a less sequence-specific amplification is in ranges between ca. (Tm minus 3° C.) and ca. (Tm minus 10° C.), preferably between ca. (Tm minus 5° C.) and ca. (Tm minus 10° C.). At such a temperature sequence differences between the activator oligonucleotide and the synthesized primer extension product are tolerated less well during a strand displacement reaction.

A high sequence specificity of the amplification of the method is achieved above all when the re-synthesized strands of the nucleic acid to be amplified under reaction conditions cannot spontaneously dissociate into single strands. In such a case, sequence-specific strand displacement by the activator oligonucleotide plays a decisive role for a sequence-specific strand separation and is mainly responsible for the sequence specificity of the amplification reaction. This can generally be achieved when the reaction temperature is significantly below the melting temperature of both strands of the nucleic acid to be amplified and no further components are used for a strand separation, for example no helicases or recombinases. For example, the reaction temperature in a sequence-specific amplification is in ranges between ca. (Tm minus 10° C.) and ca. (Tm minus 50° C.), preferably between ca. (Tm minus 15° C.) and ca. (Tm minus 40° C.), better between ca. (Tm minus 15° C.) and ca. (Tm minus 30° C.).

In a preferred embodiment of the amplification the maximum reaction temperature during the whole amplification reaction will not be increased above the melting temperature of the nucleic acid chain to be amplified.

In a further embodiment of the amplification the reaction temperature can be increased above the melting temperature of the nucleic acid chains to be amplified at least once. The increase in temperature may be for example at the beginning of the amplification reaction and result in a denaturation of double strands of a genomic DNA. Here, it has to be noted that during such a step the dependency of double strand separation on the effect of the activator oligonucleotide is canceled or at least significantly reduced.

The reaction temperatures of the individual steps of the amplification reaction can be in the range of ca. 15° C. to ca. 85° C., better in the range of ca. 15° C. to ca. 75° C., preferably in the range of ca. 25° C. to ca. 70° C.

In examples 2 and 3 described below a reaction temperature of the amplification reaction of 65° C. was used, wherein the Tm of the nucleic acids to be amplified was between ca. 75° C. and ca. 80° C. Thus, the double strand of the nucleic acid to be amplified was stable under the reaction conditions and the amplification reaction was sequence-specific (see, example 3).

Generally, the reaction temperature can optimally be adjusted for each individual reaction step, so that for each reaction step such a temperature is brought about. Thus, the amplification reaction comprises a repeating change in temperatures that is repeated cyclically. In an advantageous embodiment of the method reaction conditions for several reaction steps are unified, so that the number of temperature steps is lower than the number of reaction steps. In such a preferred embodiment of the invention at least one of the steps of the amplification takes place at a reaction temperature that differs from the reaction temperature of other steps of the amplification. Thus, the reaction does not proceed isothermal, but the reaction temperature is cyclically changed.

For example, during the amplification at least two temperature ranges are used that are mutually brought about (cyclic change in temperatures between individual temperature ranges). In one embodiment, for example the lower temperature range comprises temperatures between 25° C. and 60° C., better between 35° C. and 60° C., preferably between 50° C. and 60° C., and the upper temperature range comprises temperatures between 60° C. and 75° C., better between 60° C. and 70° C., for example.

In a further embodiment, for example the lower temperature range comprises temperatures between 15° C. and 50° C., better between 25° C. and 50° C., preferably between 30° C. and 50° C., and the upper temperature range comprises temperatures between 50° C. and 75° C., better between 50° C. and 65° C., for example.

In a further embodiment, for example the lower temperature range comprises temperatures between 15° C. and 40° C., better between 25° C. and 40° C., preferably between 30° C. and 40° C., and the upper temperature range comprises temperatures between 40° C. and 75° C., better between 40° C. and 65° C., for example.

The temperature can be maintained constant in the respective range or changed as a temperature gradient (falling or rising).

Further explanations on the temperature adjustments are given in detail in the following sections in the embodiments.

Each temperature brought about can be maintained for a certain period of time, so that in this way an incubation step results. Thus, the reaction mixture can be incubated during an amplification at a selected temperature for a certain period of time. This time can be different for the respective incubation step and can depend on the progress of the respective reaction at a given temperature (e.g., primer extension or strand displacement etc.). The time of an incubation step can comprise the following ranges: between 0.1 sec and 10.000 sec, better between 0.1 sec and 1000 sec, preferably between 1 sec and 300 sec, more preferably between 1 sec and 100 sec.

By such a temperature change individual reaction steps can preferably be carried out at a selected temperature. In this way, yields of a respective reaction step can be improved. Temperature change or temperature alteration between individual temperature ranges can optionally be brought about several times within one synthesis cycle. Thus, a synthesis cycle can comprise at least one temperature alteration. Such a temperature alteration can for example be carried out in a PCR instrument/thermocycler as a matter of routine as a time program.

In one embodiment, an amplification method is preferred in which at least one of the steps comprising strand displacement and at least one of the steps comprising primer extension reactions take place at the same time or in parallel and under the same reaction conditions. In such an embodiment, for example a primer extension reaction of at least one primer oligonucleotide (e.g., of the first primer oligonucleotide) can preferably take place at temperature conditions in the lower temperature range. In contrast, strand displacement takes place with cooperation of an activator oligonucleotide and the one further primer extension reaction (e.g., of the second primer oligonucleotide) preferably in the reaction step in the upper temperature range.

In a further embodiment, an amplification method is preferred in which at least one of the steps comprising strand displacement by the activator oligonucleotide and at least one of the steps comprising primer extension reactions are carried out at different temperatures. In such an embodiment, for example primer extension reactions of at least one primer oligonucleotide (e.g., of the first primer oligonucleotide and/or of the second primer oligonucleotide) can preferably take place at temperature conditions in the lower temperature range. In contrast, strand displacement takes place with cooperation of an activator oligonucleotide preferably in the reaction step in the upper temperature range.

In a further preferred embodiment, all the steps of an amplification reaction proceed under the same reaction conditions.

In such an embodiment, the amplification method can be carried out under isothermal conditions, i.e. no temperature changes are required to carry out the method. In such a preferred embodiment of the invention the whole amplification reaction takes place under a constant temperature, i.e. the reaction is isothermal. The duration of such a reaction comprises for example the following ranges: between 100 sec and 30,000 sec, better between 100 sec and 10,000 sec, still better between 100 sec and 1,000 sec.

In section "Examples" it is shown that it is possible to adapt structures of individual reaction components and the corresponding reaction steps to each other to such an extent that an isothermal reaction is possible.

The sum of all method steps resulting in a doubling of the amount of a nucleic acid chain to be amplified can be referred to as synthesis cycle. Such a cycle can correspondingly proceed isothermal or be characterized in its course by changes of the temperature. The temperature changes can be repeated from cycle to cycle and made identical.

Of particular advantage are amplification methods in which the maximum achievable temperature only substantially allows a strand separation with the cooperation of an activator oligonucleotide if more than 5 nucleotides of the third region of the activator oligonucleotide are able to complementary bind to the first primer extension product, it is more preferred if more than 10, still more preferred if more than 20 nucleotides of the activator oligonucleotide bind to the first primer extension product. Generally, the longer the required binding between activator oligonucleotide and the complementary strand of the first primer extension product, before the synthesized strands dissociate under reaction conditions, the more specific the amplification reaction. In detail, by extending or shortening the third section of the activator oligonucleotide the desired degree of specificity can be determined.

A method step when repeated can take place at a constant temperature over the total duration of the method or also at different temperatures.

Individual method steps each can be carried out consecutively by adding individual components. In an advantageous embodiment all the reaction components required to carry out an amplification are present at the beginning of an amplification in one reaction mixture.

The start of an amplification reaction can be by adding one component, e.g., by adding a nucleic acid chain comprising a target sequence (e.g., a start nucleic acid chain), or a polymerase or divalent metal ions, or also by bringing about reaction conditions needed for amplification, e.g., adjusting a required reaction temperature for one or more method steps.

Amplification can be carried out until the desired amount of nucleic acid to be amplified has been achieved. In another embodiment, the amplification reaction is carried out for a period of time that would have been sufficient, in the presence of a nucleic acid to be amplified, to get a sufficient amount. In another embodiment, the amplification reaction is carried out over a sufficient number of synthesis cycles (duplication times) that would have been sufficient, in the presence of a nucleic acid to be amplified, to get a sufficient amount.

The reaction can be stopped by various interventions. For example, by changing the temperature (e.g., cooling or heating, wherein for example polymerase is interfered in its function) or by adding a substance that stops a polymerase reaction, e.g., EDTA or formamide.

Following the amplification the amplified nucleic acid chain can be used for further analyses. Here, synthesized nucleic acid chains can be analyzed by various detection methods. For example, fluorescence-labeled oligonucleotide probes can be used or sequencing methods (Sanger sequencing or next generation sequencing), solid phase analyses such as microarray or bead array analyses etc. The synthesized nucleic acid chain can be used as a substrate/template in further primer extension reactions.

In an advantageous embodiment, the progress of the synthesis reaction during the reaction is monitored. This can be done for example by employing intercalating dyes, e.g., SYBRgreen or Evagreen, or by employing labeled primers (e.g., Lux primers or Scorpion primers) or by employing fluorescence-labeled oligonucleotide probes.

The detection of the change in the fluorescence during the amplification is implemented in the detection step of the method. Here, the temperature and duration of said step can be adapted to the respective requirements of the oligonucleotide probe. The temperatures of the detection step for example comprise ranges between 20° C. and 75° C., better between 40 and 70° C., preferably between 55 and 70° C.

During the detection step the reaction is illuminated with light of a wavelength that is able to excite a used fluorophore of the detection system (a donor or a fluorescence reporter). Generally, signal detection is in parallel to excitation, wherein the specific fluorescence signal is detected and its intensity is quantified.

The amplification method can be applied to verify the presence of a target nucleic acid chain in a biological material or a diagnostic material during a diagnostic method.

Preferred Embodiments of a Start Nucleic Acid Chain

Figure 1:
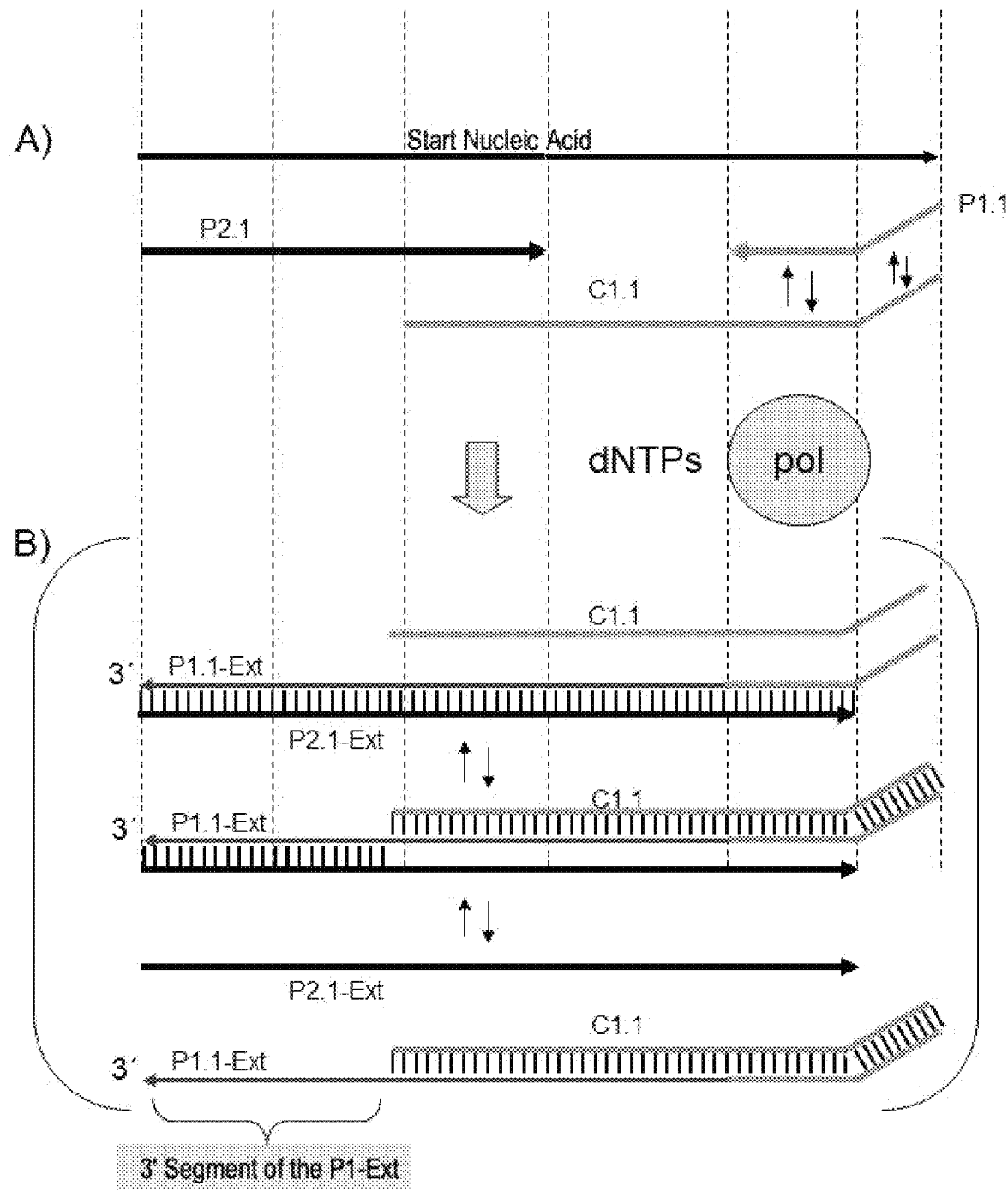

The nucleic acid chain employed or to be employed at the beginning of the amplification reaction can be referred to as a start nucleic acid chain (FIG. 1).

Its function can be seen in that it represents the initial template that permits a correct positioning of primers, the synthesis sections between both primers as well as the initiation of binding and extension processes. In a preferred embodiment, a start nucleic acid chain comprises a target sequence.

By binding primers to their respective primer binding sites (PBS 1 and PBS 2) and initiating appropriate primer extension reactions first primer extension products are generated. These are synthesized as specific copies of the nucleic acid chain present at the beginning of the reaction.

In one embodiment, this nucleic acid chain (start nucleic acid chain) to be used in the reaction mixture before the beginning of the amplification reaction can be identical to the nucleic acid chain to be amplified. By the amplification reaction only the amount of such nucleic acid chain is increased.

In a further embodiment, the nucleic acid to be amplified and the start nucleic acid chain differ in that certainly the start nucleic acid chain prescribes the arrangement of individual sequence elements of the nucleic acid chain to be amplified, but the sequence composition of the start nucleic acid chain can differ from the sequence of the nucleic acid chain to be amplified. For example, in context of the primer binding and extension during an amplification new sequence contents (regarding the start nucleic acid chain) can be integrated into the nucleic acid chain to be amplified. Moreover, sequence elements of a nucleic acid chain to be amplified can differ from such sequence elements of a start nucleic acid chain in their sequence composition (e.g., primer binding sites or primer sequences). The start nucleic acid only serves as an initial template for the specific synthesis of the nucleic acid chain to be amplified. Said initial template can remain in the reaction mixture until the end of the amplification. However, by the exponential nature of the amplification the amount of the nucleic acid chain to be amplified at the end of an amplification reaction predominates the amount of a start nucleic acid chain to be added to the reaction.

Preferred Embodiments of the First Primer Oligonucleotide (Primer 1)

The first primer oligonucleotide (primer 1) is a nucleic acid chain that includes at least the following regions (FIGS. 14 and 15):
  a first primer region in the 3' segment of the first primer oligonucleotide that can substantially sequence-specifically bind to a strand of a nucleic acid chain to be amplified
  a second region directly or via a linker linked to the 5' end of the first primer region of the first primer oligonucleotide that comprises a polynucleotide tail suitable to bind an activator oligonucleotide and support the strand displacement (step c) by the activator oligonucleotide, wherein the polynucleotide tail substantially remains single-stranded under the reaction conditions, i.e. does not form a stable hairpin structure or ds structures, and preferably is not copied by polymerase.

The total length of the first primer oligonucleotide is between 10 and 80, preferably between 15 and 50, better between 20 and 30 nucleotides or equivalents thereof (e.g., nucleotide modifications). The structure of the first primer oligonucleotide is adapted such that it is able to reversibly bind to the activator oligonucleotide under the selected reaction conditions. Moreover, the structure of the first primer oligonucleotide is adapted to its primer function. Moreover, the structure is adapted such that a strand displacement by means of the activator oligonucleotide can be performed. Altogether, structures of the first and second regions are adapted such that an exponential amplification can be performed.

In an advantageous embodiment of the invention the first and second regions of the primer are coupled in a conventional 5'-3' arrangement. In a further embodiment of the invention coupling of both sections is done via a 5'-5' bond, so that the second region has an opposite direction to the first region.

Coupling regions between each other/among each other is done preferably covalently. In one embodiment, coupling between the first and second regions is a 5'-3' phosphodiester coupling that is conventional for DNA. In a further embodiment it is a 5'-5' phosphodiester coupling. In a further embodiment, it is a 5'-3' phosphodiester coupling, wherein between adjacent terminal nucleotides or nucleotide modifications of both regions at least one linker (e.g., a C3, C6, C12, or a HEG linker or an abasic modification) is positioned.

Individual regions can include different nucleotide modifications. Here, individual elements of nucleotides can be modified: nucleobase and backbone (sugar content and/or phosphate content). Moreover, there can be used modifications that lack at least one component of the standard nucleotide building blocks or are modified, e.g., PNA.

In a further embodiment, a second region of the first primer oligonucleotide comprises further sequences that do not bind to the activator oligonucleotide. These sequences can be used for other purposes, e.g., for binding to the solid phase. These sequences are preferably localized at the 5' end of the polynucleotide tail.

In a further embodiment, a first primer oligonucleotide can comprise a characteristic label. Examples of such a label are dyes (e.g., FAM, TAMRA, Cy3, Alexa 488 etc.) or biotin or other groups that can specifically be bound, e.g., digoxigenin.

The First Primer Region of the First Primer Oligonucleotide

The sequence length is between ca. 3-30 nucleotides, preferably between 5 and 20 nucleotides, wherein the sequence is mainly complementary to the 3' segment of a strand of the nucleic acid chain to be amplified. In detail, said primer region has to be able to specifically bind to the complementary 3' segment of a second primer extension product. Said first region is to be copyable in backward synthesis and also functions as a template for a 2nd strand. Preferably, the nucleotide building blocks are linked among each other via common 5'-3' phosphodiester binding or phosphothioester binding.

The first primer region preferably includes nucleotide monomers that do not or only marginally affect the function of the polymerase, these are for example:
- natural nucleotides (dA, dT, dC, dG etc.) or modifications thereof without altered base pairing
- modified nucleotides, 2-amino-dA, 2-thio-dT or other nucleotide modifications with diverging base pairing.

In a preferred embodiment, the 3'-OH end of said region is preferably free from modifications and has a functional 3'-OH group that can be recognized by polymerase. The first primer region functions as an initiator of the synthesis of the first primer extension product in the amplification. In a further preferred embodiment, the first region comprises at least one phosphorothioate compound, so that no degradation of the 3' end of the primers by 3' exonuclease activity of polymerases can take place.

The sequence of the first region of the first primer oligonucleotide and the sequence of the second region of the activator oligonucleotide are preferably complementary to each other.

In one embodiment, the first primer region or its 3' segment can bind to sequence segments of a target sequence.

The Second Region of the First Primer Oligonucleotide

The second region of the first primer oligonucleotide is preferably a nucleic acid sequence that comprises at least one polynucleotide tail that remains preferably uncopied by polymerase during the synthesis reaction and that can bind to the first region of the activator oligonucleotide. The segment of the second region that mainly binds to the activator oligonucleotide can be referred to as polynucleotide tail.

Further, the second region of the first primer oligonucleotide not only has to specifically bind the activator oligonucleotide under reaction conditions, but also has to participate in the process of strand displacement by means of the activator oligonucleotide. Accordingly, the structure of the second region must be suitable for causing a spatial proximity between the activator oligonucleotide and the corresponding double strand end (in detail, the 3' end of the second primer extension product).

Configuration of the structure of the second region of the first primer oligonucleotide is illustrated in detail in several embodiments. Here, the arrangement of the oligonucleotide segments and modifications used are taken into account that lead to a stop in the polymerase-catalyzed synthesis.

The length of the second region is between 3 and 60, preferably between 5 and 40, preferably between 6 and 15 nucleotides or equivalents thereof.

The sequence of the second region may be chosen arbitrarily. Preferably, it is non-complementary to the nucleic acid to be amplified and/or to the second primer oligonucleotide and/or to the first region of the first primer oligonucleotide. Moreover, it preferably does not contain any self-complementary segments such as hairpins or stem loops.

The sequence of the second region is preferably adapted to a sequence of the first region of the activator oligonucleotide, so that both sequences can bind under reaction conditions. In a preferred embodiment, said binding is reversible under reaction conditions: thus, there is an equilibrium between components bound to each other and unbound components.

The sequence of the second region of the first primer oligonucleotide is preferably selected such that the number of complementary bases that can bind to the first region of the activator oligonucleotide is between 1 and 40, better between 3 and 20, preferably between 6 and 15.

The function of the second region among others is to bind the activator oligonucleotide. In one embodiment, said binding preferably is specific, so that a second region of a first primer oligonucleotide can bind a specific activator oligonucleotide. In another embodiment, a second region can bind more than only one activator oligonucleotide under reaction conditions.

In general, there is no need for a perfect match in the sequence between the second region of the first primer oligonucleotide and the first region of the activator oligonucleotide. The degree of the complementarity between the second region of the first primer oligonucleotide and the first region of the activator oligonucleotide can be between 20% and 100%, better between 50% and 100%, preferably between 80% and 100%. The respectively complementary regions can be positioned directly adjacent to each other or also comprise non-complementary sequence segments therebetween.

In one embodiment, the second region of the first primer oligonucleotide can include at least one Tm-modifying modification. By incorporating such modifications the stability of the bond between the second region of the first primer oligonucleotide and the first region of the activator oligonucleotide can be modified. For example, Tm-rising modifications (nucleotide modifications or non-nucleotide modifications) can be used such as LNA nucleotides, 2-amino adenosines or MGB modifications. On the other hand, also Tm-decreasing modifications can be used such as for example inosine nucleotide. In the structure of the second region also linkers (e.g., C3, C6, HEG linkers) can be integrated.

For strand displacement the activator oligonucleotide has to be brought in spatial proximity of the double strand end of the nucleic acid to be amplified. Said double strand end consists of segments of the first primer region of the first primer extension product and a correspondingly complementary 3' segment of the second primer extension product.

The polynucleotide tail mainly complementary binds the activator oligonucleotide under reaction conditions and thus, causes a transient approximation of the second region of the activator oligonucleotide and of the first region of an extended primer extension product, so that the complementary bond between said elements can be initiated during a strand displacement process.

In one embodiment, binding of the activator oligonucleotide to the polynucleotide tail of the first primer oligonucleotide directly leads to such a contact. This means that the polynucleotide tail and the first primer region of the first primer oligonucleotide have to be directly coupled to each other. Owing to such an arrangement there may be a direct contact between complementary bases of the second region of the activator oligonucleotide and corresponding bases of the first primer region after an activator oligonucleotide has bound in its first region, so that a strand displacement can be initiated.

In a further embodiment, there are other structures of the second region of the first primer oligonucleotide between structures of the polynucleotide tail and the first primer region. Thus, after an activator oligonucleotide has bound to the polynucleotide tail this is not directly positioned to the first primer region, but in a certain distance thereto. The structures between the non-copyable polynucleotide tail and the copyable first primer region of the primer oligonucleotide can generate such a distance. Said distance has a value that is between 0.1 and 20 nm, preferably between 0.1 and 5 nm, better between 0.1 and 1 nm.

Such structures for example represent linkers (e.g., C3 or C6 or HEG linkers) or segments that are not complementary to the activator oligonucleotide (e.g., in the form of non-complementary, non-copyable nucleotide modifications). The length of these structures can generally be measured in chain atoms. Said length is between 1 and 200 atoms, preferably between 1 and 50 chain atoms, preferably between 1 and 10 chain atoms.

In order to keep the polynucleotide tail of polymerase uncopyable under amplification conditions the second region of the first primer oligonucleotide generally comprises sequence-alignments or structures, respectively that lead to a stop of the polymerase in the synthesis of the second primer extension product after the polymerase has successfully copied the first primer region. Said structures are to prevent the polynucleotide tail of the second region from being copied. Thus, the polynucleotide tail preferably remains uncopied by the polymerase.

In one embodiment, such structures are between the first primer region and the polynucleotide tail.

In a further embodiment, the sequence of the polynucleotide tail can include nucleotide modifications that lead to a stop of the polymerase. In this way, a sequence segment of the second region of the first primer oligonucleotide can comprise both functions: it is both a polynucleotide tail and a sequence of nucleotide modifications leading to a stop of the polymerase.

Modifications in the second region of the first primer oligonucleotide that lead to a synthesis stop and thus, leave the polynucleotide tail uncopied in this application are combined under the term "first blocking unit or a stop region".

In summary, the termination of the synthesis of polymerase in the second region may be achieved in different manners. However, this blockage preferably only takes place when the polymerase has copied the first region of the first primer oligonucleotide. In this way it is ensured that a second primer extension product has an appropriate primer binding site in its 3' segment. This primer binding site is exposed during the strand displacement and thus, is available for a new binding of a further first primer oligonucleotide.

In the synthesis of the complementary strand to the first primer extension product the primer extension reaction stops before the polynucleotide tail. Since in this way this polynucleotide tail remains single-stranded for interaction with the activator oligonucleotide and thus, is available for binding it supports the initiation of the strand displacement reaction by the activator oligonucleotide by bringing the corresponding complementary segments of the activator oligonucleotide in close proximity to the appropriate duplex end. In this way, the distance between the complementary part of the activator oligonucleotide (second region) and the complementary part of the extended primer oligonucleotide (first region) is reduced to a minimum. Such a spatial proximity facilitates the initiation of the strand displacement.

In the context of a schematic illustration of a nucleic acid-mediated strand displacement reaction now a complementary sequence of an activator oligonucleotide is in close proximity of the appropriate duplex end. This results in competition for the binding to the first region of the first primer oligonucleotide between the strand of the activator oligonucleotide and the template strand complementary to the primer. By repetitively closing and forming base pairing between the primer region and the complementary segment of the activator oligonucleotide (second region of the activator nucleotide) or the complementary segment of the template strand, respectively initiation of the nucleic acid-mediated strand displacement process occurs.

Generally, the yield of the initiation of the strand displacement is the higher the closer the corresponding complementary sequence part of the activator oligonucleotide is to the complementary segment of the primer region. However, when this distance is increased the yield of the initiation of the strand displacement decreases.

In the context of the present invention it is not mandatory that the initiation of the strand displacement works at the maximum yield. Thus, distances between the 5' segment of the first primer region of the first primer oligonucleotide, that binds to a complementary strand of the template and forms a complementary duplex, and a corresponding complementary sequence part in the activator oligonucleotide when bound to the polynucleotide tail of the second region of the first primer oligonucleotide may be in the following ranges: between 0.1 and 20 nm, better between 0.1 and 5 nm, even better between 0.1 and 1 nm. In the preferred case, said distance is less than 1 nm. Expressed in other units said distance corresponds to a track of less than 200 atoms, even better less than 50 atoms, even better less than 10 atoms. In the preferred case, said distance is one atom. The distance information is for orientation only and to illustrate that shorter distances between these structures are preferred.

In many cases, said distance can only be measured by analyzing the exact structures of oligonucleotides and evaluating the measurement of sequence distances or linker lengths.

The first primer may also comprise further sequence parts that are not needed for an interaction with the activator oligonucleotide or the template strand. Such sequence parts for example can bind further oligonucleotides that are used as detection probes or immobilization partners in the binding to the solid phase.

Primer Function of the First Primer Oligonucleotide

The first primer oligonucleotide may be used in several individual steps. First of all, it exerts a primer function in the amplification. Thereby, a primer extension reaction is performed using the second primer extension product as a template. In a further embodiment, the first primer oligonucleotide at the beginning of the amplification reaction can use the start nucleic acid chain as template. In a further embodiment, the first primer oligonucleotide can be used in designing/providing a start nucleic acid chain.

During the amplification the first primer functions as an initiator of the synthesis of the first primer extension product using the second primer extension product as a template. The 3' segment of the first primer comprises a sequence that can mainly complementary bind to the second primer extension product. The enzymatic extension of the first primer oligonucleotide using the second primer extension product as a template results in the formation of the first primer extension product. Such a first primer extension product comprises the target sequence or sequence portions thereof. In the course of the synthesis of the second primer extension product the sequence of the copyable portion of the first primer oligonucleotide is recognized by polymerase as a template and a corresponding complementary sequence is synthesized, so that a respective primer binding site results for the first primer oligonucleotide. Synthesis of the first primer extension product is up to and including the 5' segment of the second primer oligonucleotide. Immediately following synthesis of the first primer extension product said product is bound to the second primer extension product and forms a double-stranded complex. The second primer extension product is sequence-specifically displaced from said complex by the activator oligonucleotide. Thereby, the activator oligonucleotide binds to the first primer extension product. Following a successful strand displacement by the activator oligonucleotide the second primer extension product in turn itself can function as a template for the synthesis of the first primer extension product. The now free 3' segment of the first primer extension product can bind a further second primer oligonucleotide, so that a new synthesis of the second primer extension product can be initiated.

Moreover, the first primer oligonucleotide can function as an initiator of the synthesis of the first primer extension product starting from the start nucleic acid chain at the beginning of the amplification. In one embodiment, the sequence of the first primer is completely complementary to the corresponding sequence segment of a start nucleic acid chain. In a further embodiment, the sequence of the first primer oligonucleotide is only partially complementary to the corresponding sequence segment of a start nucleic acid chain. However, said diverging complementarity is not to prevent the first primer oligonucleotide from starting a mainly sequence-specific primer extension reaction. The respective differences in complementarity of the first primer oligonucleotide to the respective position in the start nucleic acid chain are preferably in the 5' segment of the first region of the first primer oligonucleotide, so that in the 3' segment mainly complementary base pairing and initiation of the synthesis is possible. For the initiation of the synthesis for example especially the first 4-10 positions in the 3' segment are to be completely complementary to the template (start nucleic acid chain). The remaining nucleotide positions may diverge from a perfect complementarity. Thus, the degree of a perfect complementarity in the remaining 5' segment of the first region of the first primer oligonucleotide can comprise ranges between 50% to 100%, better between 80% and 100% of the base composition. According to the length of the first region of the first primer oligonucleotide the sequence divergences are 1 to at most 15 positions, better 1 to at most 5 positions. Thus, the first primer oligonucleotide can initiate a synthesis of a start nucleic acid chain. In a subsequent synthesis of the second primer extension product copyable sequence parts of the first primer oligonucleotide are copied by polymerase, so that in turn in subsequent synthesis cycles a completely complementary primer binding site is formed within the second primer extension product for the binding of the first primer oligonucleotide and is available in subsequent synthesis cycles.

In a further embodiment, the first primer oligonucleotide can be used in the preparation of a start nucleic acid chain. Thereby, such a first primer oligonucleotide can mainly/preferably sequence-specifically bind to a nucleic acid (e.g., a single-stranded genomic DNA or RNA or equivalents thereof comprising a target sequence) and initiate a template-dependent primer extension reaction in the presence of a polymerase. The binding position is selected such that the primer extension product comprises a desired target sequence. Extension of the first primer oligonucleotide results in a nucleic acid strand that has a sequence complementary to a template. Such a strand can be detached from the template (e.g., by heat or alkali) and thus, converted to a single-stranded form. Such a single-stranded nucleic acid chain can function as a start nucleic acid chain at the beginning of the amplification. Such a start nucleic acid chain in its 5' segment comprises the sequence portions of the first primer oligonucleotide, further it comprises a target sequence or equivalents thereof and a primer binding site for the second primer oligonucleotide. Further steps are explained in section "start nucleic acid chain".

The synthesis of the first primer extension product is a primer extension reaction and forms an individual step in the amplification. The reaction conditions during this step are accordingly adapted. Reaction temperature and reaction time are selected such that the reaction can successively take place. The preferred temperature in this step depends on the polymerase used and the binding strength of the respective first primer oligonucleotide to its primer binding site and comprises for example ranges of 15° C. to 75° C., better of 20 to 65° C., preferably of 25° C. to 65° C. The concentration of the first primer oligonucleotide comprises ranges of 0.01 μmol/l to 50 mol/l, better of 0.1 μmol/l to 20 mol/l, preferably of 0.1 μmol/l to mol/l.

In one embodiment, all steps of the amplification proceed under stringent conditions that prevent or delay the formation of non-specific products/by-products. Such conditions are for example higher temperatures, for example above 50° C.

If more than one specific nucleic acid chain is to be amplified in one batch, in one embodiment, preferably sequence-specific primer oligonucleotides are used for amplification of the corresponding target sequences.

Preferably, sequences of the first, the second primer oligonucleotides and of the activator oligonucleotide are adapted to each other such that side reactions, e.g., primer dimer formation, are minimized. For that, for example the sequences of the first and second primer oligonucleotides are adapted to each other such that both primer oligonucleotides are not able to start or support, respectively an amplification reaction in the absence of an appropriate template and/or a target sequence and/or a start nucleic acid chain. This can be achieved for example in that the second primer oligonucleotide does not comprise a primer binding site for the first primer oligonucleotide and the first primer oligonucleotide does not comprise a primer binding site for the second primer oligonucleotide. Moreover, it is to be avoided that the primer sequences comprise extended self-complementary structures (self-complement).

In one embodiment, the synthesis of the first and second primer extension products proceeds at the same temperature. In a further embodiment, the synthesis of the first and second primer extension products proceeds at different temperatures. In a further embodiment, synthesis of the first primer extension product and strand displacement by the activator oligonucleotide proceed at the same temperature. In a further embodiment, synthesis of the first primer extension product and strand displacement by the activator oligonucleotide proceed at different temperatures.

Preferred Embodiments of the Detection System

The detection system comprises at least one fluorescence reporter (reporter) and at least one oligonucleotide probe. Further, a detection system can comprise a fluorescence quencher (referred to as quencher) matching with the fluorescence reporter, so that said quencher is able to reduce the fluorescence signals of the fluorescence reporter under certain circumstances or to reduce the signal intensity. In addition, a detection system can comprise a donor fluorophore matching with the fluorescence reporter, so that said donor fluorophore is able to allow the fluorescence signals of the fluorescence reporter under certain circumstances by energy transfer. In addition, the detection system can comprise the activator oligonucleotide, wherein such an activator oligonucleotide comprises either a fluorescence reporter or a donor fluorophore or a fluorescence quencher.

The arrangement of individual elements (fluorescence reporter, fluorescence quencher, donor fluorophore) on the oligonucleotide probe and/or on the activator oligonucleotide in the presence of a first primer extension product shall result in a change of the fluorescence signal from the fluorescence reporter to form respectively complementary complexes. Said change, depending on the chosen constellation between a fluorescence reporter and/or a donor fluorophore and/or a fluorescence quencher, may result in an increase or decrease of the signal intensity of the fluorescence reporter. Said change can be detected with known suitable means (e.g., in a real-time PCR apparatus, such as StepOne-PCR or Lightcycler or Rotorgene, see particulars of manufacturers) during or after a reaction proceeded. In this way, the detection of the change of the signal can enable conclusions about the course of the reaction: e.g., amplitude of the signal, kinetics, time or concentration dependency of the signal occurrence, respectively. When using several target sequences, multiplex analyses can be coded respectively by different spectral properties, so that also several reactions can be observed in parallel.

In literature, many different arrangements of probes and fluorescence reporters, fluorescence quenchers, and donor fluorophores are known. Also, many fluorescence reporter quenchers as well as fluorescence reporter donor fluorophores (also referred to as donor acceptor pairs or FRET pairs) are known ("Fluorescent Energy Transfer Nucleic Acid Probes" Ed. Didenko, 2006, for example Chapter 1 and 2; Product Description "Fluorescent Molecular Probes", published by Gene Link Inc.). Most probes have been developed for PCR based methods, wherein both specific arrangement of primers, probes and used polymerases, e.g., with 3' exonuclease (FEN) have been used.

The present invention describes some embodiments of oligonucleotide probes that are of particular advantage for the detection of the reaction progress.

The oligonucleotide probe is an oligonucleotide that is preferably built from DNA nucleotides. In another embodiment said oligonucleotide can be built from other nucleotide monomers, e.g., from RNA or nucleotide modifications, e.g., with sugar phosphate backbone modifications, such as PTO or LNA, or 2'-O-Me. In another embodiment said oligonucleotide probe is a mixed polymer which comprises both DNA and non-DNA elements (e.g., RNA, PTO LNA). Said oligonucleotide probe can comprise further oligonucleotide modifications, e.g., linkers or spacers (e.g., C3, HEG, abasic monomers, e.g., THF modification).

The base composition of the oligonucleotide probe preferably comprises bases that can enter into complementary bindings with natural nucleobases (A,C,T,G) under hybridization conditions. In a further embodiment the probe also comprises modifications that comprise for example universal bases (e.g., inosines, 5-nitro-indole). The probe can comprise further modifications that influence the binding behavior of oligonucleotides, e.g., MGB modifications.

The length of the oligonucleotide probe is preferably between 8 and 80 nucleotides, better between 12 and 80 nucleotides, even better between 12 and 50, preferably between 12 and 35 nucleotides.

In one embodiment the 3' end of the oligonucleotide probe is blocked by a modification, e.g., by a fluorophore or quencher or donor or by another modification that hinders polymerase from using the oligonucleotide as a primer (e.g., phosphate residue or C3 linker or dideoxy-nucleotide modification).

In a further embodiment the 3' end of the oligonucleotide probe is free and able to complementary bind with the first primer extension product and to start the synthesis by the polymerase. In this way, the oligonucleotide probe can be extended like a primer what results in the formation of a probe extension product.

In one embodiment the sequence composition corresponds to the probe of the sequence composition of the primer.

The positions of fluorescence reporter, fluorescence quencher or donor fluorophore may be different depending on the embodiment of the oligonucleotide probe. These elements both may covalently be bound to one of the respective ends of the oligonucleotide probe or in the middle region. Many of such modifications are known to the skilled person, for example coupling a FAM reporter to the 3' end or 5' end of a nucleotide, or use of dT-BHQ1 or dT-FAM or dT-TMR modifications for coupling probes in the middle or inner sequence segment of the probe. Such modified oligonucleotide probes can be bought from commercial suppliers (e.g., Sigma-Aldrich, Eurofins, IDT, Eurogentec, Thermofisher Scientific).

Figure 6:
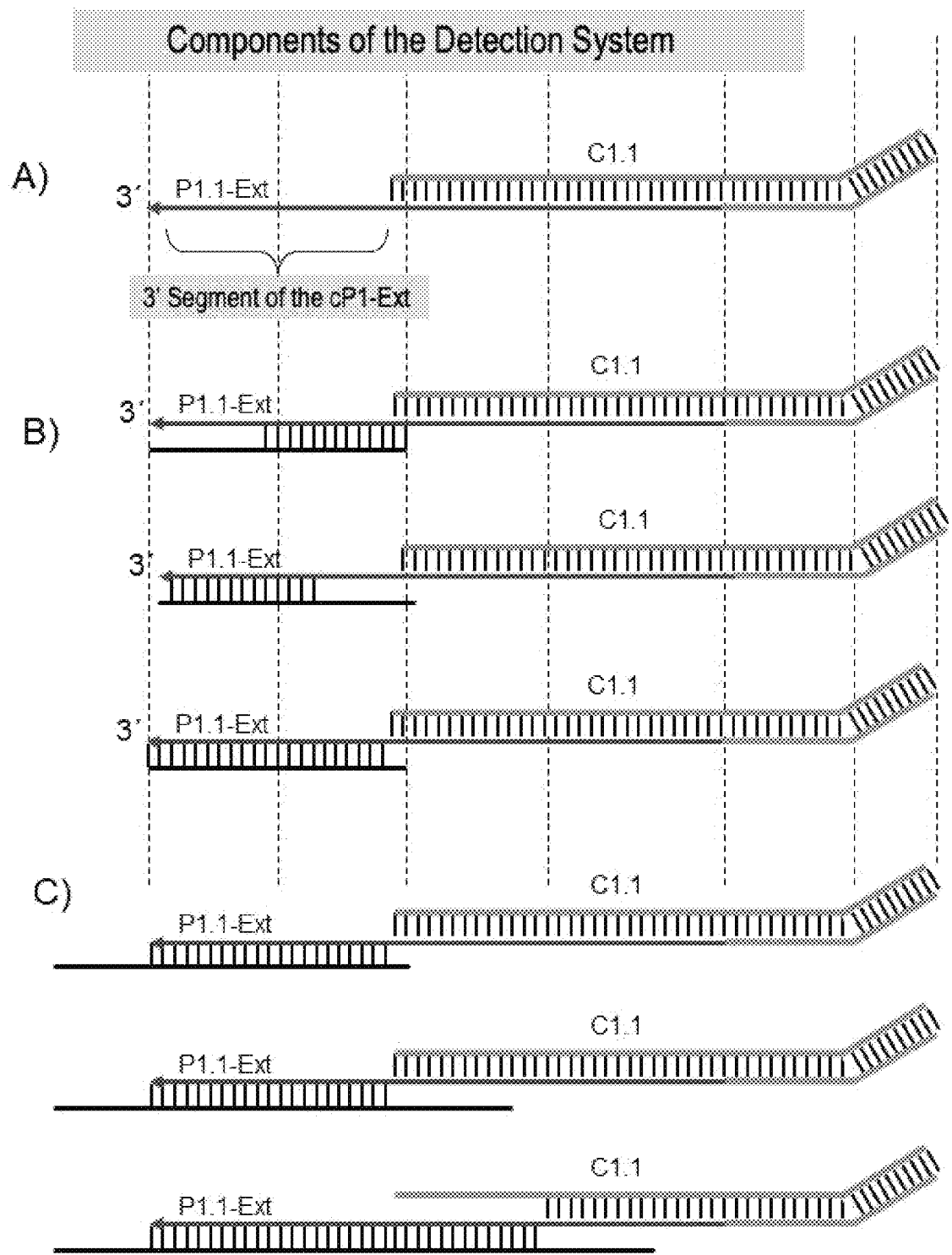

The oligonucleotide probe comprises at least one sequence segment that is able to enter into a substantially complementary binding with the first primer extension product formed during the amplification under suitable reaction conditions of a detection step (FIG. 6A). Here, the oligonucleotide probe at least partially is complementary bound to the single-stranded 3' segment of the synthesized primer extension product (FIG. 6B) that is not bound by the activator oligonucleotide. This way, a complex is generated that comprises a first primer extension product, an oligonucleotide probe, and an activator oligonucleotide. Binding of the oligonucleotide probe and the activator oligonucleotide to the synthesized first primer extension product preferably is sequence-specific. The length of said sequence segment complementary to the 3' segment of the first primer extension product for example is in the range of from 8 to 80 nucleotides, better between 12 and 80 nucleotides, even better between 12 and 50, preferably between 12 and 35 nucleotides, particularly preferred between 15 and 25 nucleotides.

In one embodiment the oligonucleotide probe further comprises additional sequence segments that do not enter into complementary bindings with the first primer extension product. Such sequence segments may be of advantage for example to spatially separate individual components of the detection system (e.g, loop segment 3 and stem segment 2 in FIGS. 2 and 3). Said segments may compete with the activator oligonucleotide for the binding to the first primer extension product (FIG. 6C).

The detection system comprising at least one fluorescence reporter either bound to the oligonucleotide probe or to the activator oligonucleotide is able to change the signal generation or signal intensity of the fluorescence reporter depending on the binding of the oligonucleotide probe to complementary sequences. Depending on the embodiment of the detection system said change can result in a generation and/or an increase or decrease of the signal.

During an amplification, separation of the first and the second primer extension product takes place, so that the 3' segment of the first primer extension product temporarily or permanent is present in the single-stranded form. An oligonucleotide probe can bind to said 3' segment during the reaction or only after its completion.

Binding substantially is sequence-specific, but may also tolerate deviations from complete complementarity.

Binding of the oligonucleotide probe preferably does not hinder amplification. The concentration of the probe and its length are adapted such that a sufficient amount of second primers can also bind to the 3' segment of the first primer extension product during the reaction and thus, can initiate synthesis of the second primer extension product. Generally, there is an excess of the second primer in the reaction batch so that the concentration of the probe is smaller than the concentration of the second primer. For example, the concentration of the probe may be adapted to that of the second primer. The resulting ratio between the second primer and the oligonucleotide probe is preferably in the following ranges (concentration of the probe to concentration of the second primer): from 1:100 to 10:1. Thus, at the same thermodynamic binding properties (e.g., at the same Tm) there is no saturation of the 3' segment of the first primer extension product by the oligonucleotide probe.

With progressing reaction, a sufficient amount of the first primer extension product is formed so that the oligonucleotide probe also can sufficiently bind to cause a detectable signal change.

A suitable detection system comprising at least one fluorescence reporter, also referred to as reporter. Upon excitation of the fluorescence reporter with a suitable light wavelength there is an emission of the fluorescence signal that can be detected with suitable technical means.

A suitable detection system comprising at least one fluorescence reporter in one embodiment further comprises at least one fluorescence quencher matching with the fluorescence reporter. Here, the fluorescence quencher (also referred to as quencher) can develop its function as a contact quencher or as a FRET quencher. Appropriate examples in literature are known ("Fluorescent Energy Transfer Nucleic Acid Probes" Ed. Didenko, 2006, for example Chapter 1 and 2; Product Description "Fluorescent Molecular Probes", published by Gene Link Inc.). For example, fluorescein (FAM) may act as the fluorescence reporter, here as a suitable fluorescence quencher BHQ-1 or BHQ-2 or TAMRA may be mentioned. In one embodiment guanosine nucleobases may be mentioned as quenchers (e.g., in combination with a FAM as reporter). Upon excitation of the fluorescence reporter with a suitable light wavelength in the absence of the quencher emission of the fluorescence signal takes place. However, in case of a spatial proximity between the fluorescence reporter and a suitable quencher a reduction in the intensity of a fluorescence reporter takes place. With increasing distance/separation of the fluorescence reporter and the quencher signal intensity increases.

A further suitable detection system, comprising at least one fluorescence reporter, in one embodiment further comprises at least one donor fluorophore (also referred to as donor) matching with the fluorescence reporter, so that a FRET pair is formed. Appropriate examples in literature are known ("Fluorescent Energy Transfer Nucleic Acid Probes" Ed. Didenko, 2006, for example Chapter 1 and 2; Product Description "Fluorescent Molecular Probes", published by Gene Link Inc.). Generally, a FRET pair comprises a donor and an acceptor (generally a reporter represents the acceptor). For example, tetramethylrodamine (TAMRA) may act as the fluorescence reporter, here as a suitable partner of a FRET pair FAM (donor) may be mentioned, another example is FAM (donor) and Cy3 (as acceptor or reporter). Here, in case of a spatial proximity upon excitation of the donor (e.g., FAM) transfer of energy is to the reporter (TAMRA or Cy3), so that as a result the reporter itself is made able to release energy as electromagnetic radiation (detectable light signal or fluorescence signal, respectively). Said fluorescence signal of the reporter can be detected with suitable means. With increasing spatial separation of the reporter and the donor fluorophore the signal increasingly decreases and generally from a distance of more than 50 nucleotides (measured as 50 nucleotides of a double strand) is no longer detectable in a measurable manner.

By suitably positioning individual elements of the detection system on the oligonucleotide probe and/or the activator oligonucleotide it is possible to detect binding events of said components to the first primer extension product by a signal increase or signal decrease.

Such a detection either can take place during the amplification (e.g., as on-line detection) or in suitable time intervals or also only at the end of a reaction.

In the following some examples of oligonucleotide probes or combinations of oligonucleotide probes and activator oligonucleotides are given.

In one embodiment a suitable detection system comprises the following components (FIG. 2A):

An oligonucleotide probe (S1.1) is an oligonucleotide that comprises a fluorescence reporter (R) and a quencher (Q). In a primarily single-stranded state where the probe is not complementary bound to the sequence the reporter and the quencher are not sufficiently spatially separated so that the fluorescence signal from the reporter is quenched by the quencher. In case of a primarily complementary binding to the 3' segment of a P1-Ext there is a spatial separation of the quencher and the reporter, so that the fluorescence signal increases. Said increase of the signal may be detected during and/or only after the amplification.

In one embodiment a suitable detection system comprises the following components (FIG. 2B):

An oligonucleotide probe (S2.1) is an oligonucleotide that comprises a fluorescence reporter (R) and a quencher (Q). The probe comprises self-complementary sequence elements (stem segment 1 and stem segment 2) which are separated from each other by a loop segment 3. Thus, the probe is constructed as a "molecular beacon", i.e. the probe is constructed such that both stem segments can bind to each other to form a double strand. Quencher and reporter are placed on separate stem segments. In the state where it is not bound to the complementary sequence the "loop segment" of the probe is primarily present in the single-strand state (not bound to the complementary sequence). Here, both complementary stem segments (1 and 2) are able to form a double strand with each other, so that reporter and quencher are not sufficiently spatially separated under the reaction conditions of the detection step and the fluorescence signal from the reporter is substantially reduced by the quencher.

In case of a primarily complementary binding of the "loop segment" 3 to a sequence portion of the 3' segment of a P1-Ext, formation of a double strand between the loop segment 3 and the complementary portion of the 3' segment of the first primer extension product takes place under the used reaction conditions of the detection step what results in a spatial separation of both stem segments and an increase in the distance between the quencher and the reporter. This results in a reduction of the influence of the quencher on the reporter what results in an increase of the fluorescence signal. Said increase of the signal may be detected during the amplification and/or only thereafter.

In one embodiment a suitable detection system comprises the following components (FIG. 3A):

An oligonucleotide probe (S3.1) is an oligonucleotide that comprises a reporter and a quencher. The probe comprises self-complementary sequence elements (stem segment 1 and stem segment 2) that are separated from each other by a loop segment 3. The probe is substantially constructed as a "molecular beacon", i.e. the probe is constructed such that both stem segments can bind to each other to form a double strand. Here, quencher and reporter are placed on separate stem segments. In the state where a "stem segment" of the probe can primarily bind freely to a complementary sequence segment of the other "stem segment", reporter and quencher under the reaction conditions of the detection step are substantially spatially not sufficiently separated and the fluorescence signal from the reporter is reduced by the quencher.

A "stem segment 1" of the probe can enter into a complementary binding with a portion of the 3' segment of the first primer extension product (P1-Ext). Furthermore, the probe comprises a further sequence segment 4, which can form a complementary strand with the 3' segment of the P1-Ext. Said further sequence segment 4 preferably is connected to the stem segment 1 such that both sequence segments can complementary bind to adjacent sequence parts of the 3' segment of a P1-Ext under the reaction conditions of the detection step. In case of a simultaneous primarily complementary binding of the stem segment 1 and sequence segment 4 to the 3' segment of a P1-Ext under the reaction conditions of the detection step there is formed a double strand between the probe and the 3' segment of the first primer extension product. Here, the stem segment 1 takes part in said double strand formation and thus, is no longer available as a binding partner for the stem segment 2. This results in a spatial separation of quencher and reporter, so that the fluorescence signal of the reporter increases. Said increase of the signal may be detected during the amplification and/or only thereafter.

In one embodiment a suitable detection system comprises the following components (FIG. 3B):

An oligonucleotide probe (S4.1) is an oligonucleotide that comprises a reporter and a quencher. The probe comprises self-complementary sequence elements (stem segment 1 and stem segment 2) that are separated from each other by a loop segment 3. The probe is substantially constructed as a "molecular beacon", i.e. the probe is constructed such that quencher and reporter are placed on separate stem segments. In the state at which a "stem segment" of the probe can primarily freely bind to a complementary sequence segment of the other "stem segment", reporter and quencher under the reaction conditions of the detection step are substantially spatially not sufficiently separated and the fluorescence signal from the reporter is substantially quenched by the quencher.

A "stem segment 1" of the probe may enter into a complementary binding with a portion of the 3' segment of the P1-Ext. Furthermore, the probe comprises a further sequence segment 4 which can form a complementary strand with the 3' segment of the P1-Ext and further, said segment 4 can be detected as a primer of polymerase and extended. The sequence of the sequence segment 4 is adapted such that said segment can initiate the synthesis of a complementary strand using the P1-Ext as a template. Said procedure takes place by displacing the activator oligonucleotide out of the binding with the P1-Ext. Here, a primer extension product S4.1-Ext is formed.

In one embodiment the stem segment 1 and/or sequence segment 4 comprises at least one nucleic acid building block that a polymerase cannot copy (e.g., PNA, 2'-O-Me RNA modification or 2'-MOE RNA modifications or linkers, such as C3 or HEG), so that the polymerase cannot use said segments as a template in case of a possible backward synthesis.

In another embodiment the stem segment 1 and sequence segment 4 comprise nucleic acid building blocks that a polymerase can copy (e.g., DNA), so that the polymerase in case of a backward synthesis can use these segments at least partially as a template. It may be of advantage to hinder the polymerase from continuing the synthesis beyond these segments.

For that, for example one or more modifications can be used that are arranged in the middle region of the probe (e.g., between the stem segment 1 and the loop segment 3). Such modifications for example comprise C3 linkers or HEG linkers or other modifications that result in the polymerase stop. Further examples of such modifications are described in section "Embodiments of the first Primer Oligonucleotide".

In one embodiment the loop segment 3 comprises at least one modification not acting as a template for a polymerase and hinders the continuation of the synthesis (e.g., PNA or 2'-O-Me or 2'-MOE) or interrupts the synthesis (e.g., C3 linker or HEG linker).

Preferably, sequence segment 4 at its 5' end is connected to the stem segment 1 such that both sequence segments can complementary bind to the 3' segment of a P1-Ext under the reaction conditions of the detection step. In case of a simultaneous primarily complementary binding of the stem segment 1 and sequence segment 4 to the 3' segment of a P1-Ext, quencher and reporter are spatially separated under the reaction conditions of the detection step, so that the fluorescence signal of the reporter increases. Said increase of the signal can be detected during the amplification and/or only thereafter. This embodiment is illustrated in detail in Example 2.

Figure 4:
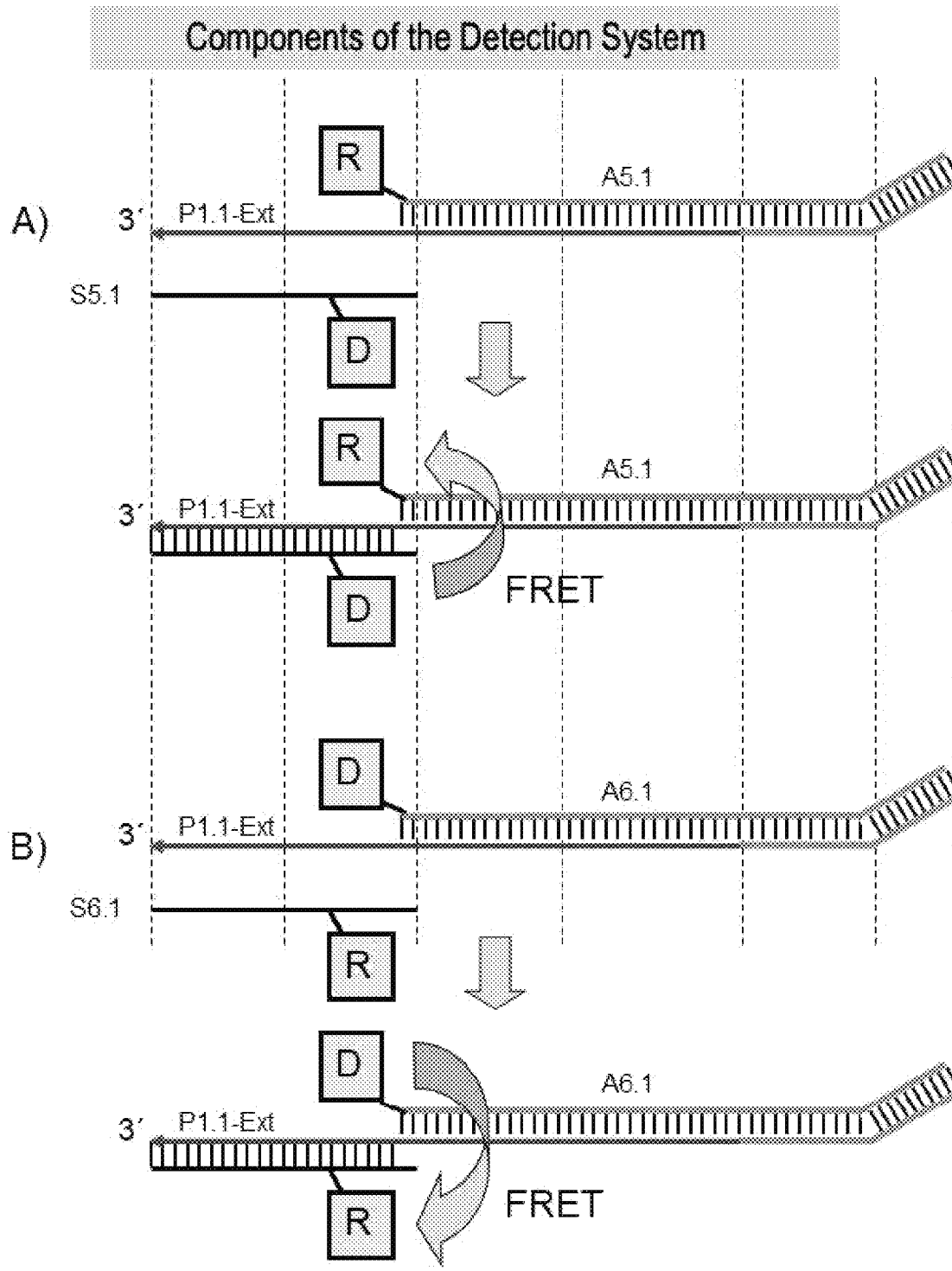

In one embodiment a suitable detection system comprises the following components (FIGS. 4A and 4B): at least one oligonucleotide probe (S5.1) and at least one activator oligonucleotide (A5.1) and further two fluorophores that form a FRET pair. A fluorophore acts as a donor, another as an acceptor (fluorescence reporter). Many FRET pairs or donor acceptor pairs, respectively, are known, e.g. fluoresceine/Cy3. Here, donor and reporter each are separately placed on one of the two oligonucleotides of a specific detection system (often by covalent binding to the respective oligonucleotide) and arranged such that in case of a complementary binding of both oligonucleotides to one and the same first primer extension product there is spatial proximity between the donor and the acceptor (reporter), so that energy transfer from the donor to the reporter can take place and there is a fluorescence signal of the fluorescence reporter that can be detected. Typically, the distance between both components of a FRET pair for successful energy transfer is between 1 to about 20 nucleotides. Here, a partner of the respective FRET pair can be localized in the 5' segment of the activator oligonucleotide. A preferred position is the 5' end of the activator oligonucleotide. Another partner of the FRET pair is located on the oligonucleotide (S5.1), preferably in its middle segment or preferably in the 3' segment.

Under the reaction conditions of the detection step a simultaneous complementary binding of the third region of the activator oligonucleotide and the oligonucleotide (S5.1) to the primer extension product (P1-Ext) takes place. Here, the 5'-standing segment of the activator oligonucleotide and the 3'-standing segment of the oligonucleotide (S5.1) are brought into spatial proximity. Here, excitation of the donor results in an energy transfer to the reporter, wherein a detectable fluorescence signal of the fluorescence reporter is formed. Said increase of the signal can be detected during the amplification and/or only thereafter. Due to a high specificity of the binding of the activator oligonucleotide to the P1-Ext by displacing the complementary P2-Ext the FRET pair is formed with high sequence specificity.

Figure 5:
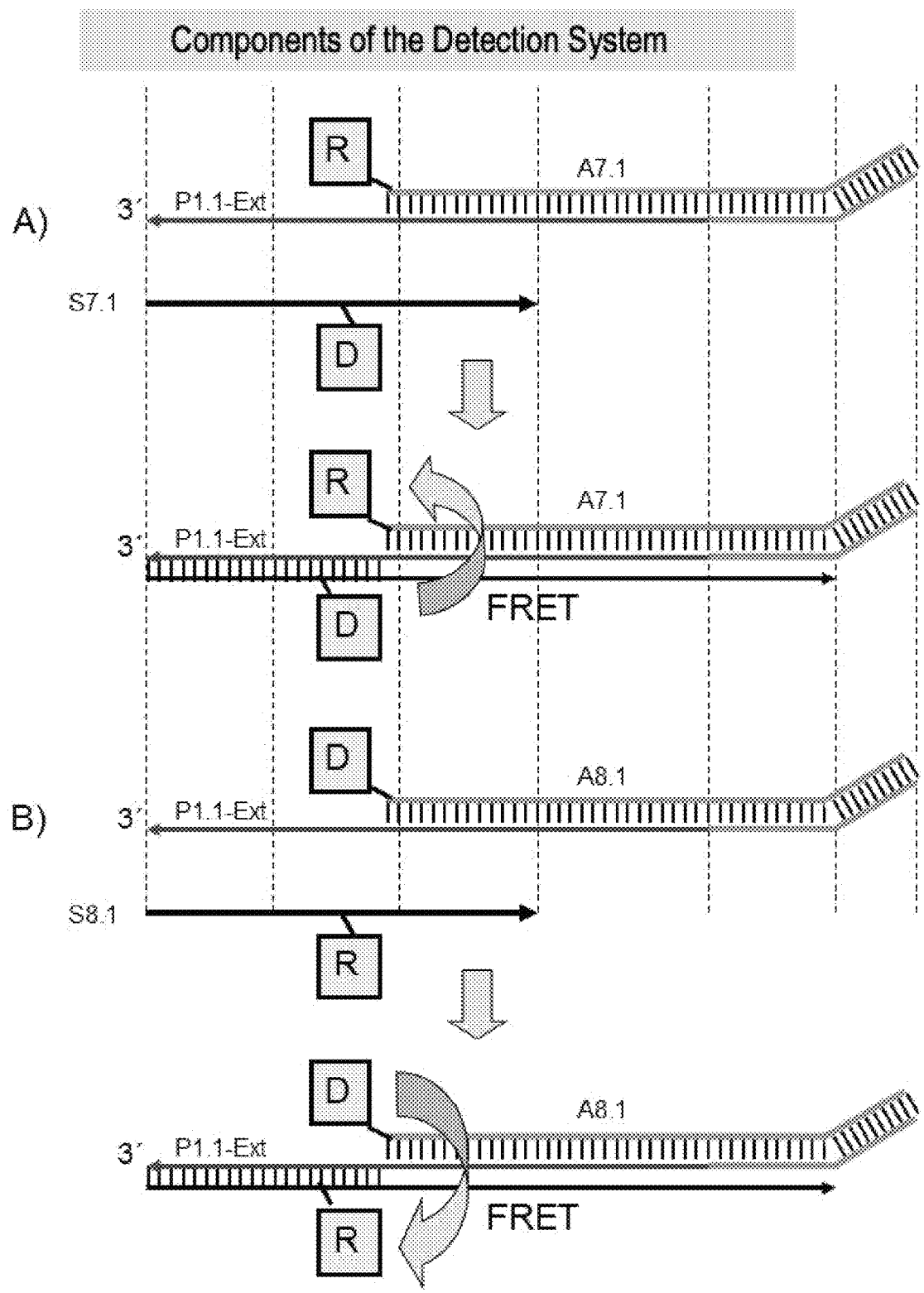

In one embodiment a suitable detection system comprises the following components (FIGS. 5A and 5B): at least one oligonucleotide probe (S7.1 or S8.1, respectively) and at least one activator oligonucleotide (A7.1 or A8.1, respectively) and further two fluorophores that form a FRET pair, similar to illustration 4A and 4B. However, in contrast the used oligonucleotide S7.1 or S8.1 in case of a complementary binding to the P1-Ext may be extended by a polymerase by displacing the activator oligonucleotide, so that thereby an S7.1 extension product (S7.1-Ext) or S8.1 extension product (S8.1-Ext) are generated.

Preferably, no oligonucleotide probes are used that have a "scorpion" structure.

Detection of the fluorescence signal takes place in a detection step. In the detection step of the method it shall be checked whether or not the oligonucleotide probe has complementary bound to the 3' segment of the first primer extension product (P1-Ext). Therefore, in the detection step the reaction temperature is adapted such that the probe would be able to substantially complementary bind to the 3' segment of the first primer extension product. Said temperature either can correspond to one of the temperatures during the amplification or represent a step separate from amplification temperature steps.

During this step the reaction can be excited by a light source of a suitable wavelength. Depending on the design of the detection system the wavelength is adapted to the absorption spectrum of the fluorescence reporter or the donor fluorophore, respectively. If the oligonucleotide probe can bind to the 3' end of a synthesized first primer extension product a signal from the fluorescence reporter is to be expected. Said signal has a characteristic spectrum of wavelengths and may be detected and quantified by a corresponding detection system. Current real-time PCR apparatuses generally comprise both a light source for the excitation and a detection system for the detection of the fluorescence of reporters as well as thermostatable containers for reaction vessels. An example for that represent real-time PCR-apparatuses such as StepOne or LightCycler or RotorGene.

The detection may be used to quantify one or more start nucleic acid chains present in the reaction. Furthermore, the detection may be used to detect an availability of a start nucleic acid chain at the beginning of a reaction. Furthermore, a detection system in connection with an internal amplification control can be used.

In a further embodiment two or more nucleic acid chains can specifically be amplified in an amplification batch. Here, for example combinations of specific first primers and/or specific activator oligonucleotides and/or specific second primers may be used. For example, target sequences and an internal amplification control are amplified in one batch. Thus, it is of advantage to separately and independently perform detection of individual nucleic acid chains during their amplification.

In one embodiment respective specific detection systems are used, so that monitoring of the amplification of a nucleic acid chain is by a respective specific detection system. The respective specific signals from fluorescence reporters may simultaneously be detected. Preferably, the spectral properties of fluorescence reporters differ such that it may take place by detection of respective fluorescence signals at characteristic wavelengths. For example, two or three or four fluorescence reporters may be used. The respective specific wavelengths of fluorescence signals preferably are around more than 10 nm, better around more than 20 nm, preferably around more than 30 nm, measured at the maximum intensity (fluorescence peak) of a fluorescence spectrum). Such combinations are known. For example, combinations comprising FAM and/or Cy3 and/or Cy5 or FAM and/or HEX and/or ROX are suitable. The respective quenchers are preferably specifically selected for each fluorescence reporter, so that signal reduction by a quencher is highly efficient. For example, combinations of FAM/BHQ-1 and HEX/BHQ-2 or FAM/BHQ-1 and Cy5/BHQ-2 are used.

In a further embodiment a detection system may be used that enables monitoring of the amplification of a group of different nucleic acid chains. Here, said group can comprise two or more nucleic acid chains to be amplified. The components of a detection system are correspondingly adapted. In one embodiment such a group of different nucleic acid chains to be amplified for example comprises at least one uniform sequence segment specific for the oligonucleotide probe used to complementary bind an oligonucleotide probe under the reaction conditions of a detection step. In a further embodiment such group of different nucleic acid chains to be amplified for example comprises at least one sequence segment for a primarily complementary binding of an oligonucleotide probe, wherein the sequence composition of said sequence segment is different within said group. Said differences can comprise 1 to 10 nucleotides, preferably 1 to 3 nucleotides.

Preferred Embodiments of the Activator Oligonucleotide

An activator oligonucleotide (FIG. 19) comprises:
a first single-stranded region that can bind to the polynucleotide tail of the second region of the first primer oligonucleotide,
a second single-stranded region that can substantially complementary bind to the first region of the first primer oligonucleotide,
a third single-stranded region that is substantially complementary at least to one segment of the extension product of the first primer extension product,
and the activator oligonucleotide does not function as a template for primer extension of the first or second primer oligonucleotides.

In general, the sequence of the third region of the activator oligonucleotide is adapted to the sequence of the nucleic acid to be amplified, since this is relevant as a template for the order of the nucleotides in the extension product of a first primer. The sequence of the second region of the activator oligonucleotide is adapted to the sequence of the first primer region. The structure of the first region of the activator oligonucleotide is adapted to the sequence of the second region of the first primer oligonucleotide, especially to the nature of the polynucleotide tail.

An activator oligonucleotide can also include further sequence segments that do not belong to the first, second or third regions. These sequences can be attached for example as flanking sequences to the 3' and 5' end. Preferably, these sequence segments do not interfere with the function of the activator oligonucleotide.

The structure of the activator oligonucleotide preferably has the following properties: The individual regions are covalently bound among each other. Binding for example can be via conventional 5'-3' binding. For example, a phosphodiester bond or nuclease-resistant phosphothioester bond may be used.

An activator oligonucleotide can bind to the polynucleotide tail of the first primer oligonucleotide by means of its first region, wherein binding is mainly mediated by hybridizing complementary bases. The length of said first region is 3-80 nucleotides, preferably 4-40 nucleotides, particularly preferred 6-20 nucleotides. The degree of sequence matching between the sequence of the first region of the activator oligonucleotide and the sequence of the second region of the first primer oligonucleotide can be between 20% and 100%, preferably between 50% and 100%, particularly preferred between 80% and 100%. Binding of the first region of the activator oligonucleotide preferably is to be specific to the second region of the first primer oligonucleotide under reaction conditions.

The sequence of the first region of the activator oligonucleotide is preferably selected such that the number of complementary bases that can complementary bind to the second region of the first primer oligonucleotide is between 1 and 40, better between 3 and 20, preferably between 6 and 15.

Since the activator oligonucleotide does not represent a template for polymerase it can include nucleotide modifications that do not support the polymerase function that can be both base modifications and/or sugar phosphate backbone modifications. The activator oligonucleotide in its first region can for example include nucleotide and/or nucleotide modifications that are selected from the following list: DNA, RNA, LNA ("locked nucleic acids" analogues with 2'-4' bridge-type binding in the sugar residue), UNA ("unlocked nucleic acids" without a binding between 2'-3' atoms of the sugar residue), PNA ("peptide nucleic acids" analogues), PTO (phosphorothioate), morpholino analogues, 2'-O-alkyl RNA modifications (such as 2'-OMe, 2'-O propargyl, 2'-O-(2-methoxyethyl), 2'-O-propyl-amine), 2'-halo RNA, 2'-amino RNA etc. These nucleotides or nucleotide modifications are linked to each other for example by a conventional 5'-3' binding or 5'-2' binding. For example, a phosphodiester binding or nuclease-resistant phosphothioester binding can be used.

The activator oligonucleotide in its first region can include nucleotides and/or nucleotide modifications, wherein the nucleobases are selected from the following list: adenine and analogues thereof, guanine and analogues thereof, cytosine and analogues thereof, uracil and analogues thereof, thymine and analogues thereof, inosine or other universal bases (e.g., nitroindole), 2-amino-adenine and analogues thereof, iso-cytosine and analogues thereof, iso-guanine and analogues thereof.

The activator oligonucleotide in its first region can include non-nucleotide compounds that are selected from the following list: intercalating substances that can affect the binding strength between the activator oligonucleotide and the first primer oligonucleotide, e.g., MGB, naphthalene etc. The same elements can also be used in the second region of the first primer.

The activator oligonucleotide in its first region can include non-nucleotide compounds, e.g., linkers such as C3, C6, HEG linkers that can link individual segments of the first region to each other.

The activator oligonucleotide can bind to the first primer region of the first primer oligonucleotide by means of its second region, wherein binding is substantially mediated by the hybridization of complementary bases.

The length of the second region of the activator oligonucleotide is adapted to the length of the first region of the first primer oligonucleotide and preferably corresponds to it. It is between ca. 3-30 nucleotides, preferably between 5 and 20 nucleotides. The sequence of the second region of the activator oligonucleotide is preferably complementary to the first region of the first primer oligonucleotide. The degree of matching in complementarity is between 80% and 100%, preferably between 95% and 100%, preferably 100%. The second region of the activator oligonucleotide preferably includes nucleotide modifications that prevent polymerase in the extension of the first primer oligonucleotide, but do not block or substantially prevent formation of complementary double strands, for example 2'-O-alkyl RNA analogues (e.g., 2'-O-Me, 2'-O-(2-methoxyethyl), 2'-O-propyl, 2'-O-propargyl nucleotide modifications), LNA, PNA or morpholino nucleotide modifications. Individual nucleotide monomers are preferably linked via a 5'-3' binding, but alternatively also a 5'-2' binding between nucleotide monomers can be used.

The sequence length and its nature of the first and second regions of the activator oligonucleotide are preferably selected such that binding of said regions to the first primer oligonucleotide under reaction conditions at least in one reaction step of the method is reversible. That is, that the activator oligonucleotide and the first primer oligonucleotide certainly can specifically bind to each other, but this binding is not to result in the formation of a complex of both elements that is permanently stable under reaction conditions.

Rather, an equilibrium between a bound complex form of activator oligonucleotide and first primer oligonucleotide and a free form of individual components is to be intended or enabled under reaction conditions at least in one reaction step. In this way it is ensured that at least part of the first primer oligonucleotides under reaction conditions is present in a free form and can interact with the template to initiate a primer extension reaction. On the other hand, in this way it is ensured that the respective sequence regions of the activator oligonucleotides are available for binding with an extended primer oligonucleotide.

By selecting the temperature during the reaction the portion of free, single-stranded and thus, reactive components can be affected: by decreasing the temperature first primer oligonucleotides bind to the activator oligonucleotides, so that both participants bind a complementary double-stranded complex. In this way, the concentration of single-stranded forms of individual components can be reduced. An increase of the temperature can result in the dissociation of both components in a single-stranded form. In the range of the melting temperature of the complex (activator oligonucleotide/first primer oligonucleotide) ca. 50% of the components are present in the single-stranded form and ca. 50% as a double-stranded complex. Thus, by using appropriate temperatures the concentration of single-stranded forms in the reaction mixture can be affected.

In embodiments of the amplification method that include a change in temperature between individual reaction steps the desired reaction conditions can be effected during the respective reaction steps. For example, by using temperature ranges of about the melting temperatures of complexes of activator oligonucleotide/first primer oligonucleotide portions of free forms of individual components can be affected. Here, the temperature used results in destabilization of complexes comprising activator oligonucleotide/first primer oligonucleotide, so that during this reaction step individual complex components at least transiently become single-stranded and thus, are enabled to interact with other reaction partners. For example, the first sequence region of the activator oligonucleotide can be released from the double-stranded complex with a non-extended first primer and thus, interact with the second sequence region of an extended first primer oligonucleotide and thus, initiate a strand displacement. On the other hand, the release of a first, non-Extended primer oligonucleotide from a complex comprising activator oligonucleotide/first primer oligonucleotide results in that the first primer region becomes single-stranded and thus, can interact with the template, so that a primer extension by a polymerase can be initiated.

Here, the temperature used must exactly correspond to the melting temperature of the complex of activator oligonucleotide/first primer oligonucleotide. It is sufficient if the temperature in one reaction step is used about in the range of the melting temperature. For example, the temperature in one of the reaction steps comprises ranges of $Tm \pm 10°$ C., better $Tm \pm 5°$ C., preferably $Tm \pm 3°$ C. of the complex of activator oligonucleotide/first primer oligonucleotide.

Such a temperature can be adjusted for example during the reaction step that comprises a sequence-specific strand displacement by the activator oligonucleotide.

In embodiments of the amplification method that do not comprise a change in temperature between individual reaction steps and where amplification proceeds under isothermal conditions reaction conditions are maintained for the entire duration of the amplification reaction under which an equilibrium between a complex form of activator oligonucleotide and the first primer oligonucleotide and a free form of individual components is possible.

The ratio between a complex form of activator oligonucleotide and the first primer oligonucleotide and free forms of individual components can be affected both by reaction conditions (e.g., temperature and $Mg^{2+}$ concentration) and by the structures and concentrations of the individual components.

The sequence length and its nature of the first and second region of the activator oligonucleotide in one embodiment are selected such that under given reaction conditions (e.g., in the reaction step of a strand displacement by the activator oligonucleotide) the ratio between a portion of a free activator oligonucleotide and a portion of an activator oligonucleotide in a complex with a first primer oligonucleotide comprises the following ranges: of 1:100 to 100:1, preferably of 1:30 to 30:1, particularly preferred of 1:10 to 10:1. The ratio between a portion of a free first primer oligonucleotide and a portion of a first primer oligonucleotide in a complex with an activator oligonucleotide comprises ranges of 1:100 to 100:1, preferably of 1:30 to 30:1, particularly preferred of 1:10 to 10:1.

In one embodiment, the concentration of the first primer oligonucleotide is higher than the concentration of the activator oligonucleotide. In this way, there is an excess of the first primer in the reaction and the activator oligonucleotide, for its effect, has to be released from the binding with the first primer by selecting appropriate reaction temperatures. In general, this is done by raising the temperature until sufficient concentrations of free forms of the activator oligonucleotide are present.

In a further embodiment, the concentration of the first primer oligonucleotide is lower than the concentration of the activator oligonucleotide. In this way, there is an excess of the activator oligonucleotide and the first primer oligonucleotide, for its effect, has to be detached from the binding with the activator oligonucleotide by selecting appropriate reaction temperatures. In general, this is done by raising the temperature until sufficient concentrations of free forms of the first primer oligonucleotide are present.

With isothermal conditions there is an equilibrium: certain portions of the first primer oligonucleotide and activator oligonucleotide are bound to each other, whereas others are present as a single-stranded form in the reaction.

The activator oligonucleotide can bind to at least one segment of the specifically synthesized extension product of the first primer oligonucleotide by means of its third region. Binding is preferably done by the hybridization of complementary bases between the activator oligonucleotide and the extension product synthesized by polymerase.

In order to support the strand displacement reaction the sequence of the third region preferably is to have a high complementarity to the extension product. In one embodiment, 100% of the sequence of the third region is complementary to the extension product.

Preferably, the third region binds to the segment of the extension product that immediately follows the first region of the first primer oligonucleotide. Thus, the segment of the extension product preferably is in the 5' segment of the total extension product of the first primer oligonucleotide.

Preferably, the third region of the activator oligonucleotide is not bound over the entire length of the extension product of the first primer oligonucleotide. Preferably, one segment at the 3' end of the extension product remains unbound. Said 3'-terminal segment is needed for the binding of the second primer oligonucleotide.

The length of the third region is accordingly adapted such that the third region binds to the 5'-standing segment of the extension product, but does not bind the 3'-standing segment of the extension product.

The total length of the third region of the activator oligonucleotide is 2 to 100, preferably 6 to 60, particularly preferred 10 to 40 nucleotides or equivalents thereof. The activator oligonucleotide can complementary bind to the segment of the extension product over this length and thus, displace this 5'-standing segment of the extension product from the binding with its complementary template strand.

The length of the 3'-standing segment of the extension product that is not bound by the activator oligonucleotide comprises for example ranges between 5 and 200 nucleotides, better between 5 and 100, much better 5 and 60, preferably between 10 and 40, preferably between 15 and 30 nucleotides.

The oligonucleotide probe can complementary bind to said 3' segment of the first primer extension product. Here, the binding may be either over the whole length of said fragment or also claim only a part of the fragment for the binding.

Said 3'-standing segment of the extension product is not displaced by the activator oligonucleotide from the binding with the template strand. Also in case of a completely bound third region of the activator oligonucleotide to its complementary segment of the extension product the first primer extension product can remain bound with the template strand via its 3'-standing segment. The binding strength of said complex is preferably selected such that it can for example spontaneously dissociate under reaction conditions (step e)). This can be achieved for example in that the melting temperature of said complex of the 3'-standing segment of the extension product of the first primer oligonucleotide and its template strand is about in the range of the reaction temperature or below the reaction temperature in a respective reaction step (reaction step e). In case of a low stability of said complex in the 3' segment of the extension product a complete binding of the third region of the activator oligonucleotide to the 5'-standing segment of the extension product results in a rapid dissociation of the first primer extension product from its template strand.

Altogether, the activator oligonucleotide has an appropriate structure to exert its function: under the respective reaction conditions it is able to sequence-specifically displace the extended first primer oligonucleotide from the binding with the template strand, whereby the template strand is converted to the single-stranded form and thus, is available for further bindings with a new first primer oligonucleotide and its target sequence-specific extension by polymerase.

In order to fulfill the function of the strand displacement the regions one, two and three of the activator oligonucleotide are mainly to be present in the single-stranded form under reaction conditions. Hence, double-stranded self-complementary structures (e.g., hairpins) in these regions are to be avoided, if possible, since they can lower the functionality of the activator oligonucleotide.

In the method according to the invention the activator oligonucleotide is not to be present as a template, hence the first primer oligonucleotide, when attached to the activator oligonucleotide under reaction conditions, is not to be extended by polymerase.

This is preferably achieved by the use of nucleotide modifications that prevent polymerase from copying the strand. Preferably, the 3' end of the first primer oligonucleotide remains unextended if the first primer oligonucleotide binds to the activator oligonucleotide under reaction conditions.

The extent of blockage/hindrance/deceleration/complication of the reaction can be between a full expression of this property (e.g., 100% blockage under given reaction conditions) and a partial expression of this property (e.g., 30-90% blockage under given reaction conditions). Preferred are nucleotide modifications that alone or coupled in series (e.g., as a sequence fragment consisting of modified nucleotides) can prevent the extension of a first primer more than 70%, preferably more than 90%, more preferably more than 95%, and particularly preferred 100%.

The nucleotide modifications can comprise base modifications and/or sugar phosphate residue modifications. Sugar phosphate modifications are preferred, since by a combination with conventional nucleobases an arbitrary complementary sequence of an activator oligonucleotide can be arranged. The nucleotide with modifications in the sugar phosphate residue that can result in the hindrance or blockage of the synthesis of the polymerase, for example includes: 2'-O-alkyl modifications (e.g., 2'-O-methyl, 2'-O-(2-methoxyethyl), 2'-O-propyl, 2'-O-propargyl nucleotide modifications), 2'-amino-2'-deoxy-nucleotide modifications, 2'-amino-alkyl-2'-deoxy-nucleotide modifications, PNA, morpholino modifications etc.

Blockage can be both by a single nucleotide modification or only by coupling several nucleotide modifications in series (e.g., as a sequence fragment consisting of modified nucleotides). For example, at least 2, preferably at least 5, particularly preferred at least 10 of such nucleotide modifications can be coupled next to each other in the activator oligonucleotide.

An activator oligonucleotide can have a uniform type of nucleotide modifications or comprise at least two different types of nucleotide modification.

The position of such nucleotide modifications in the activator oligonucleotide preferably is to prevent the polymerase from extending the 3' end of a first primer oligonucleotide bound to the activator oligonucleotide.

In one embodiment, such nucleotide modifications are located in the second region of the activator oligonucleotide. In a further embodiment, such nucleotide modifications are located in the third region of the activator oligonucleotide. In a further embodiment, such nucleotide modifications are located in the second and in the third regions of the activator oligonucleotide.

For example, at least 20%, preferably at least 50% of the positions of the second region of the activator oligonucleotide consist of such nucleotide modifications.

For example, at least 20%, preferably at least 50%, particularly preferred at least 90% of the positions of the third region of the activator oligonucleotide consist of such nucleotide modifications. In one embodiment the whole third region comprises nucleotide modifications which hinder a polymerase from extending a primer bound to such a region using the activator oligonucleotide as a template. In a further embodiment the whole third and second regions comprise such nucleotide modifications. In a further embodiment the whole first, second, and third regions comprise such nucleotide modifications. Thus, the activator oligonucleotide can completely consist of such nucleotide modifications. For example, such modified activator oligonucleotides may be used in multiplex analyses in which further primers are used. In this way, it is to be prevented that unintentional primer extension reactions on one or more activator oligonucleotides occur.

The sequence of the nucleobases of these nucleotide modifications is adapted to the demands on the sequence in the respective region.

The rest are for example natural nucleotide or nucleotide modifications that do not hinder polymerase function at all or only marginally, e.g., DNA nucleotides, PTO nucleotides, LNA nucleotides, RNA nucleotides. Here, further modifications, for example base modifications such as 2-aminoadenosine, 2-aminopurines, 5-methyl-cytosines, inosines, 5-nitroindoles, 7-deaza-adenosine, 7-deaza-guanosine, 5-propyl-cytosine, 5-propyl-uridine or non-nucleotide modifications such as dyes, or MGB modifications etc. can be used e.g., to adjust binding strength of individual regions of the activator oligonucleotide. The individual nucleotide monomers can be coupled to each other via a conventional 5'-3' binding or also else via a 5'-2' binding.

A segment of the activator oligonucleotide with nucleotide modifications that prevent an extension of the 3' end of a first primer oligonucleotide bound to an activator oligonucleotide by polymerase is referred to as "second blocking unit". The length of said segment can include between 1 to 50 nucleotide modifications, preferably between 4 and 30. Said segment can be located in the activator oligonucleotide for example such that the 3' end of the bound first primer oligonucleotide is in this segment. Thus, this segment can span regions two and three.

In one embodiment, preferably no linker structures or spacer structures such as C3, C6, HEG linkers are used to prevent extension of the 3' end of a first primer oligonucleotide bound to the activator oligonucleotide.

In one embodiment an activator oligonucleotide in its third region comprises at least one component of the detection system (e.g., fluorescence reporter or fluorescence quencher or a donor fluorophore). The position of said component in one embodiment is at the 5' end of the activator oligonucleotide. In another embodiment said component lies in the inner sequence segment of the third region. Here, the distance up to the 5' end of the activator oligonucleotide may be between 2 and 50 nucleotides, better between 2 and 20, preferably between 2 and 10 nucleotides. Here, in case of a simultaneous binding of the oligonucleotide probe and the activator oligonucleotide to the same first primer extension product a spatial proximity of both components of the detection system (e.g., between a fluorescence reporter on the oligonucleotide probe and a donor fluorophore on the activator oligonucleotide).

The activator oligonucleotide in addition to regions one, two and three can also comprise further sequence segments that flank the above-mentioned regions for example in the 5' segment or 3' segment of the activator oligonucleotide. Such sequence elements can be used for example for further functions such as for example interaction with probes, binding to solid phase etc. Such regions preferably do not interfere with the function of regions one to three. The length of these flanking sequences may be for example between 1 to 50 nucleotides. Moreover, an activator oligonucleotide can comprise at least one element for immobilization to a solid phase, e.g., a biotin residue. Moreover, an activator oligonucleotide can comprise at least one element for detection, e.g., a fluorescent dye.

In the presence of an activator oligonucleotide re-synthesized sequences are examined in view of their sequence contents by interaction with the activator oligonucleotide.

In case of a correct matching with given sequence contents of the activator oligonucleotide strand displacement occurs, wherein the template strands are replaced by re-synthesized strands. Thereby, primer binding sites are converted to a single-stranded state and are available for a new interaction with primers and thus, for a further synthesis. Thus, the system of both primer extension products is put into an active state. Thus, the activator oligonucleotide has an activating effect on the system.

In case of a lacking matching with given sequence contents of the activator oligonucleotide strand displacement of the template strands of re-synthesized strands is affected. Strand displacement and/or detachment either is quantitatively decelerated or completely cancelled. Thus, primer binding sites are not converted to the single-stranded state at all or less often. Thus, no primer binding sites at all or quantitatively less are available for a new interaction with primers. Thus, the system of both primer extension products is less often put into an active state or an active state is not achieved at all.

Efficacy of the double strand opening of the re-synthesized primer extension products after each single synthesis step has an effect on the potentially obtainable yields in subsequent cycles: the less free/single-stranded primer binding sites are provided to a nucleic acid chain to be amplified at the beginning of a synthesis step, the smaller is the number of re-synthesized strands of the nucleic acid chain to be amplified in this step. In other words: The yield of a synthesis cycle is proportional to the amount of primer binding sites that are available for the interaction with the corresponding complementary primers. Altogether, in this way a control loop can be realized.

Said control loop corresponds to a real-time/on-line control of synthesized fragments: sequence control is performed in the reaction mixture while the amplification takes place. Said sequence control is performed in accordance with a given pattern and the oligonucleotide system (by a strand-opening effect of the activator oligonucleotide) is able to distinguish between "correct" and "incorrect" states without external interventions. In the correct state the synthesis of sequences is continued, in the incorrect state synthesis is either decelerated or completely prevented. The resulting differences in the yields of "correct" and "incorrect" sequences after each step have an effect on the whole amplification that comprises a number of such steps.

In an exponential amplification said dependency is exponential, so that even minor divergences in efficacy in one single synthesis cycle due to sequence divergences can mean a significant delay in time of the whole amplification or cause a complete absence of a detectable amplification in a given time frame.

This effect of the real-time control of the re-synthesized nucleic acid chains is associated with the employment of the activator oligonucleotide and thus, the influence of the activator oligonucleotide during an amplification significantly goes beyond the length of primer oligonucleotides.

Reaction Conditions at Strand Displacement Reaction

The displacement of the second primer extension product from the binding with the first primer extension product by means of a sequence-dependent strand displacement by the activator oligonucleotide forms an individual step in the amplification. The reaction conditions during said step are accordingly adapted. Reaction temperature and reaction time are selected such that the reaction can successfully take place.

In a preferred embodiment strand displacement by the activator oligonucleotide is up to detachment/dissociation of the second primer extension product from the binding with the first primer extension product. Such a dissociation of the 3' segment of the first primer extension product of complementary portions of the second primer extension product can be spontaneous during a temperature-dependent/temperature-related separation of both primer extension products. Such a dissociation has a favorable effect on the kinetics of the amplification reaction and can be affected by the choice of the reaction conditions, e.g., by means of temperature conditions. Therefore, temperature conditions are selected such that a successful strand displacement by complementary binding of the activator oligonucleotide favors a dissociation of the second primer extension product from the 3' segment of the first primer extension product.

In a further preferred embodiment strand displacement by the activator oligonucleotide proceeds up to the detachment/dissociation of a 3' segment of the second primer extension product (P2.1-Ext) from the complementary binding with the first primer extension product (P1.1-Ext), wherein said 3' segment of the second primer extension product (P2.1-Ext) comprises at least one complementary region to the first primer and a complementary segment to the first primer extension product (P1.1-Ext), which has only been formed in the enzymatic synthesis. Here, a complex (C1.1/P1.1-Ext/P2.1.-Ext) is formed, which comprises both the first primer extension product (P1.1-Ext), the second primer extension product (P2.1-Ext) as well as the activator oligonucleotide (C1.1). In such a complex the 3' segment of the second primer extension product at least temporarily is present in a single-stranded form, since it can be displaced from binding with the first primer extension product by the activator oligonucleotide. Schematically illustrated there is a balance between the binding and detachment of the P2.1-Ext to and from the P1.1-Ext. The 3' segment of the first primer extension product (P1.1-Ext) in such a complex is present complementary hybridized to the second primer extension product (P2.1-Ext).

Due to a temporary or partially free primer binding site for the first primer oligonucleotide (3' segment of the second primer extension product) a new primer extension product (P1.2) can bind to said single-stranded sequence segment of the (P2.1-Ext), which is still in the complex, under reaction conditions and thus, initiate a synthesis of a new first primer extension product (P1.2-Ext) by a polymerase. Generally, initiation of said reaction proceeds with reduced efficiency, since the 3' segment of the P2.1-Ext is not permanently present in the single-stranded form, but is in a competitive behavior with the activator oligonucleotide and thus, alternatingly has single-stranded and double-stranded states by the binding to the P1.1-Ext.

Continuation of said re-started synthesis of P1.2-Ext using the second primer extension product as a template (P2.1-Ext) may also contribute to the dissociation of the complexes (C1.1/P1.1-Ext/P2.1.-Ext) by strand displacement associated with polymerase. Here, activator oligonucleotide, temperature-dependent double strand destabilization and strand displacement by the polymerase act synergistically and complementary. The result is a dissociation of the 3' segment of the first primer extension product (P1.1-Ext) from complementary portions of the second primer extension product (P2.1-Ext).

Such a dissociation has a favorable effect on the kinetics of the amplification reaction and may be influenced by the choice of the reaction conditions, e.g., by means of temperature conditions. Contribution of the polymerase-mediated synthesis-depending strand displacement to the dissociation of P1.1-Ext and P2.1-Ext has a favorable effect in strand separation.

The temperature in this step comprises for example ranges of 15° C. to 75° C., better of 30° C. to 70° C., preferably of 50° C. to 70° C.

With a given length of the first region of the activator oligonucleotide and the second region of the first primer oligonucleotide (comprising for example ranges of 3 to 25 nucleotide monomers, better of 5 to 15 nucleotide monomers) a strand displacement reaction generally can successfully be initiated. In case of a complete complementarity of the activator oligonucleotide to the respective portions of the first primer extension product the activator oligonucleotide can bind to the first primer extension product except for the 3' segment of the first primer extension product and displace the second primer extension product. Thus, the second primer extension product remains connected to the 3' segment of the first primer extension product. The strength of said connection can be affected depending on temperature. When reaching a critical temperature this connection can disintegrate and both primer extension products can dissociate. The shorter the sequence of the 3' segment, the more instable the connection and the lower the temperature that causes a spontaneous dissociation.

A spontaneous dissociation can for example be achieved in the temperature range that is about the melting temperature. In one embodiment, the temperature of the steps of strand displacement by the activator oligonucleotide is about at the melting temperature (Tm±3° C.) of the complex comprising the 3' segment of the first primer extension product that is not bound by the activator oligonucleotide and the second primer oligonucleotide or the second primer extension product, respectively.

In one embodiment, the temperature of the steps of strand displacement by the activator oligonucleotide is at about the melting temperature (Tm±5° C.) of the complex comprising the 3' segment of the first primer extension product that is not bound by the activator oligonucleotide and the second primer oligonucleotide or the second primer extension product, respectively.

In one embodiment, the temperature of the steps of strand displacement by the activator oligonucleotide is above the melting temperature of the complex comprising the 3' segment of the first primer extension product that is not bound by the activator oligonucleotide and the second primer oligonucleotide or the second primer extension product, respectively. Such a temperature comprises temperature ranges of about Tm+5° C. to Tm+20° C., better of Tm+5° C. to Tm+10° C. By using a higher temperature the equilibrium in said reaction step can be shifted toward dissociation. Thereby, the kinetics of the reaction can favorably be influenced. Using too low temperatures in the step of strand displacement by means of the activator oligonucleotide can lead to a significant deceleration of the amplification.

In one embodiment, a first primer extension product comprises a 3' segment that is not bound by the activator oligonucleotide and that comprises sequence lengths of 9 to about 18 nucleotides. In this embodiment, a spontaneous dissociation in general can already be achieved with temperature ranges between 40° C. and 65° C. Also higher temperatures lead to dissociation.

In one embodiment, a first primer extension product comprises a 3' segment that is not bound by the activator oligonucleotide and that comprises sequence lengths of 15 to about 25 nucleotides. In this embodiment, a spontaneous dissociation in general can already be achieved with temperature ranges between 50° C. and 70° C. Also higher temperatures lead to dissociation.

In one embodiment, a first primer extension product comprises a 3' segment that is not bound by the activator oligonucleotide and that comprises sequence lengths of 20 to about 40 nucleotides. In this embodiment, a spontaneous dissociation in general can already be achieved with temperature ranges between 50° C. and 75° C. Also higher temperatures lead to dissociation.

The composition of the 3' segment of the first primer extension product and optionally adding melting temperature-affecting oligonucleotide modifications (e.g., MGB) or reaction conditions (e.g., TPAC, betaines) can have effect on the choice of the temperature. A corresponding adjustment can therefore be made.

In one embodiment, all steps of the amplification proceed under stringent conditions that prevent or decelerate the formation of non-specific products/by-products. Such conditions are for example higher temperatures, for example above 50° C.

In one embodiment, the individual steps of strand displacement by the activator oligonucleotides proceed at the same temperature such as the synthesis of the first and second primer extension products. In a further embodiment, the individual steps of strand displacement by the activator oligonucleotides proceed at a temperature that differs from the temperature of the respective synthesis of the first and second primer extension products. In a further embodiment, the synthesis of the first primer extension product and strand displacement by the activator oligonucleotide proceed at the same temperature. In a further embodiment, synthesis of the second primer extension product and strand displacement by the activator oligonucleotide proceed at the same temperature.

The concentration of the activator oligonucleotide comprises ranges of 0.01 µmol/l to 50 µmol/l, better of 0.1 µmol/l to 20 µmol/l, preferably of 0.1 µmol/l to 10 µmol/l.

Preferred Embodiments of the Second Primer Oligonucleotide (Primer 2):

An oligonucleotide that with its 3' segment is able to bind to a substantially complementary sequence within the nucleic acid to be amplified or equivalents thereof and to initiate a specific second primer extension reaction (FIG. 22 to 25). This second primer oligonucleotide thus is able to bind to the 3' segment of a first specific primer extension product of the first primer oligonucleotide and to initiate a polymerase-dependent synthesis of a second primer extension product. In one embodiment, each second primer oligonucleotide is specific for one nucleic acid to be amplified each.

The second primer oligonucleotide is to be copyable upon backward synthesis and also functions as a template itself during the synthesis of the first primer extension product.

The length of the second primer oligonucleotide can be between 15 and 100 nucleotides, preferably between 20 and 60 nucleotides, particularly preferred between 30 and 50 nucleotides. The nucleotide building blocks are preferably linked to each other via common 5'-3' phosphodiester binding or phosphothioester binding. Such a primer oligonucleotide can be chemically synthesized in the desired manner.

In one embodiment, the second primer oligonucleotide can include nucleotide monomers that do not or only insignificantly influence the function of polymerase, these are for example:
natural nucleotides (dA, dT, dC, dG etc.) or their modifications without changed base pairing
modified nucleotides, 2-amino-dA, 2-thio-dT or other nucleotide modifications with diverging base pairing (e.g., universal base pairs such as for example inosine 5-nitroindole).

In a preferred embodiment, the 3'-OH end of this region is preferably free from modifications and has a functional 3'-OH group that is recognized by polymerase and can be extended dependent on a template. In a further preferred embodiment, the 3' segment of the second primer comprises at least one phosphorothioate compound, so that the 3' end of the primer cannot be degraded by the 3' exonuclease activity of polymerases.

The second primer oligonucleotide can be used in several individual steps. First, it exerts a primer function in the amplification. Thereby, a primer extension reaction using the first primer extension product as a template is performed. In a further embodiment, the second primer oligonucleotide can use the start nucleic acid chain as a template at the beginning of the amplification reaction. In a further embodiment, the second primer oligonucleotide can be used in designing/providing a start nucleic acid chain.

During the amplification the second primer functions as an initiator of the synthesis of the second primer extension product using the first primer extension product as a template. The 3' segment of the second primer comprises a sequence that can mainly complementary bind to the first primer extension product. The enzymatic extension of the second primer oligonucleotide using the first primer extension product as a template leads to the formation of the second primer extension product. Such a synthesis typically takes place in parallel to the displacement of the activator oligonucleotide from its binding with the first primer extension product. Said displacement mainly is by polymerase and can partially be done by the second primer oligonucleotide. Such a second extension product comprises the target sequence or segments thereof. In the course of the synthesis of the second primer extension product the sequence of the copyable portion of the first primer oligonucleotide is recognized by polymerase as template and a respective complementary sequence is synthesized. Said sequence is in the 3' segment of the second primer extension product and comprises a primer binding site for the first primer oligonucleotide. The synthesis of the second primer extension product is up to the stop position in the first primer oligonucleotide. Immediately after the synthesis of the second primer extension product this product is bound to the first primer extension product and forms a double-stranded complex. The second primer extension product is sequence-specifically displaced from said complex by the activator oligonucleotide. After a successful strand displacement by the activator oligonucleotide the second primer extension product itself in turn can function as a template for the synthesis of the first primer extension product.

Moreover, the second primer oligonucleotide can function as an initiator of the synthesis of the second primer extension product starting from the start nucleic acid chain at the beginning of the amplification. In one embodiment, the sequence of the second primer is completely complementary to the corresponding sequence segment of a start nucleic acid chain. In a further embodiment, the sequence of the second primer oligonucleotide is only partially complementary to the corresponding sequence segment of a start nucleic acid chain. However, said diverging complementarity is not to prevent the second primer oligonucleotide from starting a mainly sequence-specific primer extension reaction. The respective divergences in complementarity of the second primer oligonucleotide to the respective position in the start nucleic acid chain are preferably in the 5' segment of the second primer oligonucleotide, so that in the 3' segment mainly complementary base pairing and initiation of the synthesis are possible. For the initiation of the synthesis for example particularly the first 4-10 positions in the 3' segment are to be fully complementary to the template (start nucleic acid chain). The remaining nucleotide positions can diverge from perfect complementarity. Thus, the degree of a perfect complementarity in the 5' segment can comprise ranges of 10% to 100%, better between 30% and 100% of the base composition. Depending on the length of the second primer oligonucleotide these divergences from a full complementarity in the 5' segment comprise from 1 to 40, better 1 to 20 nucleotide positions. In a further embodiment, the second primer oligonucleotide binds to the start nucleic acid chain only with its 3' segment, but not with its 5' segment. The length of such a 3' segment of the second primer oligonucleotide that is completely complementary to the start nucleic acid chain comprises ranges between 6 and 40 nucleotides, better between 6 and 30 nucleotides, preferably between 6 and 20. The length of a corresponding 5' segment of the second primer oligonucleotide that is non-complementary to the start nucleic acid chain comprises ranges between 5 and 60, better between 10 and 40 nucleotides. Thus, the second primer oligonucleotide is able to initiate the synthesis of a start nucleic acid chain. In a subsequent synthesis of the first primer extension product sequence parts of the second primer oligonucleotide are copied by polymerase, so that in turn in subsequent synthesis cycles a completely complementary primer binding site is formed within the first primer extension product for binding of the second primer oligonucleotide and is available in subsequent synthesis cycles.

In a further embodiment, the second primer oligonucleotide can be used during the preparation of a start nucleic acid chain. Here, such a second primer oligonucleotide can mainly/preferably sequence-specifically bind to a nucleic acid (e.g., a single-stranded genomic DNA or RNA or equivalents thereof comprising a target sequence) and initiate a template-depending primer extension reaction in the presence of a polymerase. The binding position is selected such that the primer extension product comprises a desired target sequence. Extending the second primer oligonucleotide results in a strand that has a sequence complementary to the template. Such a strand can be detached by the template (e.g., by heat or alkali) and so converted into a single-stranded form. Such a single-stranded nucleic acid chain can function as a start nucleic acid chain at the beginning of the amplification. Such a start nucleic acid chain comprises in its 5' segment the sequence portions of the second primer oligonucleotide, moreover it comprises a target sequence or equivalents thereof and a primer binding site for the first primer oligonucleotide. Further steps are explained in section "start nucleic acid chain".

In a preferred embodiment, the second primer oligonucleotide at least in its 3' segment comprises sequence portions that can complementary and sequence-specifically bind to a sequence segment of a target sequence and initiate/support a successful primer extension reaction by polymerase. The length of such a sequence segment comprises ranges of 6 and 40 nucleotides, better of 8 to 30 nucleotides, preferably of 10 to 25 nucleotides.

In one embodiment, the second primer oligonucleotide in its 3' and 5' segment comprises copyable sequence parts that are copied by polymerase in the synthesis of the first primer extension product. Thus, all sequence parts of the second primer are copied by polymerase. This leads to the formation of a primer binding site in the 3' segment of the first primer extension product.

Figure 24:
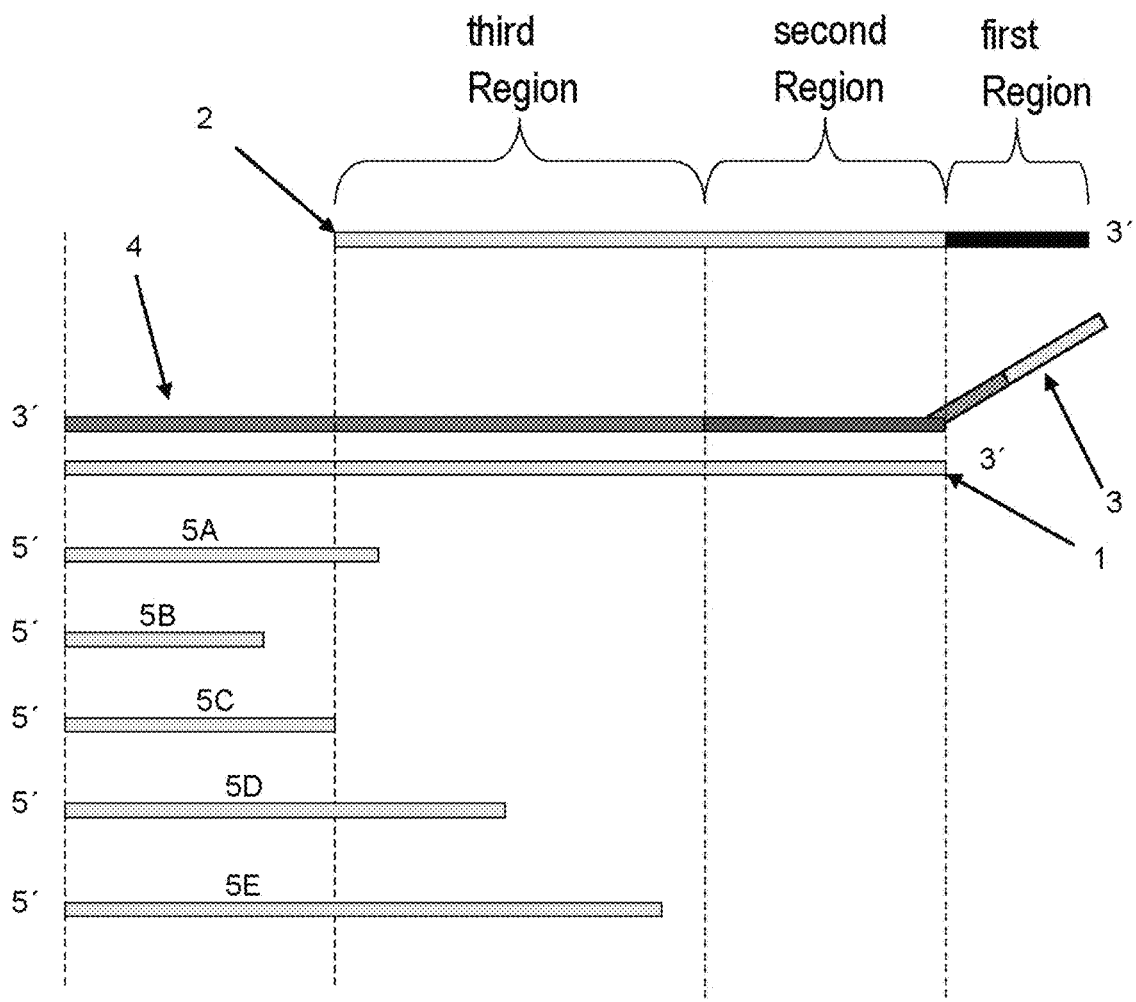
Figure 25:
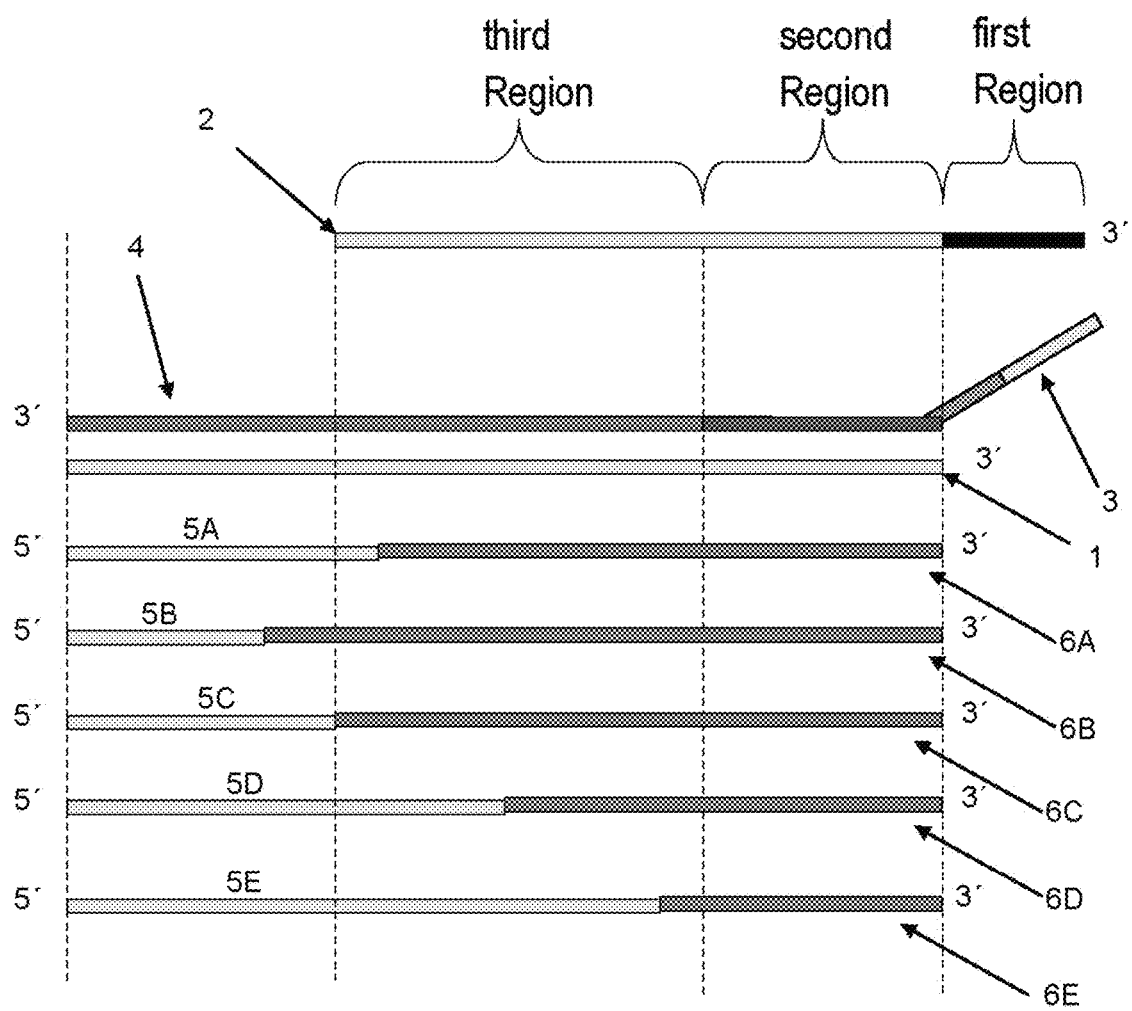
Figure 26:
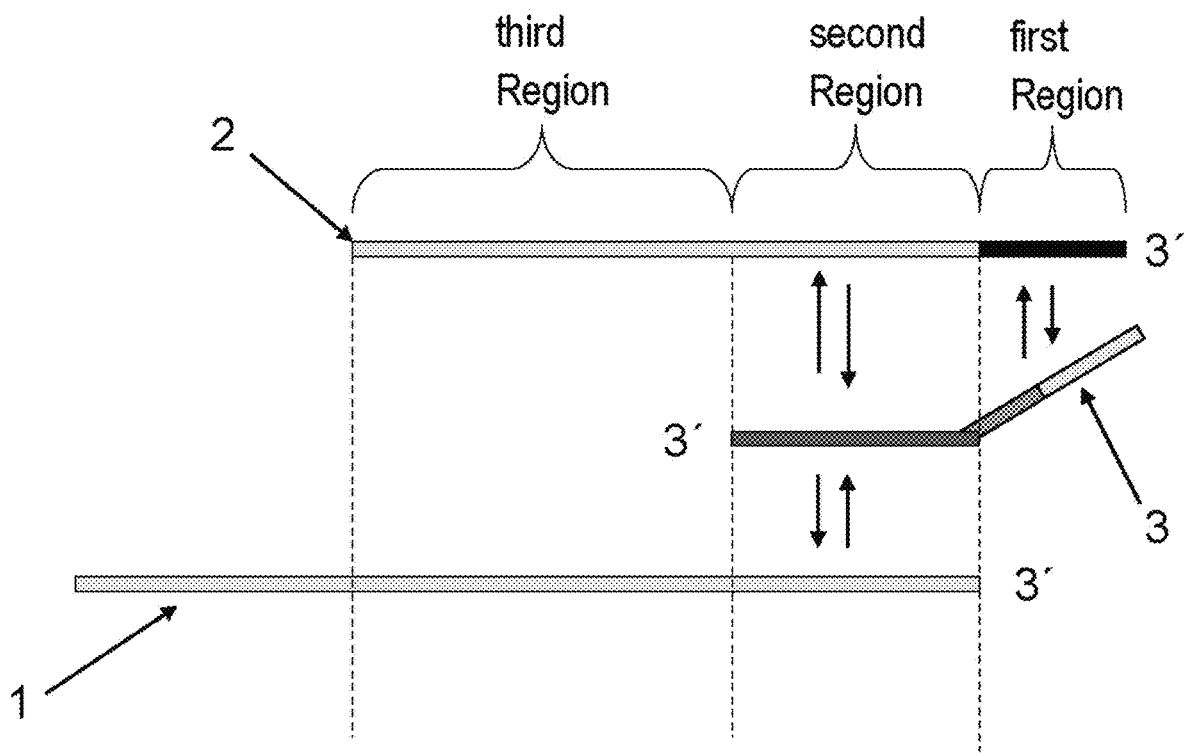
Figure 27:
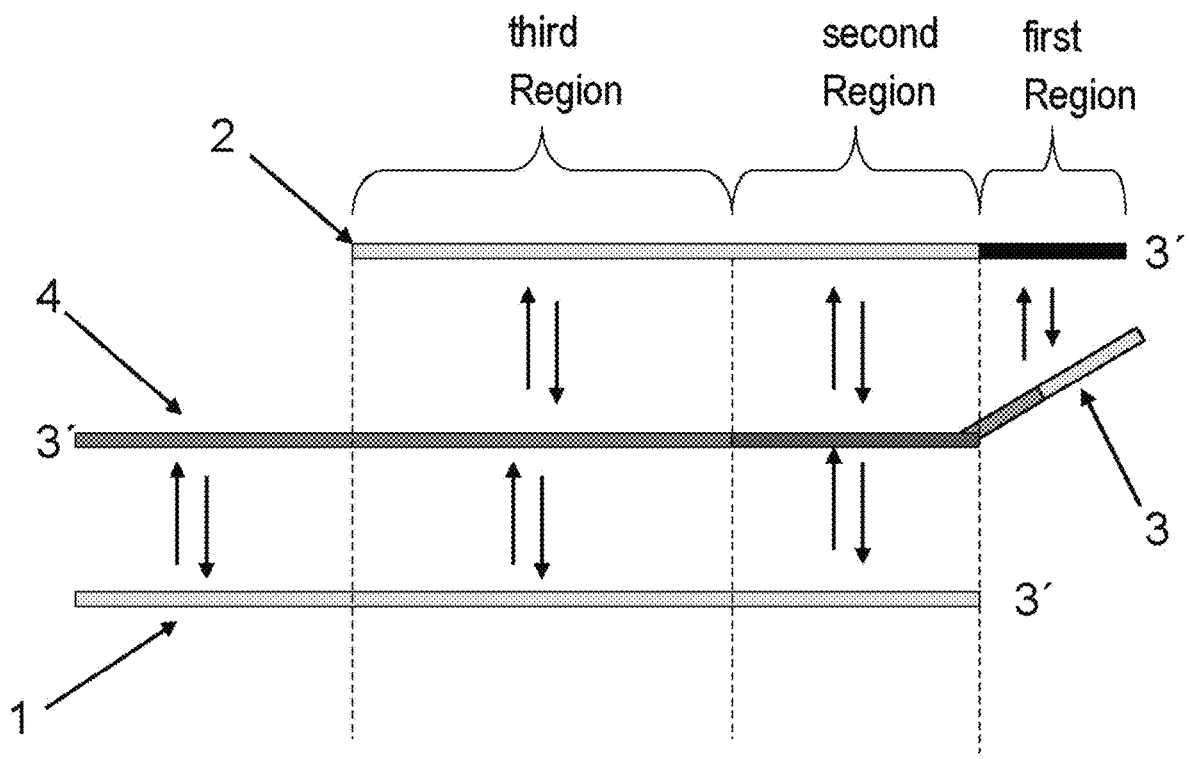
Figure 30:
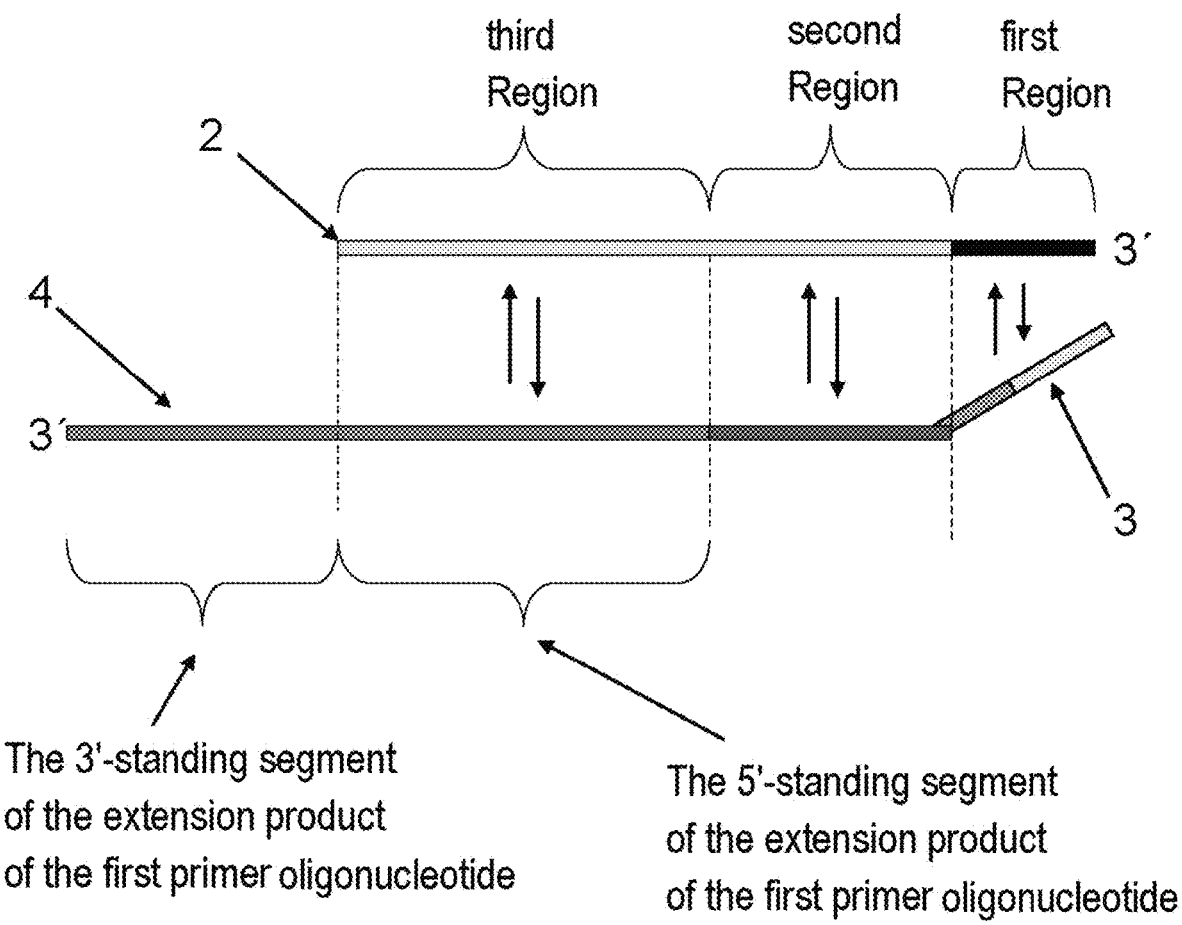
Figure 31:
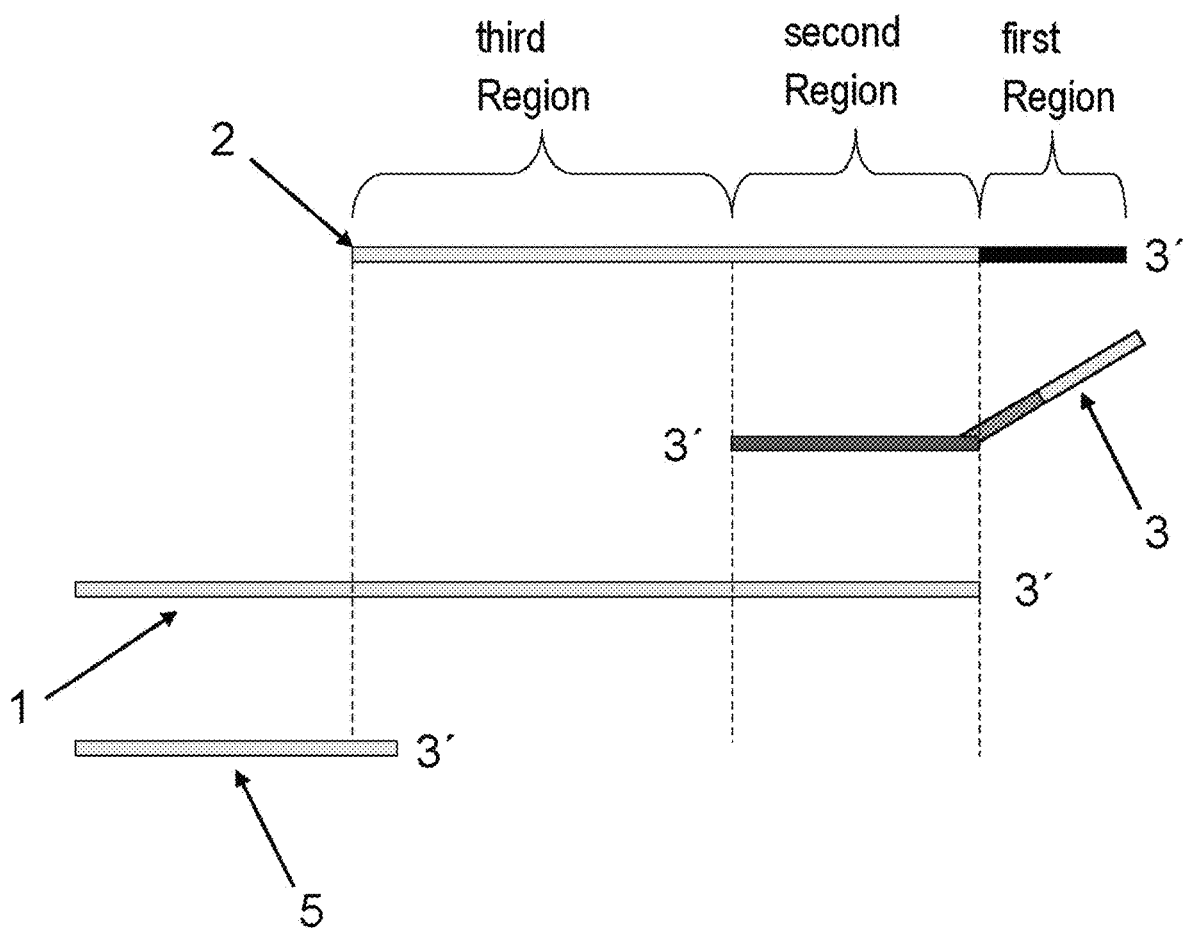
Figure 32:
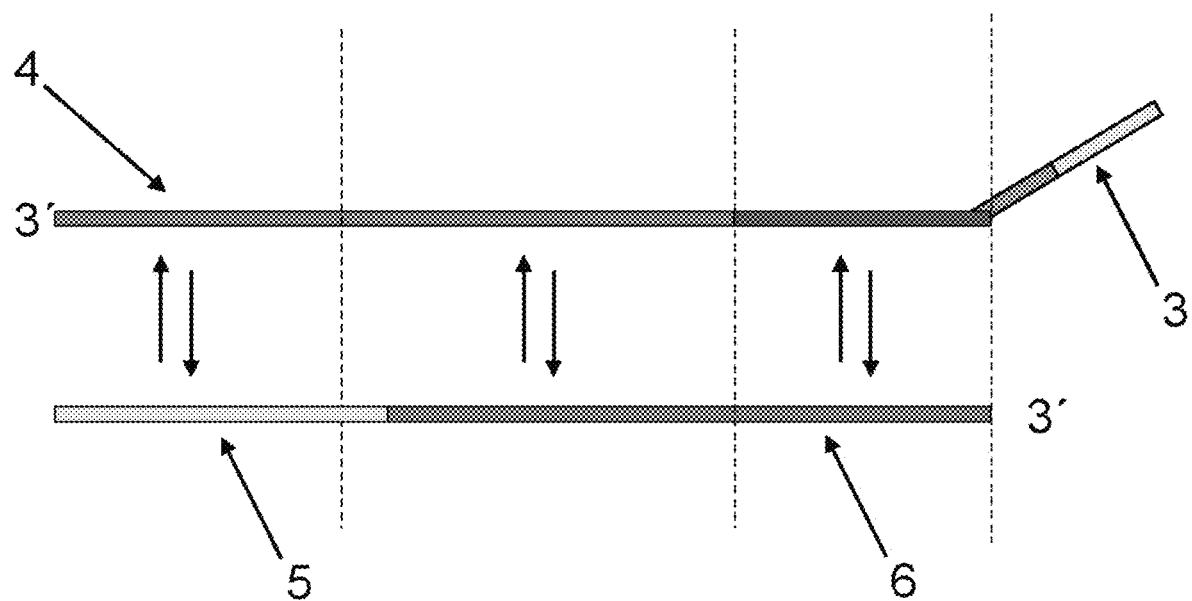

In one embodiment, the second primer oligonucleotide with its copyable portions in their length corresponds to the 3' segment of the first primer extension product that is not bound by the activator oligonucleotide (FIG. 24, Primer 5C). In the complex comprising the second primer oligonucleotide and the first primer extension product the 3' end of such a second primer oligonucleotide borders on the activator oligonucleotide that is bound to the first primer extension product. Extension of such a primer is done by using the first primer extension product as a template. In the extension of such a primer displacement of the activator oligonucleotide from the binding with the first primer extension product takes place by means of polymerase-dependent strand displacement. The corresponding second primer extension product is shown in FIG. 25 (primer extension product 6C).

In a further embodiment, the second primer oligonucleotide with its copyable sequence portions is shorter than the 3' segment of the first primer extension product that is not bound by the activator oligonucleotide (FIG. 24, primer 5B). In the complex comprising the second primer oligonucleotide and the first primer extension product thus between the 3' end of such a primer and the activator oligonucleotide bound to the first primer extension product there is a single-stranded section of the first primer extension product. Extension of such a primer is done by using the first primer extension product as a template. In the extension of such a primer displacement of the activator oligonucleotide from the binding with the first primer extension product takes place by means of polymerase-dependent strand displacement. The corresponding second primer extension product is shown in FIG. 25 (primer extension product 6B).

In a further embodiment, the second primer oligonucleotide with its copyable portions is longer than the 3' segment of the first primer extension product that is not bound by the activator oligonucleotide (FIG. 24, primers 5A, 5D, 5E). In the complex of the second primer oligonucleotide and the first primer extension product the 3' segment of the second primer and the 5' segment of the activator oligonucleotide compete for the binding to the first primer extension product. Binding of the 3' segment of the second primer to the first primer extension product that is required for an initiation of the synthesis is with the simultaneous partial displacement of the 5' segment of the activator oligonucleotide.

After initiation of the synthesis by polymerase there is the displacement of such a primer by using the first primer extension product as a template. In the extension of such a primer the displacement of the activator oligonucleotide from the binding with the first primer extension product is done by means of polymerase-dependent strand displacement. The corresponding second primer extension product is shown in FIG. 25 (primer extension product 6A, 6D, 6E). The sequence length of the 3' segment of the second primer oligonucleotide that displaces the 5' segment of the activator oligonucleotide can comprise the following regions: 1 to 50 nucleotides, better 3 to 30 nucleotides, preferably 5 to 20 nucleotides. Using second primer oligonucleotides of a greater length that exceeds the length of the 3' segment of the first primer extension product is for example advantageous in some embodiments. Such embodiments comprise for example a first primer extension product with its 3' segment that is not bound by the activator oligonucleotide being of a length of 5 to 40 nucleotides, better of 10 to 30 nucleotides.

Especially with shorter 3' segments a longer second primer oligonucleotide offers an improved sequence specificity in the initiation of synthesis.

The binding strength of the second primer oligonucleotide to its primer binding site depends on the length of the primer. Generally, longer second primer oligonucleotides can be employed with higher reaction temperatures.

Preferably, sequences of the first and second primer oligonucleotides and of the activator oligonucleotide are adapted to each other such that side reactions, e.g., primer dimer formation, are minimized. For that, for example the sequence of the first and second primer oligonucleotides are adapted to each other such that both primer oligonucleotides are not able to start an amplification reaction in the absence of an appropriate template and/or a target sequence and/or a start nucleic acid chain. This can be achieved for example in that the second primer oligonucleotide does not comprise a primer binding site for the first primer oligonucleotide and the first primer oligonucleotide does not comprise a primer binding site for the second primer oligonucleotide. Moreover, it is to be avoided that the primer sequences comprise extended self-complementary structures (self-complement).

The synthesis of the second primer extension product is a primer extension reaction and forms an individual step in the amplification. The reaction conditions during this step are accordingly adapted. Reaction temperature and reaction time are selected such that the reaction can successfully take place. The preferred temperature in this step depends on the polymerase used and the binding strength of the respective second primer oligonucleotide to its primer binding site and comprises for example ranges of 15° C. to 75° C., better of 20 to 65° C. preferably of 25° C. to 65° C. The concentration of the second primer oligonucleotide comprises ranges of 0.01 µmol/l to 50 mol/l, better of 0.1 µmol/l to 20 mol/l, preferably of 0.1 µmol/l to 10 mol/l.

In one embodiment, all steps of the amplification proceed under stringent conditions that prevent or decelerate the formation of non-specific products/by-products. Such conditions are for example higher temperatures, for example above 50° C.

If more than one specific nucleic acid chain has to be amplified in one batch, so in one embodiment preferably sequence-specific primer oligonucleotides are used for the amplification of the respective target sequences.

In one embodiment, the synthesis of the first and second primer extension products proceeds at the same temperature. In a further embodiment, the synthesis of the first and second primer extension products proceeds at different temperatures. In a further embodiment, synthesis of the second primer extension product and strand displacement by the activator oligonucleotide proceed at the same temperature. In a further embodiment, synthesis of the second primer extension product and strand displacement by the activator oligonucleotide proceed at different temperatures.

Primer Oligonucleotides Comprising Additional Sequence Segments:

The above-mentioned structures of the first primer and the second primer may be summarized as so-called "base primer structure" or "minimum primer structure".

Such base structures of oligonucleotides having a primer function (e.g., first primer oligonucleotide, second primer oligonucleotide, optionally third primer oligonucleotide, optionally fourth primer oligonucleotide, etc.) comprise sequence segments that are of advantage for carrying out the amplification method, for example the first and second regions of the first primer.

Such a base structure of primers may be extended by further additional sequence segments. Such additional sequence segments comprise structures which themselves certainly are not needed for carrying out the amplification method, but may be useful for other tasks.

Such additional sequence segments optionally may be inserted into a primer and employed for further functions or reactions, respectively. In this way, the primer extension products synthesized by polymerase (e.g., starting from the first and/or second primers) can be connected to such sequence segments. In this way, an integration of such additional sequence segments and primer extension products to a molecular structure is achieved. Such an integration may be of advantage in certain embodiments. A number of applications for primer sequences having additional sequence segments is known to the skilled person.

Several functions are known to the skilled person which are supported by additional sequence segments of the primer.

Insertion of additional structures may be used for example as a means for mediating an intermolecular or intramolecular binding. Several examples of such structures are known to the skilled person. For example, probes may be designed in accordance with such principle of an intramolecular binding, e.g., in connection with scorpion primers. For example, further sequence segments may be used to bind further oligonucleotides. Here, a sequence-specific intermolecular binding may be formed by using stringent conditions. Such interactions may for example be used to bind amplification products to a solid phase via complementary binding to immobilized oligonucleotides.

A further example is insertion of so-called adaptor sequences and/or use of further sequence segments for unique coding or sequence-specific labelling primers and primer extension products starting therefrom (so-called primer barcoding). This is used for example for NGS library preparation (Ståhlberg et al Nucleic Acids Res. 2016 Jun. 20; 44(11): e105). In sequence analysis of primer extension products sequences may later be assigned by such a labelling.

Yet another example is represented by the use of further sequence segments for inserting specific sequences with binding of certain proteins, e.g. restriction endonucleases, etc.

Yet another example is represented by the use of further sequence segments for inserting spacer sequences which shall not bind a specific interaction partner, but mainly are used to increase the distance between adjacent sequences.

Such additional sequences may either be positioned on the copyable portion of the primer or attached to the non-copyable portion of the primer. Several factors are relevant in determining whether or not a sequence segment is copied. For example, positioning of the sequence segment in the respective oligonucleotide in the used nucleotide modifications (e.g. C3, HEG, 2'-Ome, etc.) may decide whether or not a sequence segment is used as a template during a process step.

In one embodiment an additional sequence segment is inserted into the copyable region of the primer, e.g. on the 5' segment of the copyable portion of the second primer, so that for example in reading the primer sequence during a synthesis operation of target sequence also additional sequence segments are read by polymerase. The length of such an additional sequence segment includes ranges of 3 to 50 nucleotides. The composition of said sequence segments in this embodiment allows the synthesis by a polymerase, i.e. said sequence segment functions as a template for polymerase-dependent synthesis. In such a segment for example natural nucleotides are used, e.g. dA, dG, dC, dT.

In a further embodiment additional sequence segments may for example be positioned at the 5' terminus of the primer which should not be copied in the synthesis of specific amplification fragments comprising a target sequence. This may for example be achieved by positioning one or more modifications or chemical groups, which hinder polymerase from synthesizing a complementary strand (e.g. HEG, C3, a segment comprising 4-10 nucleotides having 2'-Ome modifications, etc.). Such a modification may for example be positioned at the 5' terminus of the copyable portion of the second primer and hinder continuation of the synthesis. For example, an HEG group may be inserted at the 5' end of the copyable segment of the second primer, and subsequently an additional sequence segment.

Moreover, an additional sequence segment may be positioned at the 5' terminus of the second region of the first primer. By such a localization of additional sequence segments synthesis of a complementary strand during a regular synthesis of specific amplification products comprising a target sequence is prevented.

The length of such an additional sequence segment comprises regions of 3 to 50 nucleotides. The base composition for example can comprise natural nucleobases (A, G, C, T, U, inosines) or modifications at different positions of nucleotides (e.g. at the bases, such as 2-amino-adenine, iso-guanine, iso-cytosine, 5-propargyl uridine, 5-propargyl cytosine, or at the sugar phosphate backbone, such as for example LNA, 2'-Ome, 2'-halogene, etc.). In a certain embodiment a first primer and additional sequence segments are combined in one oligonucleotide. In a further certain embodiment a second primer and additional sequence segments are combined in one oligonucleotide.

Such additional sequence segments are designed in one oligonucleotide such that they preferably do not prevent the amplification method of target sequences. For example, this is achieved in that inhibiting interactions with the structures of the primers or controllers that are essential for the method are avoided or reduced, respectively. In a certain embodiment additional structures can form complementary double strand segments with other primer regions under chosen reaction conditions. However, preferably such double-stranded segments do not prevent a specific amplification of a target sequence. In a further certain embodiment such additional sequence segments do not interact with or bind to the first or second primer regions of the first primer. In a further embodiment such additional sequence segments do not interact with the controller oligonucleotide. In a further embodiment such additional sequence segments do not interact with other primers in the reaction. In a further embodiment such additional sequence segments do not interact with P1.1-Ext or P2.1-Ext or other amplification fragments comprising a target sequence. In a further embodiment such additional sequence segments do not form double-stranded regions with the first or second regions of the first primer that are stable under reaction conditions and completely prevent the function of the first or second regions.

In a certain embodiment such additional sequence segments do not interact with or bind to the second primer. In a further embodiment such additional sequence segments especially do not interact with the 3' segment of the second primer.

In one embodiment the first primer at its 5' terminus of the second region comprises an additional sequence segment of the first primer (additive sequence variant P1). Said segment optionally comprises a sequence of 10-50 nucleotides that does not interfere with the amplification method of target sequences (e.g. does not form secondary structures with primers). Moreover, said segment optionally comprises a sequence of about 5 to 15 nucleotides of the copyable first region of the first primer. The additive sequence variant P1 comprises natural nucleotides as monomers (A, C, G, T) and may potentially function as a template for a polymerase.

In one embodiment the second primer at its 5' terminus comprises an additional sequence segment of the second primer (additive sequence variant P2). Said segment optionally comprises a sequence of 10-50 nucleotides that does not interfere with the amplification method of target sequences (e.g. does not form secondary structures with primers). Moreover, said segment optionally comprises a sequence of about 5 to 15 nucleotides of the copyable region of the second primer. The additive sequence variant P2 comprises natural nucleotides as monomers (A, C, G, T) and may potentially function as a template for a polymerase.

It has been observed that such oligonucleotides comprising a first primer and additive sequence variant P1 or oligonucleotides comprising a second primer and additive sequence variant P2 to a smaller extend are susceptible to side reactions than oligonucleotides only comprising a first primer or oligonucleotides only comprising a second primer. In a certain embodiment, for example generation and/or amplification of unspecific primer dimer structures may be delayed. Thus, in such a side reaction optionally formation of by-products not comprising a target sequence may be reduced or delayed. In this way, for example premature consumption of primers may be reduced or delayed. For example, it is of advantage to employ such oligonucleotides if side reactions of primers-dimers comprising the first primer (PD P1) or primers-dimers comprising the second primer (PD P2) result in the premature consumption of primers in the reaction. The use of primers with such additional structures (first primer with additive sequence variant P1 and/or second primer with additive sequence variant P2) in certain embodiments is of advantage if in an amplification reaction non-specific reactions are observed. Such side reactions may be favored by several factors, these are among others:

prolonged reaction times (e.g., reaction times range between 1 hr and 100 hrs)
  higher concentrations of primers are used (e.g., concentrations range between 1 μmol/1 and 1 mmol/l)
  higher concentrations of polymerase are used (e.g., concentrations are in ranges above 10 units/10 μl)
  multiplex reactions (e.g., amplification of more than 10 different target sequences in one reaction batch)
  high concentrations of complex nucleic acid chains in the reaction batch (e.g., concentrations above 1 g hgDNA in 50 μl)

wherein single factors may favor side reactions alone or in combination with other factors.

In general, it is possible to act against side reactions (e.g., non-specific primer-dimer formation) by optimizing reaction components and/or reaction conditions, for example by reducing concentrations of individual components, shorter reaction times, sequence designing of primer sequences, choosing more stringent reaction conditions. The additional sequence segments (oligonucleotides comprising a first primer and additive sequence variant P1 or oligonucleotides comprising a second primer and additional sequence variant P2) given in an advantageous embodiment represent a further possibility to delay certain side reactions.

In examples there are shown primer oligonucleotides with additional sequence segments. In said examples additional sequence segments are used that do not participate in the specific amplification of a target sequence and contribute to the delay of side reactions. Thus, oligonucleotides comprising a first primer and additive sequence variant P1 and oligonucleotides comprising a second primer and additive sequence variant P2 are used.

A skilled person will appreciate that an oligonucleotide in addition to a primer structure that is of advantage for the specific amplification of a target sequence (said structure may also be referred to as "base primer structure" or "minimum primer structure") can also comprise further additional sequence segments (e.g., additive sequence variant P1 or additive sequence variant P2). Such additional sequence segments may bring about a lot of different further advantages or useful properties or functions, respectively.

Exponential Vs. Linear Amplification

If both complementary strands (the first primer extension product and the second primer extension product, wherein both primer extension products can be templates for the syntheses of the complementary strands) are synthesized substantially in parallel to each other in the same batch an exponential propagation of both primer extension products can occur during such a reaction.

The primer extension products re-synthesized during a synthesis process close the respective complementary sequence parts to primers used, so that new primer binding sites are generated. In this way, re-synthesized strands themselves can function as templates in the subsequent synthesis processes.

If substantially only one primer extension product is synthesized as a result of cyclically repeated synthesis processes, so a linear amplification of said primer extension product occurs.

In an advantageous embodiment of the method both primers are employed substantially in equally high concentrations or in concentration ranges that are approximately equally high.

In a further advantageous embodiment of the method at least one of both primers is employed in a higher concentration than its partner primer. Here, the differences in concentrations may be in ranges that are between 1:2 to 1:50, advantageously between 1:2 to 1:10.

This can result in an asymmetric amplification reaction in which the concentration of a primer extension product is accordingly higher than that of the other strand.

The examples cited below are to be stated only to demonstrate the method and are not to be interpreted as being limiting.

The structures, sequences, and reaction conditions given in the examples are only to represent and illustrate the mode of function of the method and do not function as a limitation.

EXAMPLES

Material and Methods:
Reagents were commercially purchased from the following suppliers:
unmodified and modified oligonucleotides (Eurofins MWG, Eurogentec, Biomers, Trilink Technologies, IBA Solutions for Life Sciences)
polymerases NEB (New England Biolabs)
dNTPs: Jena Bioscience
intercalating Eva green dye: Jena Bioscience
buffer substances and other chemicals: Sigma-Aldrich
plastic goods: Sarstedt Solution 1 (Amplification Reaction Solution 1):
potassium glutamate, 50 mmol/l, pH 8.0
magnesium acetate, 10 mmol/l
dNTP (dATP, dCTTP, dGTP), 200 µmol/leach
polymerase (Bst 2.0 WarmStart, 120,000 U/ml NEB), 12 units/10 µl
Triton X-100, 0.1% (v/v)
EDTA, 0.1 mmol/l
TPAC (tetrapropylammonium chloride), 50 mmol/l, pH 8.0
Eva green dye (the dye was employed in accordance with the manufacturer's instructions in dilution of 1:50).

Solution 2 (Amplification Reaction Solution 2)
1× isothermal buffer (New England Biolabs); in a single concentration the buffer contains:
20 mM Tris-HCl
10 mM $(NH_4)_2SO_4$
50 mM KCl
2 mM $MgSO_4$
0.1% Tween® 20
pH 8.8@25° C.
dNTP (dATP, dCTP, dUTP, dGTP), 200 µmol/l each
Eva green dye (the dye was employed in accordance with the manufacturer's instructions in dilution of 1:50)

Solution 3 (Amplification Reaction Solution 3)
1× isothermal buffer (New England Biolabs); in a single concentration the buffer contains:
20 mM Tris-HCl
10 mM $(NH_4)_2SO_4$
50 mM KCl
2 mM $MgSO_4$
0.1% Tween® 20
pH 8.8@25° C.
dNTP (dATP, dCTP, dUTP, dGTP), 200 µmol/l each All concentrations are indications of the final concentrations in the reaction. Deviations from the standard reaction are indicated accordingly.

The melting temperature (Tm) of the participating components was determined upon concentration of 1 mol/of the respective components in solution 1. Deviating parameters are indicated respectively.

General Information on Reactions

Primer extension reactions and amplification were performed at a reaction temperature of 65° C. in a standard manner. Deviations are indicated.

The reaction was started by heating the reaction solutions to the reaction temperature since Bst 2.0 polymerase Warmstart at lower temperatures is mainly inhibited in its function by a temperature-sensitive oligonucleotide (according to the manufacturer's specifications). The polymerase becomes increasingly more active from a temperature of ca. 45° C., at a temperature of 65° C. no differences between polymerase Bst 2.0 and Bst 2.0 Warmstart could be observed. In order to prevent the extensive formation of by-products (e.g., primer dimer) during the preparation phase of a reaction polymerase Bst 2.0 Warmstart was used. Deviations are specifically indicated.

The reaction was stopped by heating the reaction solution to above 80° C., e.g., 10 min at 95° C. At this temperature polymerase Bst 2.0 is irreversibly denaturized and the result of synthesis reaction cannot be changed later.

The reactions were carried out in a thermostat having a fluorimeter. For that, a commercial Real-Time PCR apparatus was used, StepOne Plus (Applied Biosystems, Thermofischer). The reaction volume by default was 10 µl. Deviations are indicated.

Both end-point detection and kinetic observations have been made. In end-point detections the signal was recorded for example by a nucleic acid-bound dye, e.g., by TMR (tetramethyl rhodamine, also referred to as TAMRA) or by FAM (fluorescein). The wavelengths for exciting and measuring the fluorescence signals of FAM and TMR are stored as the factory settings in the StepOne Plus Real-Time PCR apparatus. Also, an intercalating dye (Eva green) was used in end-point measurements, e.g., in measuring the melting curve). Eva green is an intercalating dye and an analogue of the frequently employed SYBR green dye, however, with a slightly less inhibition of polymerases. The wavelengths for exciting and measuring the fluorescence signals of SYBR green and Eva green are identical and stored as the factor settings in the StepOne Plus Real-Time PCR apparatus. Fluorescence can continuously be detected by means of built-in detectors, i.e. "online" or "real-time". Since the polymerase during its synthesis synthesizes a double strand this technique could be used for kinetic measurements (real-time monitoring) of the reaction. Due to a certain cross-talk between color channels in the StepOne Plus apparatus a partially increased basal signal intensity was observed in measurements in which e.g., TMR-labeled primers were used in concentrations of more than 1 mol/l (e.g., 10 µmol/l). It was observed that the TMR signal in the SYBR green channel leads to increased basic values. These increased basic values were taken into account in calculations.

The kinetic observations of courses of reactions were routinely recorded by means of fluorescence signals of fluorescein (FAM-TAMRA Fret pair) or intercalating dyes (Eva green). Time-dependence of the signal course was detected (real-time signal detection in the StepOne plus PCR apparatus). An increase of the signal during a reaction compared to a control reaction was interpreted depending on the structure of the batch. For example, an increase in the signal using EVA green dye was interpreted as an indication of an increase in the amount of double-stranded nucleic acid chains during the reaction, and thus, judged to be the result of a synthesis by DNA polymerase.

In some reactions a melting curve determination was performed following the reaction. Such measurements allow to draw conclusions about the presence of double strands that for example can absorb intercalating dyes and this way significantly enhance signal intensity of dyes. With the rising temperature the proportion of double strands decreases and also the signal intensity decreases. The signal depends on the length of the nucleic acid chains and on the sequence composition. Said technique is well known to the skilled person.

When using melting curve analysis in context with reactions that contained significant proportions of modified nucleic acid chains (e.g., activator oligonucleotides or primers) it was found that the signal of the Eva green dye can behave different for example between the B form of the DNA and the A form of modified nucleic acid chains. For example, in the B form of the double-stranded nucleic acid chains (usually taken on for classical DNA sections) a higher signal intensity was observed than with double-stranded nucleic acid chains having the same sequence of nucleobases that can take on an A-form-like conformation (e.g., by several 2'-O-Me modifications of nucleotides). This observation was taken into account when intercalating dyes were employed.

As needed, the reaction was analyzed by means of capillary electrophoresis and the length of fragments formed was compared to a standard. In preparation for the capillary electrophoresis the reaction mixture was diluted in a buffer (Tris-HCl, 20 mmol/l, pH 8.0, and EDTA, 20 mmol/l, pH 8.0) such that the concentration of labeled nucleic acids was ca. 20 nmol/l. Capillary electrophoresis was performed at GATC-Biotech (Konstanz, Germany) as contractual service. In accordance with the specifications of the supplier the capillary electrophoresis was performed on an ABI 3730 Capillary Sequencer under standard conditions for Sanger sequencing using a POP7 gel matrix at ca. 50° C. and a constant voltage (ca. 10 kV). The conditions used resulted in the denaturation of double strands, so that in the capillary electrophoresis the single-stranded form of nucleic acid chains was separated. Electrophoresis is a standard technique in the genetic analysis. The automated capillary electrophoresis is employed routinely in Sanger sequencing to this day. The fluorescence signal is continuously recorded during the capillary electrophoresis (usually using virtual filters), so that an electrophoretogram is generated in which the signal intensity correlates to the duration of the electrophoresis. With shorter fragments, e.g., unused primers, there is observed an early signal peak, with extended fragments there is a temporal shift of the signals proportional to the length of the extended regions. Thanks to controls with known lengths the length of extended fragments can be measured. Said technique is known to a skilled person and is also employed by default in fragment length polymorphism.

Example 1

Use of Human Genomic DNA as a Source of a Target Sequence

In this example the use of humane genomic DNA (hgDNA) as a source of a target sequence and use of an intercalating dye as a detection system are shown. As the target sequence a sequence segment of the factor-V Leiden gene (*Homo sapiens* coagulation factor V (F5), mRNA, here referred to as FVL-Gene) was chosen.

Target Sequence:

(SEQ ID NO: 1)
5'<u>GTAA GAGCAGA</u>TCC CTGGACAGGC AA <u>GGAATACAGGTA</u>-

3'

The binding sequence for the first primer oligonucleotide is underlined. The second primer oligonucleotide with its 3' segment binds to the reverse complement of the double-underlined sequence.

The first primer, the second primer as well as the activator oligonucleotide were designed and synthesized for the FVL mutation variant of the gene.

The First Primer Oligonucleotide (SEQ ID NO:2):

```
P1F5-200-AE2053
5'AACTCAGACAAGATGTGA TTTTTTTACCTGTAT 7878

65867887 1 TACCTGTATTCC3'
```

The segment used as the primer in the reaction is underlined.
A=2'-deoxy-adenosine
C=2'-deoxy-cytosine
G=2'-deoxy-guanosine
T=2'-deoxy-thymidine (thymidine)
Said oligonucleotide comprises the following modifications:
1=C3 linker
5=2'-O-Me A (2'-O-methyl-adenosine)
6=2'-O-Me G (2'-O-methyl-guanosine)
7=2'-O-Me C (2'-O-methyl-cytosine)
8=2'-O-Me U (2'-O-methyl-uridine)

Said primer oligonucleotide comprises the first region (positions 1-12 from the 3' end), the second region (C3 linker as well as positions 13-24 from the 3' end) as well as a segment having an additive sequence variant P1 (positions 25-57 from the 3' end). The first region and the second region are required to perform a specific amplification and may be combined as "base primer structure" or "minimum primer structure". The additive sequence variant P1 represents one example of additional sequence segments that can be integrated at the first primer oligonucleotide. Positions 1-12 are used as a template in the synthesis of the second primer extension product. C3 modification and the second region prevent a continuation of the synthesis at positions 25-57 during a synthesis of the second primer extension product.

Primer 2:

```
P2G3-5270-7063
                                        (SEQ ID NO: 3)
5'CTACAGAACTCAGACAAGATGTGAACTACAATGTT

6 GCTCATACTACAATGTCACTTACTGTAAGAGCAGA3'
```

The segment used as the primer in the reaction is underlined.
Said oligonucleotide comprises the following modifications:
6=HEG linker
A=2'-deoxy-adenosine
C=2'-deoxy-cytosine
G=2'-deoxy-guanosine
T=2'-deoxy-thymidine (thymidine)

Said primer oligonucleotide comprises a copyable region and a non-copyable region. The copyable region comprises (positions 1-13 from the 3' end that can complementary bind to a sequence of the FVL gene within hgDNA and positions 14-35 that certainly do not complementary bind to the sequence of the FVL gene, but can bind to the first primer extension product during the amplification). The copyable region may be summarized as a "base primer structure" or "minimum primer structure".

The uncopyable region (positions 36-70 from the 3' end that do not complementary bind to the sequence of the FVL gene) is separated from the copyable region by an HEG modification, what prevents continuation of the synthesis at positions 36-70 during a synthesis of the first primer extension product. The uncopyable region represents an example of an additive sequence variant P2 that can be integrated at the second primer oligonucleotide.

The following activator oligonucleotide (SEQ ID NO:4) was used:

```
AD-F5-1001-503
5'- TAATCTGTAA GAGCAGATCC CTGGACAGGC AA

GGAATACAGGTA GAAGCATC AGAGAA X 3'
```

Said oligonucleotide comprises the following modification:

```
5' [UAAUCUGUAA GAGCAGAUCC CUGGACAGGC AA

GGAAUAC]AGGTAGAAGCATC AGAG X 3'
```

A=2'-deoxy-adenosine
C=2'-deoxy-cytosine
G=2'-deoxy-guanosine
T=2'-deoxy-thymidine (thymidine)

The 5' segment of the oligonucleotide [UAAUCUGUAA GAGCAGAUCC CUGGACAGGC AA GGAAUAC] comprises 2'-O-Me-nucleotide modifications:
Modifications:
A=(2'-O-methyl-adenosine)
G=(2'-O-methyl-guanosine)
C=(2'-O-methyl-cytosine)
U=(2'-O-methyl-uridine)
X=3'-Phosphate group for blockage of a possible extension by polymerase.

The nucleotides and nucleotide modifications are mutually linked to phosphodiester bonds. The 3' end of the activator oligonucleotide is blocked with a phosphate group to prevent a possible extension by the polymerase.

The first primer in its first region comprises a sequence that can specifically bind to the sequence of the factor-V Leiden gene within the genomic DNA, so that a synthesis by a polymerase can be started. The second region of the first primer comprises a sequence that does not specifically hybridize to the sequence of the FVL gene. Moreover, the first primer comprises a further sequence segment that links to the 5' end of the second region (additive sequence variant P1). Said segment does not take part in the specific amplification of the factor-5 Leiden segment. The function of said segment is mainly seen in the delay of side reactions.

The second primer comprises a segment in its 3' segment that can specifically bind to the genomic DNA, so that a synthesis by a polymerase can be started. The 5' segment of the second primer comprises a sequence that specifically does not hybridize to the sequence of the FVL gene. During the backward synthesis said sequence segment may be copied. The second primer comprises a further sequence segment that can neither specifically hybridize with the activator oligonucleotide nor with the first primer, nor with the second primer. Said segment was localized at the 5' end of the second primer and is separated from the 5' end of the primer by an HEG linker (additive sequence variant P2). Said segment does not take part in the specific amplification. The function of said segment is mainly seen in the delay of side reactions.

The activator oligonucleotide was constructed such that a perfect match situation to the sequence of the factor-V Leiden mutation of the FVL gene results. The activator oligonucleotide comprises a first, second and third region.

As the genomic DNA the WHO standard for FVL mutation was used. Before using it in the reaction DNA was denatured by heating (5 min. at 95° C.) and thus, transferred from the double-stranded state to the single-stranded state. With the help of said single-stranded hgDNA first a start nucleic acid chain was prepared by a primer extension. Subsequently, an exponential amplification was performed starting from said start nucleic acid chain. Specificity of the amplification is demonstrated by means of melting curve analysis and Sanger sequencing with a sequencing primer.

All reactions were carried out in amplification solution 1.

The dNTPs used comprised: dATP, dGTP, dCTP, dUTP (instead of dTTP).

As the polymerase Bst 2.0 warm-start polymerase by NEB was used.

The start nucleic acid chain was prepared as follows: About 50000 haploid genomic equivalents (HGE), 150 ng hgDNA, were contacted with the second primer (0.5 µmol/l) and Bst-2.0 warm start polymerase (about 1 unit) as well as dNTPs (ca. 250 µmol/l) under hybridization conditions (amplification solution 1, temperature of about 60° C.) in 50 reaction volume and incubated for ca. 10 min. During this phase the second primer was extended with the genomic DNA being used as a template. This results in a primer extension product, which can be used as a start nucleic acid. Upon completion of this reaction the reaction mixture was heated to 95° C. for ca. 10 min to separate said start nucleic acid chain from the template. Said reaction mixture was frozen and used as needed as a source of the start nucleic acid chain.

The specific amplification of the target sequence of the FVL gene takes place using 5 of the reaction mixture with the start nucleic acid chain (corresponds to ca. 5000 HGE).

The other reaction components (first primer, second primer, activator oligonucleotide, Eva-Green dye, polymerase Bst.2.0 warm start, dNTPs) were added, so that a reaction end volume of ca. 10 resulted. The end concentrations of the components were: first primer: 5 µmol/l, second primer: 2 µmol/l, activator oligonucleotide: 1 µmol/l, Eva-Green dye (1:50), polymerase Bst.2.0 warm start (ca. 8 units), dNTPs: ca. 250 µmol/l.

No hgDNA was added to the control batch.

The reaction was carried out in a Step-One Plus apparatus (Thermofisher Scientific).

The reaction temperature was initially changed by cyclic changes (30 cycles) between 65° C. (5 min, including the detection step) and 55° C. (1 min) and subsequently, held constant for 1 hr at 65° C. (detection step every 2 min). The course of the reaction was monitored by signal detection of the EvaGreen dye. On completion of the reaction the reaction mixture was first brought to 95° C. for 10 min and subsequently, a melting curve of the products formed was measured.

A schematic flow of the amplification is illustrated in FIG. 7 to FIG. 10.

Figure 7:
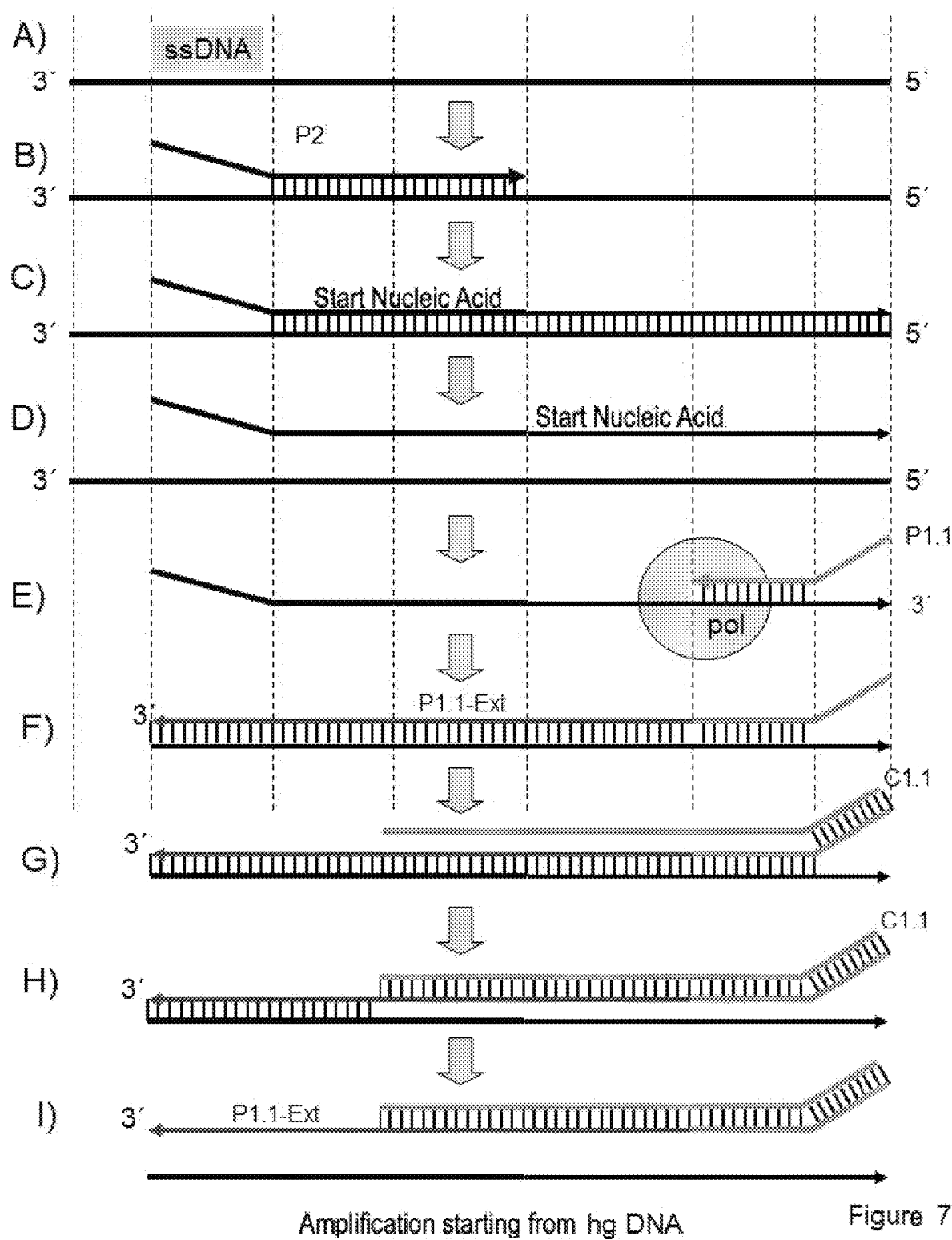
Figure 8:
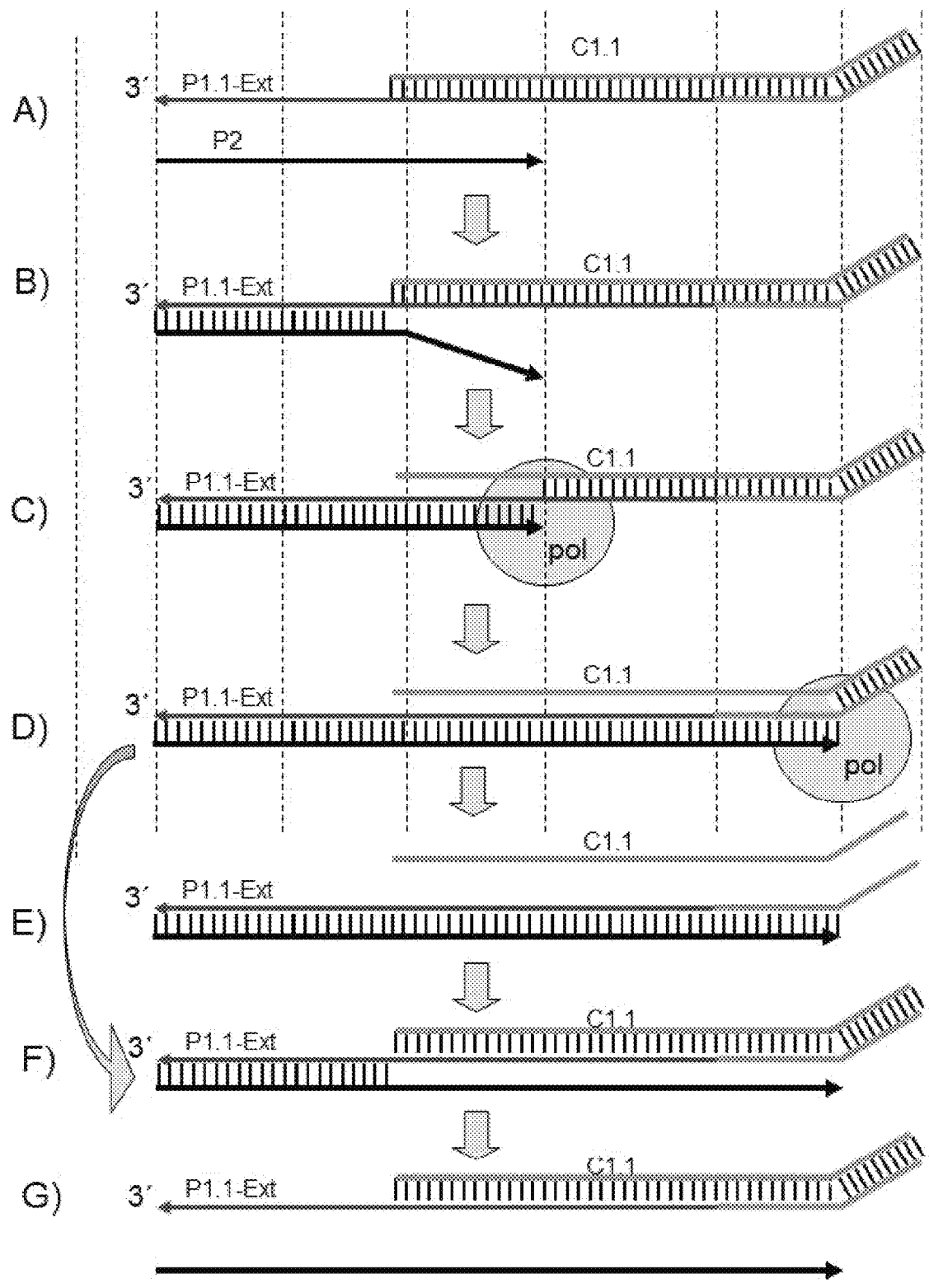
Figure 9:
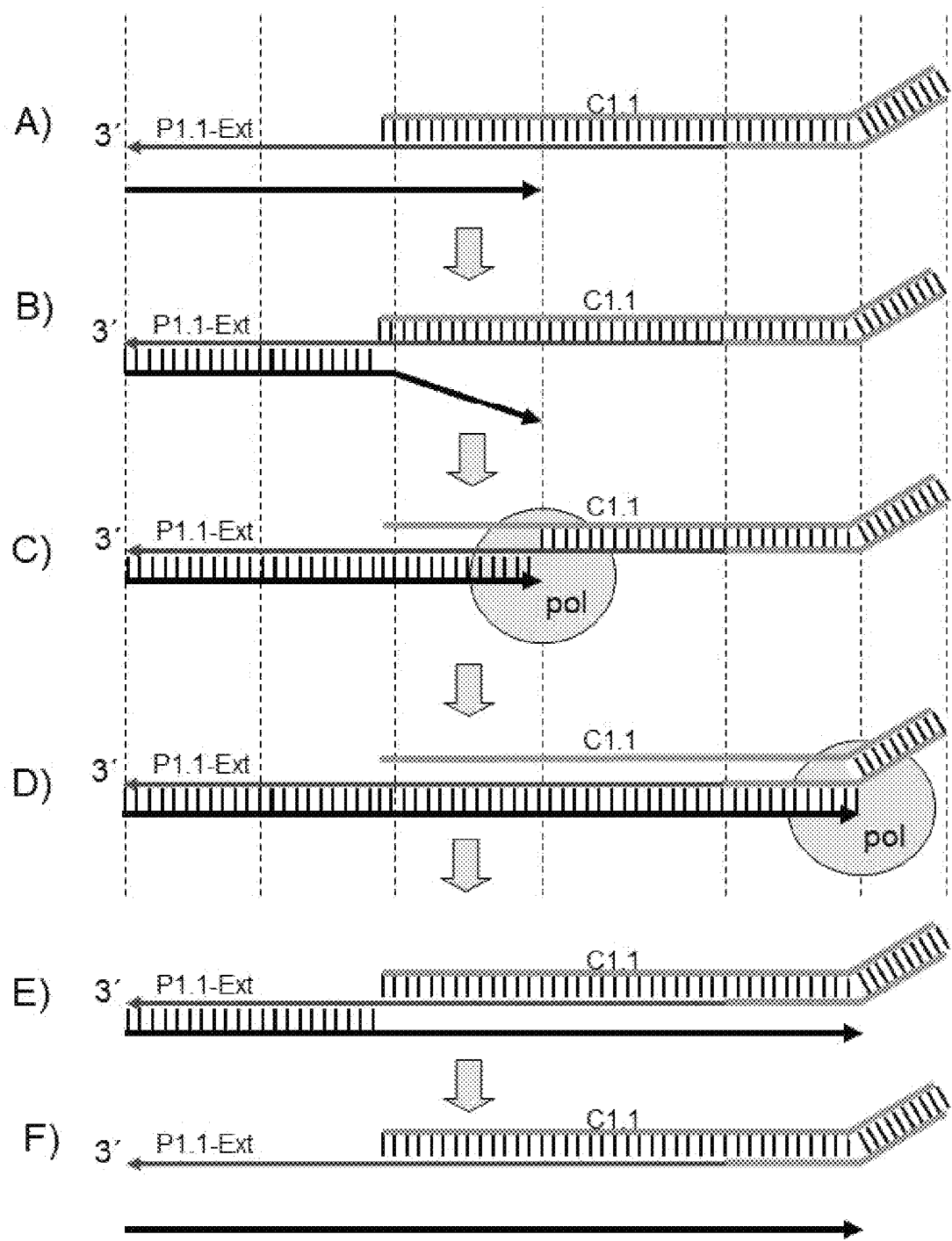
Figure 10:
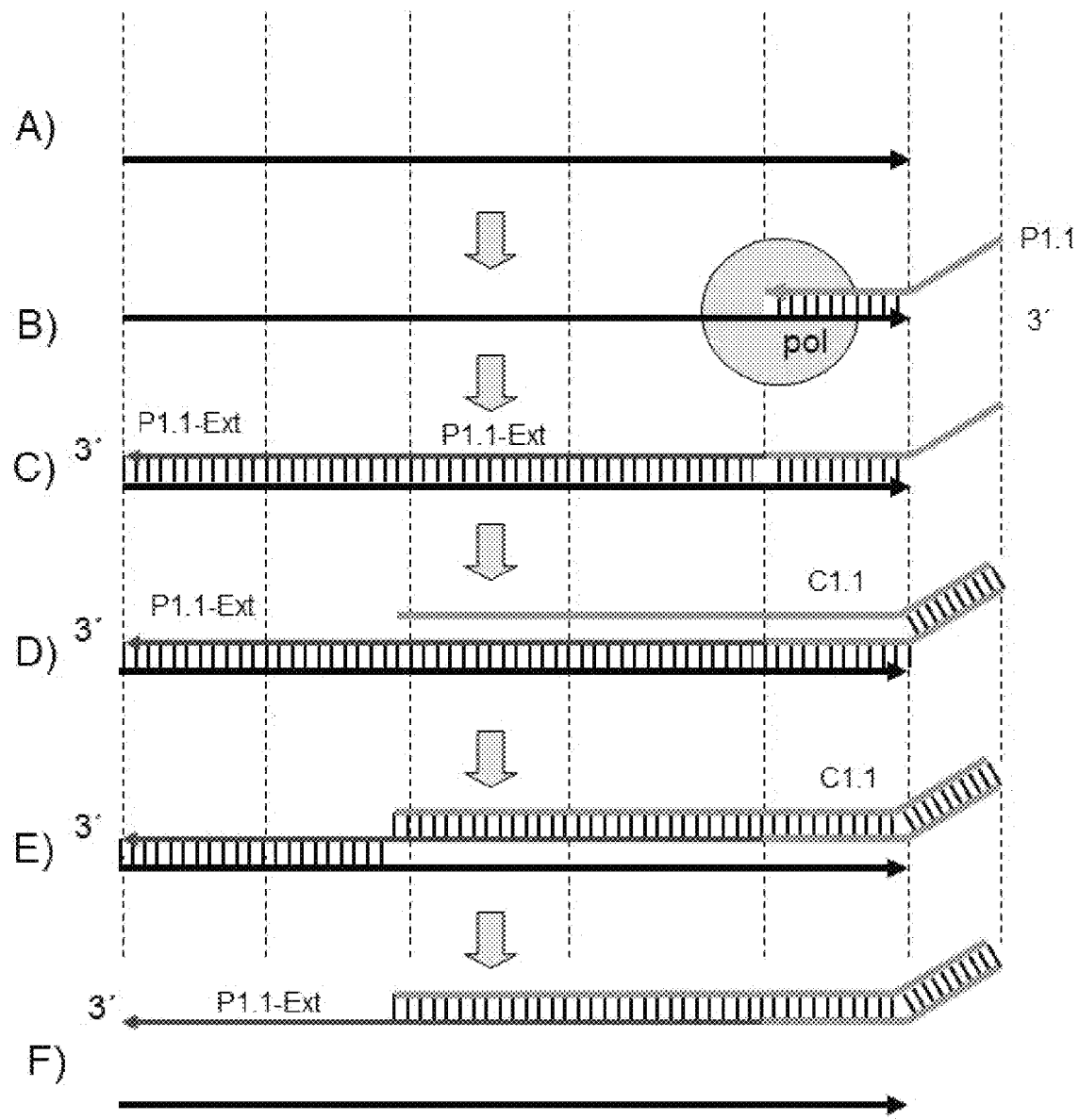

First there was prepared a start nucleic acid chain (FIG. 7, steps A to D). Subsequently, an exponential amplification was carried out to extend the first primer and the second primer and the activator oligonucleotide (FIG. 7E to FIG. 10).

Figure 11:
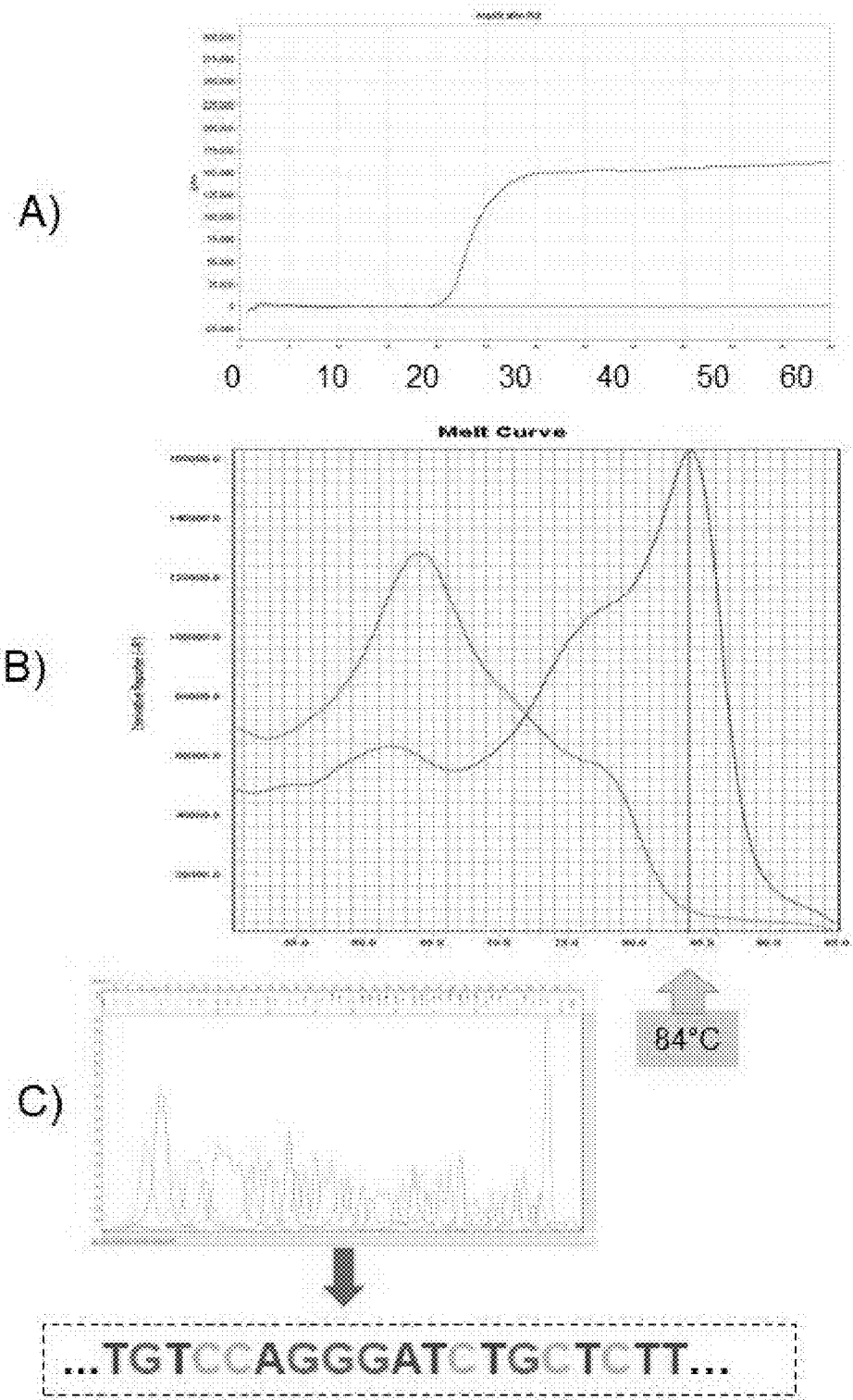
FIG. 11 shows results from example 1.

As a result of the amplification amplification fragments are accumulated. The result of the detection of the amplification can be seen in FIG. 11. As can be seen, after ca. 2 hrs of the reaction there is a noticeable increase in the fluorescence (FIG. 11A). Subsequent melting curve analysis shows a specific melting curve with Tm of 84° C. (FIG. 11B).

Sequence Control (FIG. 11C):

Sequence control was done by means of a sequencing primer:

```
SEQP1F5-35-X03
                                    (SEQ ID NO: 5)
5'- AAG CTCGACAAAAGAAC TCAG AG TGTG CTCGAC AC

TACCTGTATTCC TTGCC 3'
```

For sequence control the reaction mixture (after having measured the melting curve) was diluted with water (from ca. 1:10 to ca. 1:100) and each of the aliquots obtained was mixed with a sequencing primer (added in a concentration of 2 mol/l). Said mixture was shipped by a commercial sequencing supplier (GATC-Biotec) and sequenced by means of Sanger sequencing as a commissioned sequencing. The electropherograms obtained were examined for concordance with the FVL sequence gene. As a result of the reaction the sequence of the FVL gene was identified.

Example 2

Real-Time Monitoring of the Amplification Reaction with an Oligonucleotide Probe In this example oligonucleotide probes are employed to detect synthesized amplification products during an amplification reaction.

The following template was used as a start nucleic acid chain: Template (SEQ ID NO 1) having a sequence composition resulting in a first primer extension product with a perfect match concordance with the activator oligonucleotide:

```
M2SF5-M001-200
                                    (SEQ ID NO: 6)
5' GCT CATA CTACAATGTCA CT TA CTGTAA GAGCAGATCC

CTGGACAGGC AA GGAATACAGGTA AAAAA 3'
```

The binding sequence for the first primer oligonucleotide is underlined. The second primer oligonucleotide binds to the reverse complement of the double-underlined sequence.

The following primers were used:

The first primer oligonucleotide (SEQ ID NO:2):

```
P1F5-200-AE2053 (as in example 1)
                                    (SEQ ID NO: 7)
5' AACTCAGACAAGATGTGA TTTTTTTACCTGTAT 7878 65867887 1 TACCTGTATTCC 3'
```

The segment used as the primer in the reaction is underlined.

A=2'-deoxy-adenosine
C=2'-deoxy-cytosine
G=2'-deoxy-guanosine
T=2'-deoxy-thymidine (thymidine)

Said oligonucleotide comprises the following modifications:

1=C3 linker
5=2'-O-Me A (2'-O-methyl-adenosine)
6=2'-O-Me G (2'-O-methyl-guanosine)
7=2'-O-Me C (2'-O-methyl-cytosine)
8=2'-O-Me U (2'-O-methyl-uridine)

Primer 2:

P2G3-5270-7063 (as in example 1)
(SEQ ID NO: 8)
5' CTACAGAACTCAGACAAGATGTGAACTACAATGTT 6

GCTCATACTACAATGTCACTTACTGTAAGAGCAGA 3'

The segment used as the primer in the reaction is underlined.

Said oligonucleotide comprises the following modifications:
6=HEG linker

The following activator oligonucleotide (SEQ ID NO:4) was used:

AD-F5-1001-503 (as in example 1)
(SEQ ID NO: 9)
5'- TAATCTGTAA GAGCAGATCC CTGGACAGGC AA

GGAATACAGGTA GAAGCATC AGAGAA X 3'

Said oligonucleotide comprises the following modifications:

5'[UAAUCUGUAA GAGCAGAUCC CUGGACAGGC AA

GGAAUAC]AGGUAGAAGCATC AGAG X 3'

A=2'-deoxy-adenosine
C=2'-deoxy-cytosine
G=2'-deoxy-guanosine
T=2'-deoxy-thymidine (thymidine)

The 5' segment of the oligonucleotide [UAAUCUGUAA GAGCAGAUCC CUGGACAGGC AA GGAAUAC] comprises 2'-O-Me nucleotide modifications:
Modifications:
A=(2'-O-methyl-adenosine)
G=(2'-O-methyl-guanosine)
C=(2'-O-methyl-cytosine)
U=(2'-O-methyl-uridine)
X=3'-phosphate group for blockage of a possible extension by polymerase.

The nucleotides and nucleotide modifications mutually are linked with phosphodiester bonds. The 3' end of the activator oligonucleotide is blocked with a phosphate group to prevent a possible extension by the polymerase.

As the oligonucleotide probe the following oligonucleotide was employed (SEQ ID NO:10):

P2D-Lux-1000-101
(SEQ ID NO: 10)
5' FAM-TAGTATGAGCTTTT 1 *GCTCATAC* 2 *ACAATGTCACTTA*

*CTGTAAGAGCAGA* 3'

Modifications:
Oligonucleotide labeled with FAM at the 5' end
1=HEG linker
2=dT-BHQ1

A schematic structure of the oligonucleotide probe is illustrated in FIG. 3B (S4.1). Self-complementary segments of the oligonucleotide probe are underlined (stem segment 1 and stem segment 2). The positions are given from the 5' end of the oligonucleotide:

Stem segment 2 (positions 1-10), stem segment 1 (positions 15-25). Loop segment 3 (11-14) between both stem segments comprises an HEG linker. The oligonucleotide probe further comprises a segment 4 (position 26-51) forming a nucleic acid strand with the stem segment 1. Stem segment 1 and segment 4 are able to complementary bind to the 3' segment of the first primer extension product formed during the reaction. Further, the 3' end of the bound oligonucleotide probe can be extended as a primer in the reaction by polymerase.

The fluorescence reporter (FAM) is bound to the 5' end of the oligonucleotide. The quencher (dT-BHQ1) is positioned at position 23. In a state not bound to complementary sequence self-complementary regions of the oligonucleotide can bind to each other. The melting temperature is ca. 70° C. (measured in reaction solution 2 at 0.5 μmol/l of the probe). In this way, fluorescence reporter and quencher are brought into spatial proximity, so that the fluorescence signal from the reporter is reduced. The reduction of the fluorescence signal was ca. 80% of the FAM signal.

In case of a complementary binding to the 3' segment of the primer extension product the double strand is formed between the 3' segment of the first primer extension product and positions 15-51 of the probe, which results in the hindering of the binding of self-complementary segments. Thus, the reporter and the quencher are spaced apart from each other and the intensity of the fluorescence signal increases. From this it was assumed that the intensity of the fluorescence signal should also increase with an increasing extent of the binding of the probe to the 3' segment.

The template was employed in concentrations of 1 pmol/l, 1 fmol/l. In the control reaction no template was employed (=negative control). Primer 1 was employed with 5 mol/l, the activator oligonucleotide with 2 mol/l, and primer 2 with 0.5 μmol/l, and the oligonucleotide probe also with 0.5 μmol/l.

The reactions were carried out with the reaction solutions 2 or 3, depending on whether the oligonucleotide probe or Eva-Green (intercalating dye) generates the signal in the reaction.

The reaction was carried out either with an oligonucleotide probe without EvaGreen or without an oligonucleotide probe but with EvaGreen.

The thermal reaction conditions were cyclic, alternating temperature changes, wherein a 2 min time interval at 55° C. was followed by a 2 min time interval at 65° C. each. The amplification was monitored over 150 cycles. Detection was done at 65° C. both for EvaGreen fluorescence signal and FAM signal.

Successful amplification could be determined by an increase of the FAM fluorescence signal or EvaGreen signal over time.

The temperature changes and real time monitoring were carried out with the StepOne Plus Real-Time PCR apparatus by Thermofisher.

Analysis of the Amplification Reaction

Figure 12:
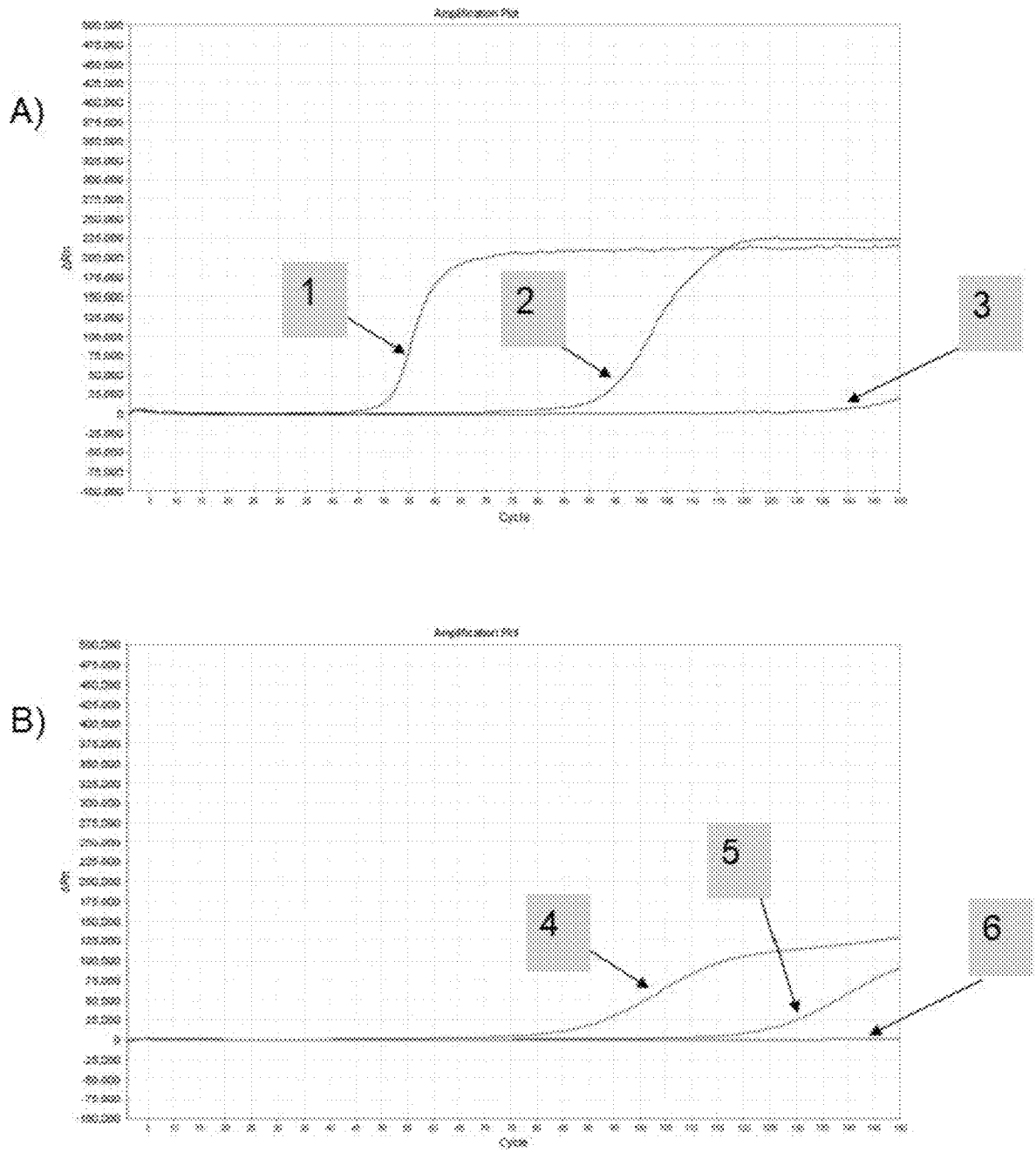
FIG. 12 shows results from example 2.

FIG. 12 A shows a typical course of the EvaGreen signal. FIG. 12 B shows the FAM fluorescence signal during the amplification reaction. On the Y axis the increase in the fluorescence signal (Delta Rn) is plotted and on the X axis the reaction time (as the cycle number). The arrows indicate individual reaction batches. Here, the marked positions belong to the following batches:
Arrow 1: 1 pmol/l template
Arrow 2: 1 fmol/l template
Arrow 3: no template
Arrow 4: 1 pmol/l template
Arrow 5: 1 fmol/l template
Arrow 6: no template It is seen the increase in the fluorescence signal both with EvaGreen and with the probe with the signal of the probe appearing later in time. Here, the cycle number at which a fluorescence increase is achieved correlates with the amount of template employed.

Example 3

Specificity of the Amplification Reaction

In this example, influence of a change in sequence in the template on the amplification has been investigated. When the first primer oligonucleotide is extended a complementary strand is formed that has a sequence complementary to the template and thus comprises these divergences in the sequence. In this way it was to be verified which effect such a mismatch between a first primer extension product generated thereby and an activator oligonucleotide has on the amplification. The position of the mismatch is in 3' direction from the first primer and thus, is not checked by the primer but by the activator oligonucleotide.

The following templates have been used:

Template (SEQ ID NO:1) with a sequence composition that leads to a first primer extension product with a perfect-match in matching with activator oligonucleotide:

```
M2SF5-M001-200 (as in example 2)
                                     (SEQ ID NO: 11)
5' GCT CATA CTACAATGTCA CT TA CTGTAA GAGCAGATCC

CTGGACAGGC AA GGAATACAGGTA AAAAA 3'
```

The binding sequence for the first primer oligonucleotide is underlined. The second primer oligonucleotide binds to the reverse complement of the double-underlined sequence.

Template (SEQ ID NO:1) having a sequence composition resulting in a first primer extension product forming a mismatch with the activator oligonucleotide at a single base position (printed in bold type):

```
M2SF5-WT01-200
                                     (SEQ ID NO: 12)
5' GCT CATA CTACAATGTCA CT TA CTGTAA GAGCAGATCC

CTGGACAGGC GA GGAATACAGGTA AAAAA 3'
```

The binding sequence for the first primer oligonucleotide is underlined. The second primer oligonucleotide binds to the reverse complement of the double-underlined sequence.

The following primers have been used:
the first primer oligonucleotide (SEQ ID NO:2):

```
P1F5-200AE2053 (as in example 1)
                                     (SEQ ID NO 13)
5' AACTCAGACAAGATGTGA TTTTTTTACCTGTAT 7878 65867887 1 TACCTGTATTCC 3'
```

The segment used as primer in the reaction is underlined.
A=2'-deoxy-adenosine
C=2'-deoxy-cytosine
G=2'-deoxy-guanosine
T=2'-deoxy-thymidine (thymidine)
Said oligonucleotide comprises the following modifications:
1=C3 linker
5=2'-O-Me A (2'-O-methyl-adenosine)
6=2'-O-Me G (2'-O-methyl-guanosine)
7=2'-O-Me C (2'-O-methyl-cytosine)
8=2'-O-Me U (2'-O-methyl-uridine)

Primer 2:

```
P2G3-5270-7063 (as in example 1)
                                     (SEQ ID NO: 14)
5' CTACAGAACTCAGACAAGATGTGAACTACAATGTT 6

GCTCATACTACAATGTCACTTACTGTAAGAGCAGA 3'
```

The segment used as primer in the reaction is underlined.
Said oligonucleotide comprises the following modifications:
6=HEG linker
The following activator oligonucleotide (SEQ ID NO:4) was used:

```
AD-F5-1001-503 (as in example 1)
                                     (SEQ ID NO: 15)
5'- TAATCTGTAA GAGCAGATCC CTGGACAGGC AA

GGAATACAGGTA GAAGCATCAGAGAA X 3'
```

Said oligonucleotide comprises the following modification:

```
5'[UAAUCUGUAA GAGCAGAUCC CUGGACAGGC AA

GGAAUAC]AGGTAGAAGCATC AGAG X 3'
```

A=2'-deoxy-adenosine
C=2'-deoxy-cytosine
G=2'-deoxy-guanosine
T=2'-deoxy-thymidine (thymidine)
The 5' segment of the oligonucleotide [UAAUCUGUAA GAGCAGAUCC CUGGACAGGC AA GGAAUAC] comprises 2'-O-Me nucleotide modifications:
Modifications:
A=(2'-O-methyl-adenosine)
G=(2'-O-methyl-guanosine)
C=(2'-O-methyl-cytosine)
U=(2'-O-methyl-uridine)
X=3'-phosphate group for blockage of a possible extension by polymerase.

The nucleotides and nucleotide modifications mutually are linked to phosphodiester bonds. The 3' end of the activator oligonucleotide is blocked with a phosphate group to prevent a possible extension by the polymerase.

Four Batches were Prepared:

Batch 1 as the start nucleic acid chain contains template M2SF5-M001-200 (Perfect Match Situation) in a concentration of 300 fmol/l (corresponds to ca. 2×10^6 copies/batch).

Batch 2 as the start nucleic acid chain contains template M2SF5-M001-200 (Perfect Match Situation) in a concentration of 300 amol/l (corresponds to ca. 2×10^3 copies/batch).

Batch 3 contains no template and thus, forms a control.

Batch 4 as the start nucleic acid chain contains template M2SF5-WT01-200 (single Mismatch Situation) in a concentration of 300 pmol/l (ca. 2×10^9 copies/batch).

Primer 1 was employed with 5 mol/l, the activator oligonucleotide with 2 mol/l, and primer 2 with 1 mol/l.

The further reaction conditions were: amplification solution 2.

To simulate the presence of genomic DNA in the assay 100 ng freshly denatured fish DNA (salmon DNA) were added per reaction.

The thermal reaction conditions were cyclic alternating temperature changes, wherein a 2 min time interval at 55° C. was followed by a 5 min time interval at 65° C. each. The amplification was monitored over 100 cycles. Detection was done at 65° C. for EvaGreen fluorescence signal.

Successful amplification could be observed by an increase in the EvaGreen fluorescence signal overtime.

The temperature changes and real time monitoring were carried out with the StepOne Plus Real-Time PCR apparatus by Thermofisher.

Figure 13:
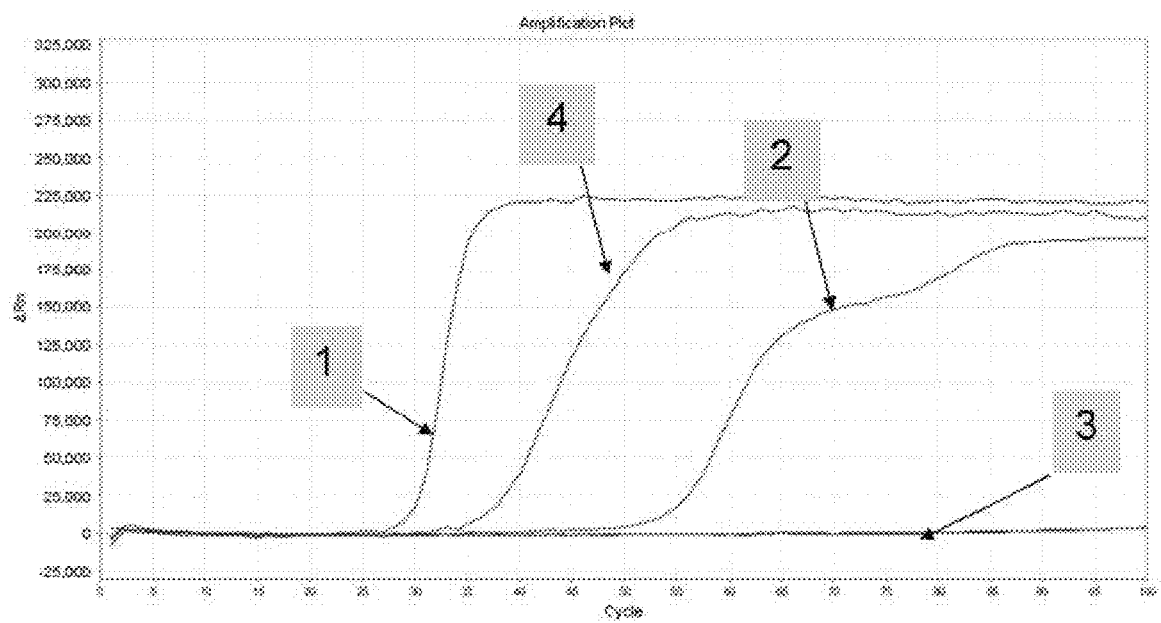
FIG. 13 shows results from example 3.
Figure 14:
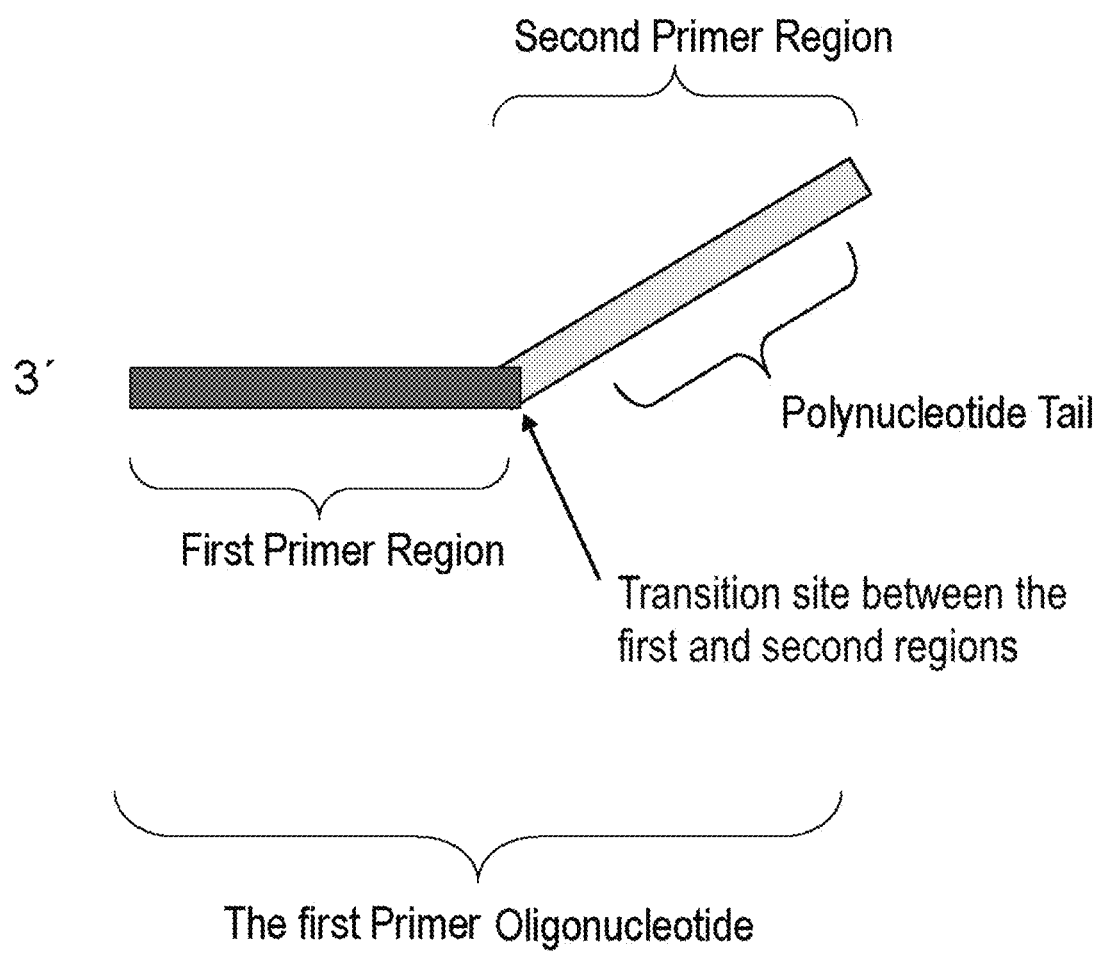
Figure 15:
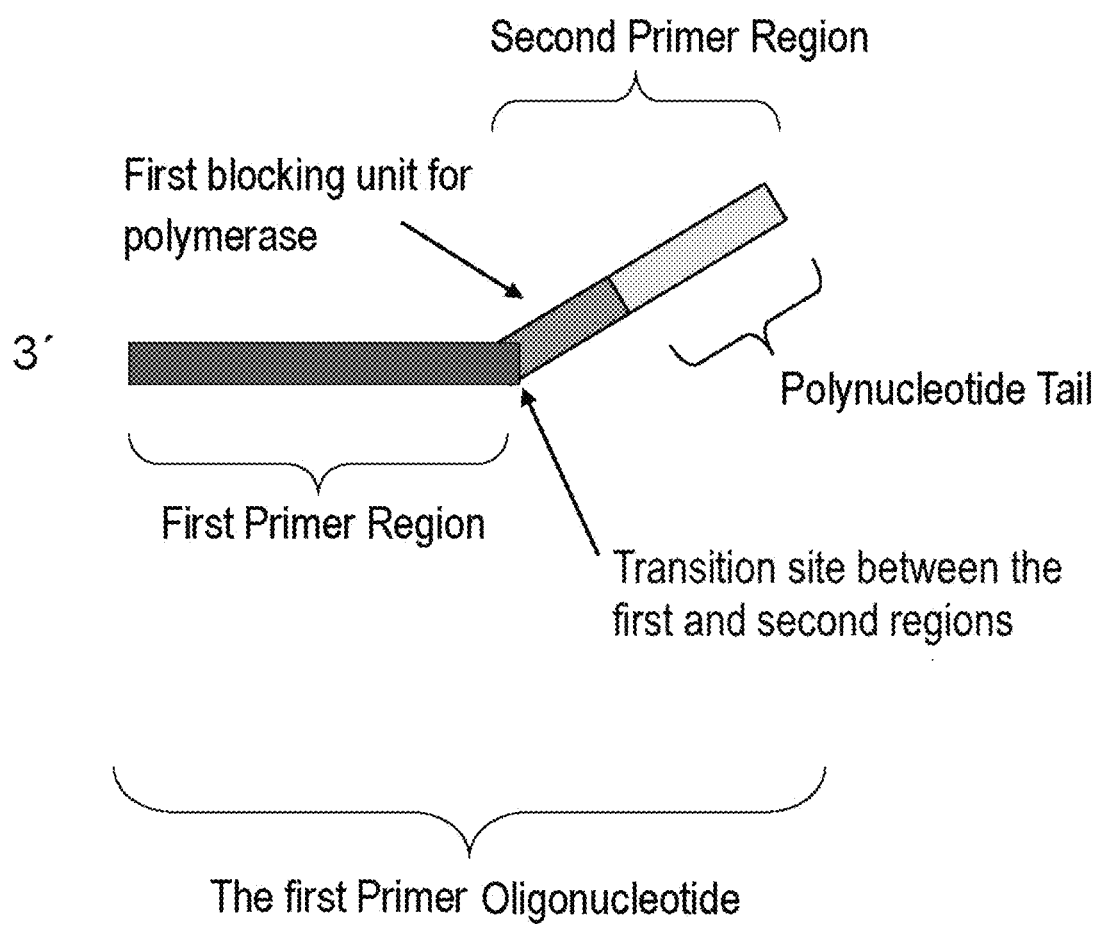

FIG. 13A shows a typical course of the EvaGreen signal. On the Y axis the increase in the fluorescence signal (Delta Rn) is plotted and on the X axis the reaction time (as the cycle number). The arrows indicate individual reaction batches. Here, the marked positions belong to the following batches:

Arrow 1: 300 fmol/l perfect match template (ca. $2 \times 10^6$ copies/batch)
Arrow 2: 300 amol/l perfect match template (ca. $2 \times 10^3$ copies/batch)
Arrow 3: no template
Arrow 4: 300 pmol/l mismatch template (ca. $2 \times 10^9$ copies/batch).

The increase of the fluorescence signal can be seen both with the perfect match and the mismatch variant of the template, wherein the signal of the mismatch variant (4) appears later despite a 100-fold excess. It can be seen that the mismatch amplification signals are significantly delayed over the perfect match amplification signal. With the single mismatch a delay of ca. 15 cycles is observed. The time lag (=cycle number) is a direct measure for the discrimination in the amplification. A further quantification of the discrimination in the amplification may be achieved by comparing it with a template concentration series under perfect match amplification.

When using a perfect match template, a complementary strand of a primer extension product is synthesized. Said extension product is complementary both to the perfect match template and to the activator oligonucleotide used. This constellation was illustrated in detail in example 2. It can be used as a basis for a successful amplification.

In contrast, when using a mismatch sequence, a complementary strand of the extension product is generated in the synthesis of the first primer extension product, which certainly has a complete complementarity to the mismatch template, but that way deviates from the complementarity with the third region of the activator oligonucleotide. Said deviation takes place in the 5'-standing segment of the extension product which is to react with the activator oligonucleotide in order that the strand displacement process can proceed. As is shown in the preceding example, the mismatch interferes with a strand displacement by the activator oligonucleotide.

The control reactions with a perfect match template (arrows 1 and 2) showed a concentration dependency of the amplification. With decreasing concentration the reaction took more time to synthesize a sufficient amount of the nucleic acid to be amplified in order that the signal increases above the level of the baseline.

Said result illustrates the importance of the base composition in the activator oligonucleotide: Deviations from the complementarity between the activator oligonucleotide and the primer extension product may result in a deceleration or even interruption of the amplification.

In this example it has been shown that although sequence ends of a perfect match template and a mismatch template are consistent and thus, the potential to bind of both primer oligonucleotides was the same both reactions had a completely different course: in case of a complete complementarity between the activator oligonucleotide and the 5' segment of the extension product of the first primer oligonucleotide amplification was as planned. An interruption of the strand displacement by a sequence deviation (in this case by a mismatch) resulted in the suppression of the amplification.

---

The invention claimed is:

1. A method for amplification of a nucleic acid comprising the following steps:
   a) hybridizing a first primer oligonucleotide to the 3' segment of a strand of a nucleic acid chain to be amplified, wherein the nucleic acid chain to be amplified comprises a target sequence, wherein the first primer oligonucleotide comprises:
      a first primer region in the 3' segment of the first primer oligonucleotide that can sequence-specifically bind to a strand of a nucleic acid chain to be amplified,
      a second region that is directly or via a linker linked to the 5' end of the first primer region of the first primer oligonucleotide and that comprises a polynucleotide tail which is suitable for binding an activator oligonucleotide and supporting strand displacement by the activator oligonucleotide, wherein the polynucleotide tail remains substantially uncopied by polymerase,
   b) extending the first primer oligonucleotide by means of a polymerase to form a first primer extension product comprising a sequence that is complementary to the target sequence of the nucleic acid chain a) to be amplified,
   c) binding the activator oligonucleotide to the polynucleotide tail of the second region of the first extended primer oligonucleotide, wherein the activator oligonucleotide comprises:
      a first single-stranded region that can bind to the polynucleotide tail of the second region of the first primer oligonucleotide,
      a second single-stranded region that is substantially complementary and can bind to the first region of the first primer oligonucleotide,
      a third single-stranded region that is substantially complementary to at least a segment of the extension product, which has been synthesized by polymerase, of the first primer extension product,
   wherein the activator oligonucleotide does not serve as template for a primer extension of the first primer oligonucleotide,
   d) binding the activator oligonucleotide to the first primer region of the first extended primer oligonucleotide by displacing the strand of the nucleic acid chain to be amplified that is complementary to said first primer region,
   e) binding the activator oligonucleotide to the complementary segment of the extension product of the first extended primer oligonucleotide by displacing the strand of the nucleic acid chain to be amplified that is complementary to said extension product, wherein the 3' segment of the first primer extension product becomes single-stranded,
   f) hybridizing a second primer oligonucleotide to the first primer extension product, wherein the 3' segment of the second oligonucleotide primer comprises a sequence that can hybridize to the first primer extension product; and
   g) extending the second primer oligonucleotide with polymerase to form a second primer extension product, wherein the extension takes place up to and including the first primer region of the first primer oligonucleotide and said first primer region is copied by the polymerase, wherein the polynucleotide tail of the second region remains uncopied,
   h) repeating steps a)-g) until the desired degree of amplification has been achieved, and wherein a detection system is added to the reaction mixture.

2. The method according to claim 1, wherein the detection system has a fluorescence reporter molecule and signal quencher molecule, connected thereto via a nucleotide sequence, wherein the nucleotide sequence is complementary to a part of the target sequence.

3. The method according to claim 1, wherein the detection system has a fluorescence reporter molecule bound to a component that is employed in the method and that a fluorescence donor or a fluorescence quencher are employed, connected to another component used in the method, wherein a spatial proximity or spatial absence is caused in the absence or presence, respectively, of the target sequence to be detected.

4. The method according to claim 1, wherein a fluorescence resonance energy transfer is present in the detection system.

5. The method according to claim 1, wherein the method is carried out substantially isothermal.

6. The method according to claim 1, wherein the third single-stranded region of the activator oligonucleotide is substantially complementary to the segment of the extension product, which has been synthesized by the polymerase, of the first primer extension product, which immediately follows the first primer region.

7. The method according to claim 1, wherein step (e) of the method is modified in that it comprises the binding of the activator oligonucleotide to the complementary segment of the extension product of the first extended primer oligonucleotide by displacing the strand of the nucleic acid chain to be amplified that is complementary to said extension product until said complementary strand of the nucleic acid to be amplified is detached from the first primer extension product, wherein the 3' segment of the first primer extension product becomes single-stranded.

8. The method according to claim 1, wherein step (f) of the method is modified in that it comprises the hybridization of a second oligonucleotide primer to the first primer extension product, wherein at the same time there is at least a partial displacement of the activator oligonucleotide from the binding with the first extension product by strand displacement.

9. The method according to claim 1, wherein step (g) of the method is modified such that it comprises a displacement of the activator oligonucleotide from the binding with the first primer extension product with the participation of the polymerase.

10. The method according to claim 1, wherein step (h) of the method is modified in that it comprises the binding of the activator oligonucleotide to the uncopied polynucleotide tail of the first extended primer oligonucleotide and a displacement of the second primer extension product from the binding to the first primer extension product with the simultaneous formation of a complementary double strand with a segment of the first specific extension product of the first primer oligonucleotide.

11. The method according to claim 1, wherein the repetition of the steps is performed under such conditions that allow the repetition of the steps (a) to (g).

12. The method according to claim 1, wherein it comprises the simultaneous amplification of the first and second primer extension products in an exponential reaction by using the first and second primer oligonucleotides and the activator oligonucleotide, wherein the formed primer extension products function as a template for the mutual synthesis.

13. Use of a kit for carrying out a method according to claim 1, wherein the kit contains at least one first primer oligonucleotide, at least one activator oligonucleotide, and at least one polymerase for amplification, and a detection system.

14. Use of a kit according to claim 13, wherein the kit further contains a second oligonucleotide primer.

* * * * *

SEQUENCE LISTING

<160> NUMBER OF SEQ ID NOS: 15

<210> SEQ ID NO 1
<211> LENGTH: 38
<212> TYPE: DNA
<213> ORGANISM: Homo sapiens

<400> SEQUENCE: 1
gtaagagcag atccctggac aggcaaggaa tacaggta                              38

<210> SEQ ID NO 2
<211> LENGTH: 45
<212> TYPE: DNA
<213> ORGANISM: artificial sequence
<220> FEATURE:
<223> OTHER INFORMATION: primer

<400> SEQUENCE: 2
aactcagaca agatgtgatt tttttacctg tattacctgt attcc                      45

<210> SEQ ID NO 3
<211> LENGTH: 70
<212> TYPE: DNA
<213> ORGANISM: artificial sequence
<220> FEATURE:
<223> OTHER INFORMATION: primer

<400> SEQUENCE: 3
ctacagaact cagacaagat gtgaactaca atgttgctca tactacaatg tcacttactg    60
taagagcaga                                                           70

<210> SEQ ID NO 4
<211> LENGTH: 58
<212> TYPE: DNA
<213> ORGANISM: artificial sequence
<220> FEATURE:
<223> OTHER INFORMATION: activator oligonucleotide

<400> SEQUENCE: 4
taatctgtaa gagcagatcc ctggacaggc aaggaataca ggtagaagca tcagagaa      58

<210> SEQ ID NO 5
<211> LENGTH: 52
<212> TYPE: DNA
<213> ORGANISM: artificial sequence
<220> FEATURE:
<223> OTHER INFORMATION: primer

<400> SEQUENCE: 5
aagctcgaca aaagaactca gagtgtgctc gacactacct gtattccttg cc            52

<210> SEQ ID NO 6
<211> LENGTH: 67
<212> TYPE: DNA
<213> ORGANISM: artificial sequence
<220> FEATURE:
<223> OTHER INFORMATION: activator oligonucleotide

<400> SEQUENCE: 6
gctcatacta caatgtcact tactgtaaga gcagatccct ggacaggcaa ggaatacagg    60
taaaaaa                                                              67

<210> SEQ ID NO 7
<211> LENGTH: 45
<212> TYPE: DNA
<213> ORGANISM: artificial sequence
<220> FEATURE:
<223> OTHER INFORMATION: primer

<400> SEQUENCE: 7
aactcagaca agatgtgatt tttttacctg tattacctgt attcc                    45

<210> SEQ ID NO 8
<211> LENGTH: 70
<212> TYPE: DNA
<213> ORGANISM: artificial sequence
<220> FEATURE:
<223> OTHER INFORMATION: primer

<400> SEQUENCE: 8
ctacagaact cagacaagat gtgaactaca atgttgctca tactacaatg tcacttactg    60
taagagcaga                                                           70

<210> SEQ ID NO 9
<211> LENGTH: 58
<212> TYPE: DNA
<213> ORGANISM: artificial sequence
<220> FEATURE:
<223> OTHER INFORMATION: activator oligonucleotide

<400> SEQUENCE: 9
taatctgtaa gagcagatcc ctggacaggc aaggaataca ggtagaagca tcagagaa    58

<210> SEQ ID NO 10
<211> LENGTH: 48
<212> TYPE: DNA
<213> ORGANISM: artificial sequence
<220> FEATURE:
<223> OTHER INFORMATION: probe

<400> SEQUENCE: 10
tagtatgagc ttttgctcat acacaatgtc acttactgta agagcaga    48

<210> SEQ ID NO 11
<211> LENGTH: 67
<212> TYPE: DNA
<213> ORGANISM: artificial sequence
<220> FEATURE:
<223> OTHER INFORMATION: activator oligonucleotide

<400> SEQUENCE: 11
gctcatacta caatgtcact tactgtaaga gcagatccct ggacaggcaa ggaatacagg    60
taaaaaa    67

<210> SEQ ID NO 12
<211> LENGTH: 67
<212> TYPE: DNA
<213> ORGANISM: artificial sequence
<220> FEATURE:
<223> OTHER INFORMATION: activator oligonucleotide

<400> SEQUENCE: 12
gctcatacta caatgtcact tactgtaaga gcagatccct ggacaggcga ggaatacagg    60
taaaaaa    67

<210> SEQ ID NO 13
<211> LENGTH: 45
<212> TYPE: DNA
<213> ORGANISM: artificial sequence
<220> FEATURE:
<223> OTHER INFORMATION: primer

<400> SEQUENCE: 13
aactcagaca agatgtgatt tttttacctg tattacctgt attcc    45

<210> SEQ ID NO 14
<211> LENGTH: 70
<212> TYPE: DNA
<213> ORGANISM: artificial sequence
<220> FEATURE:
<223> OTHER INFORMATION: primer

<400> SEQUENCE: 14
ctacagaact cagacaagat gtgaactaca atgttgctca tactacaatg tcacttactg    60
taagagcaga    70

```
<210> SEQ ID NO 15
<211> LENGTH: 58
<212> TYPE: DNA
<213> ORGANISM: artificial sequence
<220> FEATURE:
<223> OTHER INFORMATION: activator oligonucleotide

<400> SEQUENCE: 15
taatctgtaa gagcagatcc ctggacaggc aaggaataca ggtagaagca tcagagaa      58
```